(12) United States Patent
Yao et al.

(10) Patent No.: US 9,023,608 B2
(45) Date of Patent: May 5, 2015

(54) MODIFIED GLUCOSE DEHYDROGENASE

(75) Inventors: Masafumi Yao, Kyoto (JP); Shido Kawase, Kyoto (JP); Shin-ichi Yokobori, Tokyo (JP); Akihiko Yamagishi, Tokyo (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 14/008,927

(22) PCT Filed: Mar. 30, 2012

(86) PCT No.: PCT/JP2012/058568
§ 371 (c)(1),
(2), (4) Date: Sep. 30, 2013

(87) PCT Pub. No.: WO2012/133761
PCT Pub. Date: Oct. 4, 2012

(65) Prior Publication Data
US 2014/0030749 A1 Jan. 30, 2014

(30) Foreign Application Priority Data
Mar. 30, 2011 (JP) ................................. 2011-075449

(51) Int. Cl.
C12N 9/04 (2006.01)
C12Q 1/54 (2006.01)
C12P 21/02 (2006.01)
C12Q 1/32 (2006.01)

(52) U.S. Cl.
CPC ............. *C12N 9/0006* (2013.01); *C12P 21/02* (2013.01); *C12Q 1/32* (2013.01); *C12Q 1/54* (2013.01); *C12Y 101/01047* (2013.01)

(58) Field of Classification Search
None
See application file for complete search history.

(56) References Cited

U.S. PATENT DOCUMENTS

| 2005/0095619 A1 | 5/2005 | Davis et al. |
| 2011/0236770 A1 | 9/2011 | Sakai et al. |

FOREIGN PATENT DOCUMENTS

| JP | 2003-310274 A | 11/2003 |
| JP | 2007-502114 A | 2/2007 |
| JP | 2010-219021 A | 9/2010 |
| WO | 2010/041511 A1 | 4/2010 |

OTHER PUBLICATIONS

Chen et al. A_Geneseq, Accession No. AYH04468, Sep. 30, 2010.*
Weinstock et al. UniProt, accession No. E2ZBIO (Jan. 11, 2013).*
Eduardo Vazquez-Figueroa, et al; "Development of a Thermostable Glucose Dehydrogenase by a Structure-Guided Consensus Concept"; ChemBioChem 2007, vol. 8, pp. 2295-2301.
E. Vazquez-Figueroa; et al; "Thermostable variants constructed via the structure-guided consensus method also show increased stability in salts solutions and homogeneous aqueous-organic media"; Protein Engineering, Design & Selection, 2008, vol. 21, No. 11, pp. 673-680.
Ding et al., "Cloning and expression in *E. coli* of an organic solvent-tolerant and alkali-resistant glucose 1-dehydrogenase from *Lysinibacillus sphaericus* G10", Bioresource Technology, vol. 102, Jan. 2011, ISSN: 0960-8524, 9 pages.
European Patent Office, Supplementary Partial European Search Report, dated Dec. 22, 2014, issued in counterpart European Application No. 12765279.0.

* cited by examiner

*Primary Examiner* — Nashaat Nashed
(74) *Attorney, Agent, or Firm* — Sughrue Mion, PLLC

(57) ABSTRACT

The present invention relates to glucose dehydrogenase [NAD(P)$^+$GDH] using nicotinamide adenine dinucleotide or nicotinamide adenine dinucleotide phosphate as a coenzyme, in which the thermal stability and/or the resistance to an organic solvent in the absence of sodium chloride are improved.

20 Claims, 9 Drawing Sheets

Figure 1

```
                                      :**. *:        .       .
Seq01 -------------------------------MPAPYKDRFAGKKVLVTGASQGIGEATALRFAEEGA   36
Seq02 ------------------------------MINLDLQGRRALVTGGSGGLGRAIAETLATAGA       33
Seq03 -----------------------MDENRGSRIAINLTGKIALVTGSSSGLGAAIAKYMARAGA       40
Seq04 ------------------------------MEIRLDGKRALVTGGSSGIGAAIAVELGAAGA        32
Seq05 -----------------------------MVEQFLSGKVAIVTGANTGIGKAIAEELAKRGA        33
Seq06 -----------------------MSPTSKSSTSRPLEDRVVIVTGGNSGIGEGIVREAAAQGA       40
Seq07 -----------------------------MVQGRLAGRKALVTGSTQGIGAAIALRLAQDGA        33
Seq08 ------------------------------MGRMENKVCVITGSTSGIGEACAKDMAAEGG         31
Seq09 -----------------------------MTNKPFAGKVALVTGAASGIGRASALAFAQQGA        33
Seq10 MVKEVFESIEDYEKSLEERIQSGSMGYRKMPDLTGKVAIVTGATGGLGGPIALGLADFGC         60
Seq11 --------MSTVAARALASRSSVAKFASRAAKHASGPVCVVTGASRGIGAAIALALGQQGA        53
Seq12 ------------------------------MANLSGKVAIVTGAGQGIGRGIALRLARDGA        31
Seq13 ------------------------------MRVQGSVVLVTGSSRGIGRAVAVEAARRGA         30
Seq14 -----------------------MDVLKLFSLEGKVAIVTGASRGLGQAMAIALAEAGA          36
Seq15 ------------------------------MYPDLKGKVVAITGAASGLRKAMAIRFGKEQA       32

:.              *         :::       :        :::
Seq01 Q-VALNGRKEDKLIAVREKLPKVSGGEHPIATGDISKE-DDVKRLVAESIKAMGGLDVLV         94
Seq02 Q-VAVHYRKGLDEAEAVVAAIQKRGGTAQAFQADVADP-AAVERLLQEIESAFGGLDILV         91
Seq03 K-VAVHYRSGKDRADAIVDEIKNDGGFAMAFYGDVSKK-EDVQKLFSEIDSKLGTVDILV         98
Seq04 K-VVVNYRSHADAAAEIVRQITDVGGQATAVQADVSDQ-SAVVKMFEQMDDVYGGIDILI         90
Seq05 K-VVVNYRSHPERTDEMISAIKAAGGEAMGAQADVTHL-DQLQAVVDQAVSSYGRLDIMV         91
Seq06 K-VVIDFVSHPEATDAIIKDVEAAGGEAIGCQADVSKV-ADLEKLIAAAVGAYGRVDVMV         98
Seq07 D-VVLNGRDPDGAPGGLIECIAALGCRAVYVAADLSSGAAEAGRLVDEAAQALRGLDILV         92
Seq08 K-VVVSGRNEKE-GARIVNEIKEAGGEVIFIRADVTVE-DDVRNLVAKTVEAFGRLDVFV         88
Seq09 K-VVVADVNVSG-GEETVRMIVDNGGEAIPVATDVSRA-AEVEALVRQTIAQFGRLDVAH         90
Seq10 D-VVVVGRR-LEVVLEKLKESIEKLGQRALAVKCDITSE-EDVANLVNRTVEEFGRIDILV       117
Seq11 R-VVVNYAASEGPANEVCEKIKAAGGDAIAVKANVAVP-EDVDALFKATMDKFGEVNVLV        111
Seq12 I-VVATDITGKE---NEVAEEVRKLGGQGMALRLDVTDG-KMAEEVARTVFDKYGHIDILV       87
Seq13 KGVVVNYVSRRDAAEETARLVKEAGAVPLVVRADVSVY-EEARKLVEAAIEKWGRLDVVV        89
Seq14 D-IVGVSRSEAE-QSETKMAIEKIGRRYFAIGMDLSQF-EKIGSIVESAVKKFGRVDILV        93
Seq15 K-VVINYYSNKQDPNEVKEEVIKAGGEAVVVQGDVTKE-EDVKNIVQTAINEFGTLDIMI        90

:.           :       :  ..  .    :                 . ::     *
Seq01 CNAGYQIPS-PSEDIKLEDFEGVMAVNVTGVMLPCREVIRYWLEN-GIKGTIIVNSSVHQ   152
Seq02 NNAGMDGPRASVGDDDPQVWEKVLAVDLMGPYYCARAAIPRMEKA--KRGVIINITSVHE   149
Seq03 NNAGIDGKRVMSWEIDPDDPDDWEKVIEVNLMGPYYCAREAVKRMKPK--KSGVIINITSVHE 156
Seq04 NNAGIDGKRVMSWEIDPEDWRKVIDVNMLGSFYCAQQALKRMIPA---SSGVVISVSSVHE   148
Seq05 NNAGLETRT-SVLDTTPEDYDRVLDVNLKSAFFGTQFAAKQMIKQ-GGGGRIINISSVHE    149
Seq06 NNAGVEFGE-TLATLTEEKYDLLMNINLKGAVFGSKLAAEQMRKQ-GDGGVIVNITSTHE    156
Seq07 NNAGVERRA-DFWDVTEEDYDLVMDTNVKGLFFATQAFVRHLRAR-KDEGAIVNISSVHE    150
Seq08 ANSGVGSLG-DPHEVETEEWDRVLDVNLKGIFLCDKYAVQQMLKQ-GQGGAIVNTGSIHS    146
Seq09 NNAAIEGALAPTAAYSEEDWDRTINVNLKGTWLCLKYEILHMLQQ--GGGAIVNTASVVG    148
Seq10 NCAGINIPK-PAEEYPLEDWNKVMDANVTGVFLVCREVGKVMVKQ--NGGKIINVSSVRS    174
Seq11 NNAGITRDT-LMMRMKLQQWQEVIDLNLTGVFLCTQAATKAMGKKKPVSGRIINITSVVG    170
Seq12 NNAGIYPPK-PFMEMTFNDWYRVINVNLNGVFNVTRAVVPYMVKQ--KNGRIINIASIAG    144
Seq13 NNAGILEPK-LFEDMKPRDWQRMIEVHFYGALNVAHAAIPYMKRN--GGGVIVNIASVLG    146
Seq14 NNAGVIKRA-PVTEYSVEDWDKVLNINLKAAFLLSQYFSRYAIEN-GIKARIINVASMLS    151
Seq15 NNAGLENPV-PSHEMPLKDWDKVISTNLTGAFLGSREAIKYFVEN-DIKGNVINMSSVHE    148
```

Figure 2

```
                    *  :*  .:    .   ...     :     : *       :
Seq01   IIPKP-HYLGYSASKGAVGNIVRTLALEYATRGIRVNAVAPGAIVTPINMSWIDDPEQYK    211
Seq02   FIPWE-GYSAYTSAKAGLSMFTKTLAQETADKGIRVVAIAPGAIQTPINQSVWSDPQSLK    208
Seq03   YVPWS-GYTAYSSAKAGLSMFTKALAQELSDYNIRVVAIAPGAIKTPINKDVWGNPESLK    215
Seq04   EIAWS-GYSAYAASKSGVAMMTKTLAQEAAPYGVRVLAIAPGAIKTAINKPVWSDPEQRK    207
Seq05   DWPMP-NNTAYCLSKGGVRMLTRTAGVELAPHGITMVNIGPGAVDTPINASYAGNRTLLD    208
Seq06   DWPMP-SDLAYCISKGGMRMLTRTAGVELGADKIRMVGVGPGAINTPINADDT--PAETT    213
Seq07   EIAFP-HFASYCASKGALRMLARNLASELAPLGIRVNNVAPGAIATPINAQLMDNPEQLR    209
Seq08   FVAKQ-GVTAYGAAKGGVAMLTRTLGTSYAAQGIRANFVAPGYIDTFLLAALP--REAYE    203
Seq09   LVGTI-GLPAYCAAKGGVVQLTKAAALEYAKAGIRINAVCPGATHTPMLNRLMVQPGAET    207
Seq10   SYGMPKNYIAYCSSKAAVNMITKQLACEWAKYNILVNAIAPTVIATPLTAHIMKDPELSK    234
Seq11   VTGNA-GQANYSAAKAGVIGLTKTVAREYAGRNIQCNAIAPGFIASDMTAVLG--EELEK    227
Seq12   AVMGFMGLTHYSASKAGIVGFTRALALELARYGITVNAIAPGAINTPGAATGS--EEQVR    202
Seq13   LRPEP-BASHYSAAKAALIAWTIAVAKELADYNIRVFAVAPGGVDTDMTRAWG----DMD    201
Seq14   FQGGIF-TTAYTVSKHGIVGLTRIFANELARYGITVNAIAPGYMETDNTAALRNDRNRSM    210
Seq15   VIPWP-LFVHYAASKGGIKLMTETLALEYAPKGIRVNNIGPGAINTPINAEKFADPKQRA    207

:           .   ::         .        ::.    .**
Seq01   AVSSHIPMKRPGESREIADAITFLAAEDST-YITGQTLYVDGGLTLYGDFENNWSS      266
Seq02   DLNEKISMGRLGNPEEIGNVAAFLASDLAS-YITGTTLAVDGGMLIYPEFRHGG--      261
Seq03   DLLNKIAMPRLGEVDDIGQAAVFLASDLAS-YITGTTLLVDGGMALYPDFKHGG--      268
Seq04   DLLTKIPLNRIGEPKEIAEMTVVLASDVAS-YITGRTIFIDGGMTDYPSFAEGG--      260
Seq05   KLDAAIPLGRMAEPQEIASVAAFVASDGAS-YITATSIPADGGIMQSSPGL-----      258
Seq06   ALEKAIPLSYIGSPQEMGKVVCFAASEAAS-YITATTIIADGGLMQKPGAV-----      263
Seq07   ALNAQIPLGRMGQPEDVAGLVAFLSGDEAR-YITGGTHPVDGGLTYHYTEQ-----      259
Seq08   ELKKLHPIGRLGRPMEVAKAVTFLASDDAS-NITGTSLLVDGGYTAV---------      249
Seq09   GMLATIPLGRIGNPEEIAAAVVWLCSDAAS-YVTGHIMVVDGGMIAQ---------      253
Seq10   TMKSRILLGRWGYPDDLIGAVVFFASDASN-FVTGQILYIDGGVTSWA--------      281
Seq11   KILTTIPAGRYGQPEEIAGLVKFLAMDPAAAYITGQTLHVDGGMVM----------      273
Seq12   MMINAIPMGKLGTPEDIASAVAYLASDEAS-YITGALIVIDGGWSIT---------      248
Seq13   WVEEQIPLRRLAKPEEVAKIVLDAVENP---YVSGDVLTISGGLL-----------      243
Seq14   EILSRIPMGRWGKPDDLKGAVVFLASSAAD-YVTGTVLAVDGGWLSR---------      256
Seq15   DVESMIPMGYIGEPEEIAAVAAWLASKEAS-YVTGITLFADGGMTQYPSFQAGRG-      261
```

Figure 7

```
                                                    .   :**.  *:     .            .
Seq01    ---------------------------MPAPYKDRFAGKKVLVTGASQGIGEATALRFAEEGA            36
Seq02    ------------------------MINLDLQGRRALVTGGSGGLGRAIAETLATAGA                  33
Seq03    ----------------MDENRGSRIAINLTGKIALVTGSSSGLGAAIAKYMARAGA                    40
Seq04    ------------------------MEIRLDGKRALVTGGSSGIGAAIAVELGAAGA                    32
Seq05    -----------------------MVEQFLSGKVAIVTGANTGIGKAIAEELAKRGA                    33
Seq06    ----------------MSPTSKSSTSRPLEDRVVIVTGGNSGIGEGIVREAAAQGA                    40
Seq07    ------------------------MVQGRLAGRKALVTGSTQGIGAAIALRLAQDGA                   33
Seq08    --------------------------MGRMENKVCVITGSTSGIGEACAKDMAAEGG                   31
Seq09    ------------------------MTNKPFAGKVALVTGAASGIGRASALAPAQQGA                   33
Seq10    MVKEVFESIEDYEKSLEERIQSGSMGYRKMPDLTGKVAIVTGATGGLGGPIALGLADFGC                 60
Seq11    --------MSTVAARALASRSSVAKFASRAAKHASGPVCVVTGASRGIGAAIALALGQQGA                53
Seq12    ----------------------------MANLSGKVAIVTGAGQGIGRGIALRLARDGA                  31
Seq13    ---------------------------MRVQGSVVLVTGSSRGIGRAVAVEAARRGA                    30
Seq14    ----------------------MDVLRLFSLEGKVAIVTGASRGLGQAMAIALAEAGA                    36
Seq15    ---------------------------MYPDLKGKVVAITGAASGLRKAMAIRFGKEQA                  32
Tre1Anc  MVKEVFEMITVYARALAERIMSANMGSMMEARLSGKVALVTGASSGIGKAIALRLAQEGA                 60
Tre2Anc  MVKEVFEMITVYARALAERIMSANMGSMMMKRLSGKVALVTGASSGIGKAIALRLAQEGA                 60
Tre3Anc  MVKEVFEMITVYARALASRIMSANMGSMMEARLSGKVALVTGASSGIGKAIALELAQEGA                 60
Tre4Anc  MVKEVFEMSTVYARALASRSMSANMGSMMEARLEGKVALVTGASSGIGKAIALRLAQEGA                 60

:.                         *          :::         :             :::
Seq01    Q-VALNGRKEDKLIAVREKLPKVSGGEHPIATGDISKE-DDVKRLVAESIKAMGGLDVLV                94
Seq02    Q-VAVHYRKGLDEAEAVVAAIQKRGGTAQAFQADVADP-AAVERLLQEIESAFGGLDILV                91
Seq03    K-VAVHYRSGKDRADAIVDEIKNDGGFAMAFYGDVSKK-EDVQKLFSEIDSKLGTVDILV                98
Seq04    K-VVVNYRSHADAAAEIVRQITDVGGQATAVQADVSDQ-SAVVKMFEQMDDVYGGIDILI                90
Seq05    K-VVVNYRSHPERTDEMISAIKAAGGEAMGAQADVTHL-DQLQAVVDQAVSSYGRLDIMV                91
Seq06    K-VVIDFVSHPEATDAIIKDVEAAGGEAIGCQADVSKV-ADLEKLIAAAVGAYGRVDVMV                98
Seq07    D-VVLNGRDPDGAPGGLIECIAALGCRAVYVAADLSSGAAEAGRLVDEAAQALRGLDILV                92
Seq08    K-VVVSGRNEKE-GARIVNEIKEAGGEVIFIRADVTVE-DDVRNLVARTVEAFGRLDVFV                88
Seq09    K-VVVADVNVSG--GEETVRMIVDNGGEAIFVATDVSRA-AEVEALVRQTIAQFGRLDVAH               90
Seq10    D-VVVVGRR--LEVLEKLKESIEKLGQRALAVKCDITSE-EDVANLVNRTVEEFGRIDILV               117
Seq11    R-VVVNYAASEGPANEVCEKIKAAGGDAIAVKANVAVP-EDVDALFKATMDKFGEVNVLV                111
Seq12    I-VVATDITGKE--NEVAEEVRKLGGQGMALRLDVTDG-KMAEEVARTVFDKYGHIDILV                87
Seq13    KGVVVNYVSRRDAAEETARLVKEAGAVPLVVRADVSVY-EEARKLVEAAIEKWGRLDVVV                89
Seq14    D-IVGVSRSEAE-QSETKMAIEKIGRRYFAIGMDLSQF-EKIGSIVESAVKKFGRVDILV                93
Seq15    K-VVINYYSNKQDPNEVKEEVIKAGGEAVVVQGDVTKE-EDVKNIVQTAINEFGTLDIMI                90
Tre1Anc  KGVVVNYRSHKEAADEIVEEIKKAGGEAMAVQADVSKEAEDVQKLVEQTVDAFGRLDILV                120
Tre2Anc  KGVVVNYRSHKEAADEIVEEIKKAGGEAIAVRADVSKEAEDVEKLVEQTVDAFGRLDILV                120
Tre3Anc  KGVVVNYRSHKEAADEIVEEIKKAGGEAMAVQADVSKEAEDVQKLVEQTVDAFGRLDILV                120
Tre4Anc  KGVVVNYRSHKEAADEIVEEIKKAGGEAMAVQADVSKEAEDVQKLVEQTVDAFGRLDILV                120
```

Figure 8

```
            :.                  :    :  ..  .          :              .  ::        *
  Seq01  CNAGYQIPS-PSEDIKLEDFEGVMAVNVTGVMLPCREVIRYWLEN-GIKGTIIVNSSVHQ   152
  Seq02  NNAGMDGPRASVGDDDPQVWEKVLAVDLMGPYYCARAAIPRMEKA--KRGVIINITSVHE   149
  Seq03  NNAGIDGKRELVGEDDPDDWEKVIEVNLMGPYYCAREAVKRMKPK--KSGVIINITSVHE   156
  Seq04  NNAGIDGKRVMSWEIDPEDWRKVIDVNMLGSFYCAQQALKRMIPA--SSGVVISVSSVHE   148
  Seq05  NNAGLETRT-SVLDTTPEDYDRVLDVNLKSAFFGTQFAAKQMIKQ-GGGGRIINISSVHE   149
  Seq06  NNAGVEFGE-TLATLTEEKYDLLMNINLKGAVFGSKLAAEQMRKQ-GDGGVIVNITSTHE   156
  Seq07  NNAGVERRA-DFWDVTEEDYDLVMDTNVKGLFFATQAFVRHLRAR-KDEGAIVNISSVHE   150
  Seq08  ANSGVGBLG-DPHEVETEEWDRVLDVNLKGIFLCDKYAVQQMLKQ-GQGGAIVNTGSIHS   146
  Seq09  NNAAIEGALAPTAAYSEEDWDRTINVNLKGTWLCLKYEILHMLQQ--GGGAIVNTASVVG   148
  Seq10  NCAGINIPK-PAERYPLEDWNKVMDANVTGVFLVCREVGKVMVKQ--NGGKIINVSSVRS   174
  Seq11  NNAGITRDT-LMMRMKLQQWQEVIDLNLTGVFLCTQAATKAMGKKKPVSGRIINITSVVG   170
  Seq12  NNAGIYPFK-PFMEMTFNDWYRVINVNLNGVFNVTRAVVPYMVKQ--KNGRIINIASIAG   144
  Seq13  NNAGILEPK-LFEDMKPRDWQRMIEVHFYGALNVAHAAIPYMKRN--GGGVIVNIASVLG   146
  Seq14  NNAGVIKRA-PVTEYSVEDWDKVLNINLKAAFLLSQYFSRYAIEN-GIKARIINVASMLS   151
  Seq15  NNAGLENPV-PSHEMPLKDWDKVISTNLTGAFLGSREAIKYFVEN-DIKGNVINMSSVHE   148
  Tre1Anc NNAGIESPKAPVHEMTPEDWDRVIDVNLKGVFLCTREAVKHMIKQKGKGGRIINISSVHE   180
  Tre2Anc NNAGIESPKAPVHEMTPEDWDRVIDVNLKGVFLCTREAVKHMIKQKGKGGRIINISSVHG   180
  Tre3Anc NNAGIESPKAPVHEMTPEDWDRVIDVNLKGVFLCTREAVKHMIKQKGKGGRIINISSVHE   180
  Tre4Anc NNAGIEGPKAPFHEMTPEDWDRVIDVNLKGVFLCTREAVKHMIKQKGKGGAIINISSVHE   180

*  :*  .:       .      .  .  .     :      : *      :
  Seq01  IIPKP-HYLGYSASKGAVGNIVRTLALEYATRGIRVNAVAPGAIVTPINMSWIDDPEQYK   211
  Seq02  FIPWE-GYSAYTSAKAGLSMFTKTLAQETADKGIRVVAIAPGAIQTPINQSVWSDPQSLK   208
  Seq03  YVPWS-GYTAYSSAKAGLSMFTKALAQELSDYNIRVVAIAPGAIKTPINKDVWGNPESLK   215
  Seq04  EIAWS-GYSAYAASKSGVAMMTKTLAQEAAPYGVRVLAIAPGAIKTAINKPVWSDPEQRK   207
  Seq05  DWPMP-NNTAYCLSKGGVRMLTRTAGVELAPHGITMVNIGPGAVDTPINASYAGNKTLLD   208
  Seq06  DWPMP--SDLAYCISKGGMRMLTRTAGVELGADKIRMVGVGPGAINTPINADDT--PAETT  213
  Seq07  EIAFP-HFASYCASKGALRMLARNLASELAPLGIRVNNVAPGAIATPINAQLMDNPEQLR   209
  Seq08  FVAKQ-GVTAYGAAKGGVAMLTRTLGTSYAAQGIRANFVAPGYIDTPLLAALP--REAYE   203
  Seq09  LVGTI-GLPAYCAAKGGVVQLTKAAALEYAKAGIRINAVCPGATHTPMLNRLMVQPGAET   207
  Seq10  SYGMPKNYIAYCSSKAAVNMITKQLACEWAKYNILVNAIAPTVIATPLTAHIMKDPELSK   234
  Seq11  VTGNA-GQANYSAAKAGVIGLTKTVAREYAGRNIQCNAIAPGFIASDMTAVLG--EELEK   227
  Seq12  AVMGFMGLTHYSASKAGIVGFTRALALELARYGITVNAIAPGAINTPGAATGS--EEQVR   202
  Seq13  LRPEP-EASHYSAAKAALIAWTIAVAKELADYNIRVFAVAPGGVDTDMTRAWG----DMD   201
  Seq14  FQGGIF-TTAYTVSKHGIVGLTRIFANELARYGITVNAIAPGYHETDNTAALRNDRNRSM   210
  Seq15  VIPWP-LFVHYAASKGGIKLMTETLALEYAPKGIRVNNIGPGAINTPINAEKFADPKQRA   207
  Tre1Anc FIPWPMGYTAYCASKAGVAMLTRTLALEYAPYGIRVNAIAPGAINTPINASLMSDPEQLK   240
  Tre2Anc FIGGPMGYTAYCASKGGVVMLTRTLALEYAPYGIRVNAIAPGAINTPMTASLMSDPEQLK   240
  Tre3Anc FIPWPMGYTAYCASKAGVAMLTRTLALELAPYGIRVNAIAPGAINTPINASLMSDPEQLK   240
  Tre4Anc FIPWPMGYTAYCASKAGVAMLTRTLALEYAPYGIRVNAIAPGAINTPINASLMSDPEQLK   240
```

Figure 9

```
              :           . ::        .    ::.      .**
   Seq01  AVSSHIPMKRPGESREIADAITFLAAEDST-YITGQTLYVDGGLTLYGDFENNWSS    266
   Seq02  DLNEKISMGRLGNPEEIGNVAAFLASDLAS-YITGTTLAVDGGMLIYPEFRHGG--     261
   Seq03  DLLNKIAMPRLGEVDDIGQAAVFLASDLAS-YITGTTLLVDGGMALYPDFKHGG--     268
   Seq04  DLLTKIPLNRIGEPKEIAEMTVVLASDVAS-YITGRTIFIDGGMTDYPSFAEGG--     260
   Seq05  KLDAAIPLGRMAEPQEIASVAAFVASDGAS-YITATSIFADGGIMQSSPGL-----     258
   Seq06  ALEKAIPLSYIGSPQEMGKVVCFAASEAAS-YITATTIIADGGLMQKPGAV-----     263
   Seq07  ALNAQIPLGRMGQPEDVAGLVAFLSGDEAR-YITGGTHFVDGGLTYHYTEQ-----     259
   Seq08  ELKKLHPIGRLGRPMEVAKAVTFLASDDAS-NITGTSLLVDGGYTAV---------     249
   Seq09  GMLATIPLGRIGNPEEIAAAVVWLCSDAAS-YVTGHIMVVDGGMIAQ---------     253
   Seq10  TMKSRILLGRWGYPDDLIGAVVFFASDASN-FVTGQILYIDGGVTSWA--------     281
   Seq11  KILTTIPAGRYGQPEEIAGLVKFLAMDPAAAYITGQTLHVDGGMVM----------     273
   Seq12  MMINAIPMGKLGTPEDIASAVAYLASDEAS-YITGALIVIDGGWSIT---------     248
   Seq13  WVEEQIPLRRLAKPEEVAKIVLDAVENP---YVSGDVLTISGGLL-----------     243
   Seq14  EILSRIPMGRWGKPDDLKGAVVFLASSAAD-YVTGTVLAVDGGWLSR---------     256
   Seq15  DVESMIPMGYIGEPEEIAAVAAWLASKEAS-YVTGITLFADGGMTQYPSFQAGRG-     261
   Tre1Anc DLLSKIPMGRLGEPEEIAGVVAFLASDEASAYITGTTLFVDGGMTQYPSFQHGGGS    296
   Tre2Anc ELLSQIPMGRLGEPEEIAGAVAFLASDEASAYITGTTLFVDGGMTAYPSFQHGGGS    296
   Tre3Anc DLLSKIPMGRLGEPEEIAGVVAFLASDEASAYITGTTLFVDGGMTQYPSFQHGGGS    296
   Tre4Anc DLLSKIPMGRLGEPEEIAGVVVFLASDEASAYITGTTLFVDGGMTQYPSFQHGGGS    296
```

US 9,023,608 B2

MODIFIED GLUCOSE DEHYDROGENASE

TECHNICAL FIELD

The present invention relates to a modified glucose dehydrogenase [MAD(P)⁺GDH] in which the thermal stability and/or the resistance to an organic solvent are improved by replacing specific amino acids of glucose dehydrogenase [NAD(P)⁺GDH], which uses nicotinamide adenine dinucleotide or nicotinamide adenine dinucleotide phosphate as a coenzyme, with other amino acids; a gene encoding the amino acid sequence of the enzyme; a recombinant vector comprising the gene; a transformant obtained from the vector; and a method for producing the modified NAD(P)⁺GDH using the transformant.

BACKGROUND ART

Clinical test agents using an enzyme specifically reacting to a specific substrate are used for measuring various internal molecules, and a representative example thereof is a test agent for glucose measurement.

A test agent for glucose measurement uses the property of an enzyme for glucose determination, for example glucose dehydrogenase (GDH), to catalyze the dehydrogenation reaction of glucose, and can determine the glucose concentration in an analysis sample based on this property.

Although as GDH, NAD(P)⁺GDH derived from *Bacillus megaterium* can be also used for example, there is a problem that the thermal stability is extremely low when an inorganic salt does not exist in an excessive amount.

Therefore, an attempt to improve the thermal stability, the pH stability or the specific activity in the absence of an inorganic salt has been made, by producing a mutant of NAD(P)⁺ GDH derived from *Bacillus megaterium* in which specific amino acids are replaced with other amino acids (for example, Patent Documents 1 to 3 and Non-Patent Documents 1 and 2).

In Patent Document 3, it is described that the mutant of NAD(P)⁺GDH derived from *Bacillus megaterium*, in which glutamic acid at residue position 170 is replaced with lysine and glutamine at residue position 252 is replaced with leucine, maintains a relative activity of about 60% even after the treatment at 66° C. for 8 hours in the absence of an inorganic salt.

Regarding NAD(P)⁺GDH derived from *Bacillus subtilis*, which is classified into genus *Bacillus* as *Bacillus megaterium* above, the enzyme has been isolated and its gene has been already identified (for example, Non-Patent Documents 3 and 4), and the enzyme can be also used for the application as a test agent for glucose measurement.

NAD(P)⁺GDH derived from *Bacillus subtilis* above is an enzyme, which shows about 85% homology with NAD(P)⁺ GDH derived from *Bacillus megaterium* (for example, Non-Patent Document 5), and has a high specific activity of 900 U/mg or more in the presence of sodium chloride with a high concentration.

Its thermal stability in the absence of an inorganic salt and the like, however, was not sufficient as NAD(P)⁺GDH derived from *Bacillus megaterium*. Thus, regarding NAD(P)⁺GDH derived from *Bacillus subtilis*, an attempt to improve the thermal stability, the pH stability or the relative activity in the absence of an inorganic salt has been also made, by producing a mutant in which specific amino acids are replaced with other amino acids.

On the other hand, a new application of recent GDH is the reproduction of NAD(P)H. When the reaction of NAD(P)⁺ GDH catalyzing glucose is coupled with a reaction system, which uses NAD(P)H and produces NAD(P), expensive NAD(P)H can be sometimes reproduced; however, the thermal stability of NAD(P)⁺GDH and the like have been a problem also in this case.

Patent Document 4 describes that, in the application for the reproduction of NAD(P)H, a mutant of NAD(P)⁺GDH derived from *Bacillus subtilis*, in which at least one amino acid of isoleucine at residue position 165, proline at residue position 194 and lysine at residue position 204 is replaced with another amino acid and other amino acid(s) is also replaced, has an improved specific activity that is several times higher than that of the wild-type enzyme, and has a remaining activity of 80% or more after the heat treatment at 50° C. for 20 minutes.

Non-Patent Document 6 describes that, also in the application for the reproduction of NAD(P)H, the mutant of NAD (P)⁺GDH derived from *Bacillus subtilis*, in which proline at residue position 45 is replaced with alanine, phenylalanine at residue position 155 is replaced with tyrosine, glutamic acid at residue position 170 is replaced with arginine, valine at residue position 227 is replaced with alanine and glutamine at residue position 252 is replaced with leucine, and other mutants have thermal stability, in which almost no in activation is observed at 65° C. in the presence of 0.3 M sodium chloride, and have specific activities of 100 to 150 U/mg.

Non-Patent Document 7 describes that, also in the application for the reproduction of NAD(P)H, the mutant of NAD (P)⁺GDH derived from *Bacillus subtilis*, in which proline at residue position 45 is replaced with alanine, asparagine at residue position 46 is replaced with glutamic acid, phenylalanine at residue position 155 is replaced with tyrosine, glutamic acid at residue position 170 is replaced with lysine, valine at residue position 227 is replaced with alanine, tryptophan at residue position 230 is replaced with phenylalanine and glutamine at residue position 252 is replaced with leucine, has thermal stability in which almost no deactivation is observed at 65° C., and that its resistance to an organic solvent such as acetone is improved in comparison, with the wild-type enzyme.

Further, another new application of NAD(P)⁺GDH is a biofuel cell. A biofuel cell, in which an oxidoreductase is immobilized as a catalyst on at least one of the negative electrode and the positive electrode, attracts the attention as a next-generation fuel cell, since it can effectively extract electrons from a fuel, which cannot be used with a normal industrial catalyst such as glucose. As described in Patent Document 5 or Patent Document 6 for example, NAD(P)⁺GDH is used as an important enzyme to extract electrons from glucose first at the negative electrode.

PRIOR ART DOCUMENTS

Patent Documents

Patent Document 1: JP-A-2-86779 publication
Patent Document 2: JP-A-4-258293 publication
Patent Document 3: JP-A-2003-310274 publication
Patent Document 4: U.S. Pat. No. 7,816,111 specification
Patent Document 5: JP-A-2004-071559 publication
Patent Document 6: JP-A-2010-219021 publication Non-Patent Documents Non-Patent Document 1: Y, Makino et al. Stability-increasing Mutants of Glucose Dehydrogenase from *Bacillus megaterium* IWG3. J Biol Chem. 1989, 264(11). p 6381-6385.

Non-Patent Document 2: S. H. Baik et al. Significantly enhanced stability of Glucose Dehydrogenase by directed evolution. Appl Microbiol Biotechnol. 2003. 61. p 329-335.

Non-Patent Document 3: Ramaley et al. Glycerol protection and purification of *Bacillus subtilis* glucose dehydrogenase. J Biol Chem. 1983. 258 (20). p 12558-12565.

Non-Patent Document 4: Lampel et al. Characterization of the developmentally regulated *Bacillus subtilis* glucose dehydrogenase gene, J Bacteriol. 1986. 166(1). p 238-243.

Non-Patent Document 5: Fortnagel et al. Sequence homologies of glucose-dehydrogenases of *Bacillus megaterium* and *Bacillus subtilis*. J Theor Biol. 1986. 120(4). p 489-497.

Non-Patent Document 6: Eduardo et al. Development of a Thermostable Glucose Dehydrogenase by a Structure-Guided Consensus Concept, ChemBioChem. 2007. 8. p 2295-2301.

Non-Patent Document 7: Eduardo et al. Thermostable variants constructed via the structure-guided consensus method also show increased stability in salts solutions and homogeneous aqueous-organic media. Protein Engineering, Design&Selection. 2008. 21(11) p 673-680.

SUMMARY OF THE INVENTION

Problems that the Invention is to Solve

As described above, NAD(P)$^+$GDH, which had been used conventionally under relatively mild conditions such as the application as the test agent for glucose measurement, has been recently used in industrial applications in which the conditions such as the heat and the solvent are severer, and thus it is desired to provide a modified NAD(P)$^+$GDH, which is not restricted by the presence of an inorganic salt such as sodium chloride and which can be used stably in a wide temperature range.

However, although various mutants of NAD(P)$^+$GDH have been produced as described above, it was unknown whether these mutant enzymes function stably also in a severe environment of higher than 70° C. in the absence of an inorganic salt, and whether they can be used in industrial applications in which the conditions such as the heat and the solvent are severer. Accordingly, a functional modification such as the further thermal stabilization was necessary in order that NAD(P)$^+$GDH can function in a wide range of heat environment in the absence of an inorganic salt.

Further, as described in Examples below, the present inventors found that the mutant of NAD(P)$^+$GDH derived from *Bacillus megaterium* or NAD(P)$^+$GDH derived from *Bacillus subtilis* including the amino acid replacement at residue position 170 from glutamic acid to lysine and the amino acid replacement at residue position 252 from glutamine to leucine, which are known mutations shown to improve the thermal stability in the presence and absence of an inorganic sail as described in Patent Document 3, Non-Patent Document 6 and Non-Patent Document 7, is not suitable for industrial applications in which conditions such as the heat and the solvent are severer, since the remaining activity after the heat treatment at 70° C. in the absence of an inorganic salt is very low, and the activity is completely lost after the heat treatment at 80° C.

Accordingly, the present invention aims to provide NAD(P)$^+$GDR, which functions stably in a wide temperature range also in the absence of an inorganic salt, and which can be used in industrial applications in which conditions such as the heat and/or the solvent are severer.

More specifically, the present invention aims to provide a modified NAD(P)$^+$GDH, which functions stably also after the heat treatment at 70° C. or higher and has the resistance to an organic solvent such as acetone, while the high specific activity of NAD(P)$^+$GDH in the absence of an inorganic salt is maintained, so that it can be widely used in industrial applications, by a genetic engineering method and the like.

Further, the present invention aims to provide a gene that is necessary for the mass production of the modified NAD(P)$^+$GDH, a recombinant vector comprising the gene, a transformant obtained from the vector, and a method for producing the modified NAD(P)$^+$GDH using the transformant.

Means for Solving the Problems

The present inventors conducted extensive research to solve the above problems, and as a result found that it is possible to produce a modified NAD(P)$^+$GDH in which the heat stability and/or the resistance to an organic solvent in the absence of sodium chloride has been improved in comparison with the conventional mutant enzymes, by replacing specific amino acids of NAD(P)$^+$GDH derived from *Bacillus subtilis* with other amino acids; and the inventors accomplished the present invention.

1. A protein having a glucose dehydrogenase [NAD(P)$^+$GDH] activity using nicotinamide adenine dinucleotide or nicotinamide adenine dinucleotide phosphate as a coenzyme, which comprises the following amino acid sequence of (a) or (b).

(a) An amino acid sequence, wherein glutamic acid at residue position 170 and glutamine at residue position 252 in the amino acid sequence shown in the SEQ ID NO:1 of the sequence listing are replaced with other amino acids, and at least one amino acid selected from the group consisting of glutamine at residue position 31, glycine at residue position 64, lysine at residue position 111, alanine at residue position 159, lysine at residue position 179, tyrosine at residue position 217, isoleucine at residue position 218 and alanine at residue position 246 is replaced with another amino acid (b) An amino acid sequence, wherein one or several amino acids are deleted, replaced or added in the amino acid sequence of (a) at residue positions other than above residue position 170, position 252, position 31, position 64, position 111, position 159, position 179, position 217, position 218 and position 246

2. The protein according to the above item 1, wherein the amino acid sequence of (a) is an amino acid sequence in which the following amino acid replacements of (1) are made and at least one amino acid replacement selected from the group consisting of (2) to (9) is made in the amino acid sequence shown in the SEQ ID NO:1 of the sequence listing.
    (1) E170K+Q252L
    (2) Q31G
    (3) G64A
    (4) K111R
    (5) A159C
    (6) K179Y
    (7) Y217R
    (8) I218L
    (9) A246V 3. The protein according to the above item 1 or 2, wherein the amino acid sequence of (a) is the amino acid sequence shown in any one of the SEQ ID NOs:3, 5, 7, 9, 11, 13, 15, 17, 19, 21, 23, 25, 27, 29, 31, 33, 35, 37, 39 and 41 of the sequence listing.

4. A protein having a NAD(P)⁺GDH activity, which comprises an amino acid sequence in which one or several amino acids are deleted, replaced or added in the amino acid sequence of the protein described in the above item 3 at residue positions other than above residue position 170, position 252, position 31, position 64, position 111, position 159, position 179, position 217, position 218 and position 246.
5. The protein according to any one of the above items 1 to 4, wherein the remaining activity after a heat treatment at 70° C. for 30 minutes in the absence of an inorganic salt is higher than the remaining activity of the protein in which the amino acid replacements of I165M+E170K+P194T+A197K+K204E+K206R+E222D+S237C are made in the amino acid sequence shown in the SEQ ID NO:79 of the sequence listing.
6. The protein according to any one of the above items 1 to 5, wherein the remaining activity after a heat treatment at 70° C. for 30 minutes in the absence of an inorganic salt is 20% or more.
7. The protein according to any one of the above items 1 to 6, wherein the remaining activity after a heat treatment at 80° C. for 30 minutes in the absence of an inorganic salt is 1% or more.
8. The protein according to any one of the above items 1 to 7, wherein the remaining activity after a heat treatment at 84° C. for 30 minutes in the absence of an inorganic salt is 1% or more.
9. The protein according to the above items 1 to 8, wherein the remaining activity after an organic solvent treatment in the absence of an inorganic salt is higher than the remaining activity of the protein in which the amino acid replacements of I165M+E170K+P194T+A197K+K204E+K206R+E222D+S237C are made in the amino acid sequence shown in the SEQ ID NO:79 of the sequence listing.
10. The protein according to any one of the above items 1 to 9, wherein the remaining activity after an organic solvent treatment in the absence of an inorganic salt is higher than the remaining activity after the treatment of the protein comprising the amino acid sequence shown in the SEQ ID NO:1 of the sequence listing.
11. A DNA which encodes the protein described in any one of the above items 1 to 10.
12. The DNA according to the above item 11, wherein the codon usage frequency of the nucleic acid sequence of the DNA is optimized to the codon usage frequency of *Escherichia coli*.
13. A recombinant vector which comprises the DNA described in the above item 11 or the above item 12.
14. A transformant which is obtained from the recombinant vector described in the above item 13.
15. The transformant according to the above item 14, wherein the host is *Escherichia coli*.
16. A method for producing a modified NAD(P)⁺GDH which comprises producing NAD(P)⁺GDH by culturing the transformant described in the above item 14 or the above item 15 and collecting the NAD(P)⁺GDH.
17. A test agent for glucose measurement which comprises the protein described in any one of the above items 1 to 10.
18. A glucose sensor which comprises the protein described in any one of the above items 1 to 10.
19. A method for measuring a glucose concentration which uses the protein described in any one of the above items 1 to 10.

Effects of the Invention

The modified NAD(P)⁺GDH of the present invention comprises an amino acid sequence including specific amino acid replacements in addition to the amino acid replacements of glutamic acid at residue position 170 and glutamine at residue position 252 of NAD(P)⁺GDH derived from *Bacillus subtilis* with other amino acids, and thus functions stably in a wide temperature range and shows remarkably high thermal stability and/or resistance to an organic solvent in comparison with conventional NAD(P)⁺GDH, while it maintains the high specific activity of NAD(P)⁺GDH in the absence of an inorganic salt.

BRIEF DESCRIPTION OF THE DRAWINGS

FIG. 1 is the N-terminal half of the multiple alignment figure including NAD(P)⁺GDH divided into two.
FIG. 2 is the C-terminal half of the multiple alignment figure including NAD(P)⁺GDH divided into two.
FIG. 7 is the N-terminal part of the multiple alignment figure, which includes the estimated ancestor-type amino acid sequence and NAD(P)⁺GDH and which was divided into three.
FIG. 8 is the middle part between the N-terminal and C-terminal of the multiple alignment figure, which includes the estimated ancestor-type amino acid sequence and NAD(P)⁺GDH and which was divided into three.
FIG. 9 is the C-terminal part of the multiple alignment figure, which includes the estimated ancestor-type amino acid sequence and NAD(P)⁺GDH and which was divided into three.

MODES FOR CARRYING OUT THE INVENTION

Figure 3:
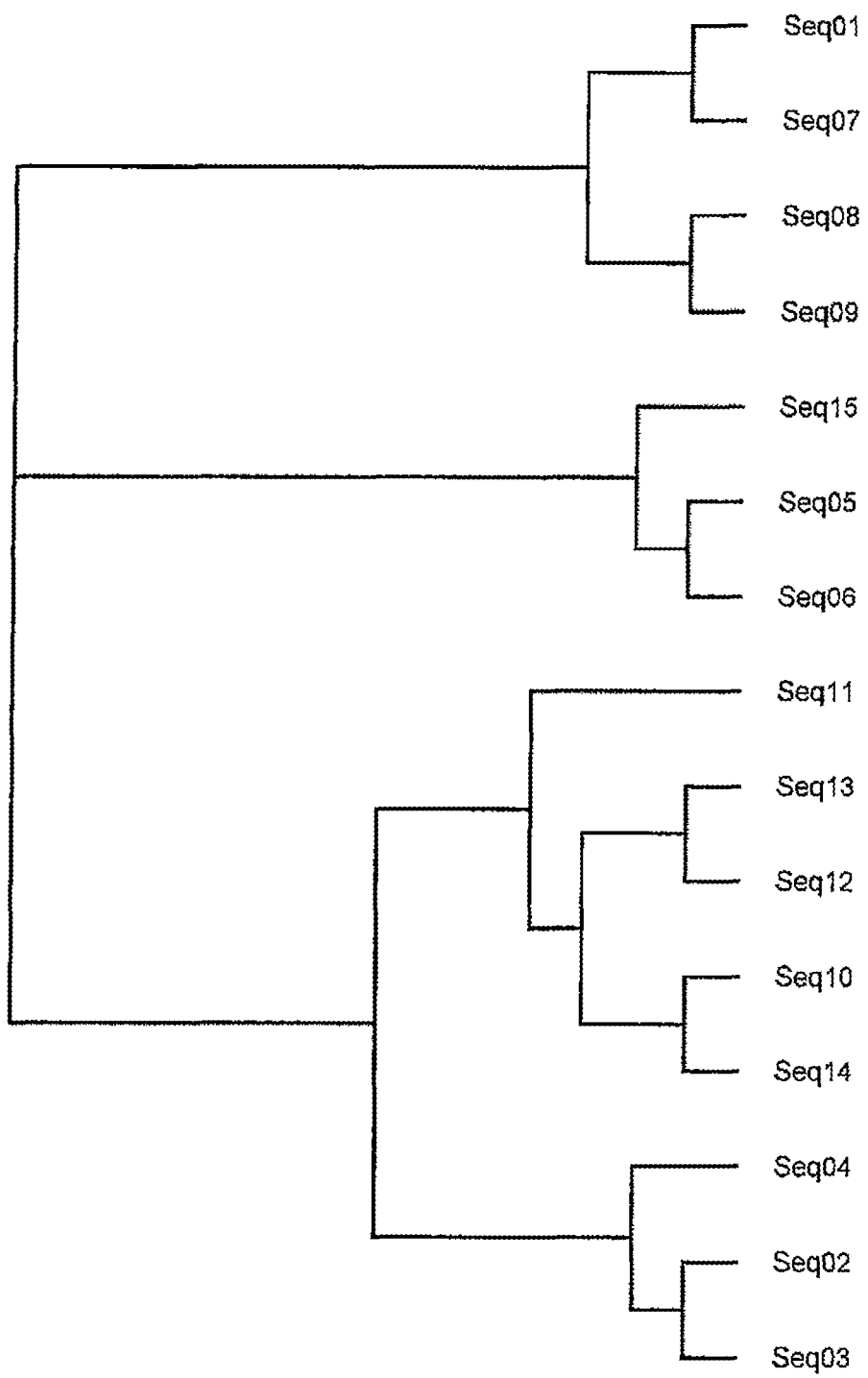
FIG. 3 is a figure of one of the four molecular phylogenetic trees created.
Figure 4:
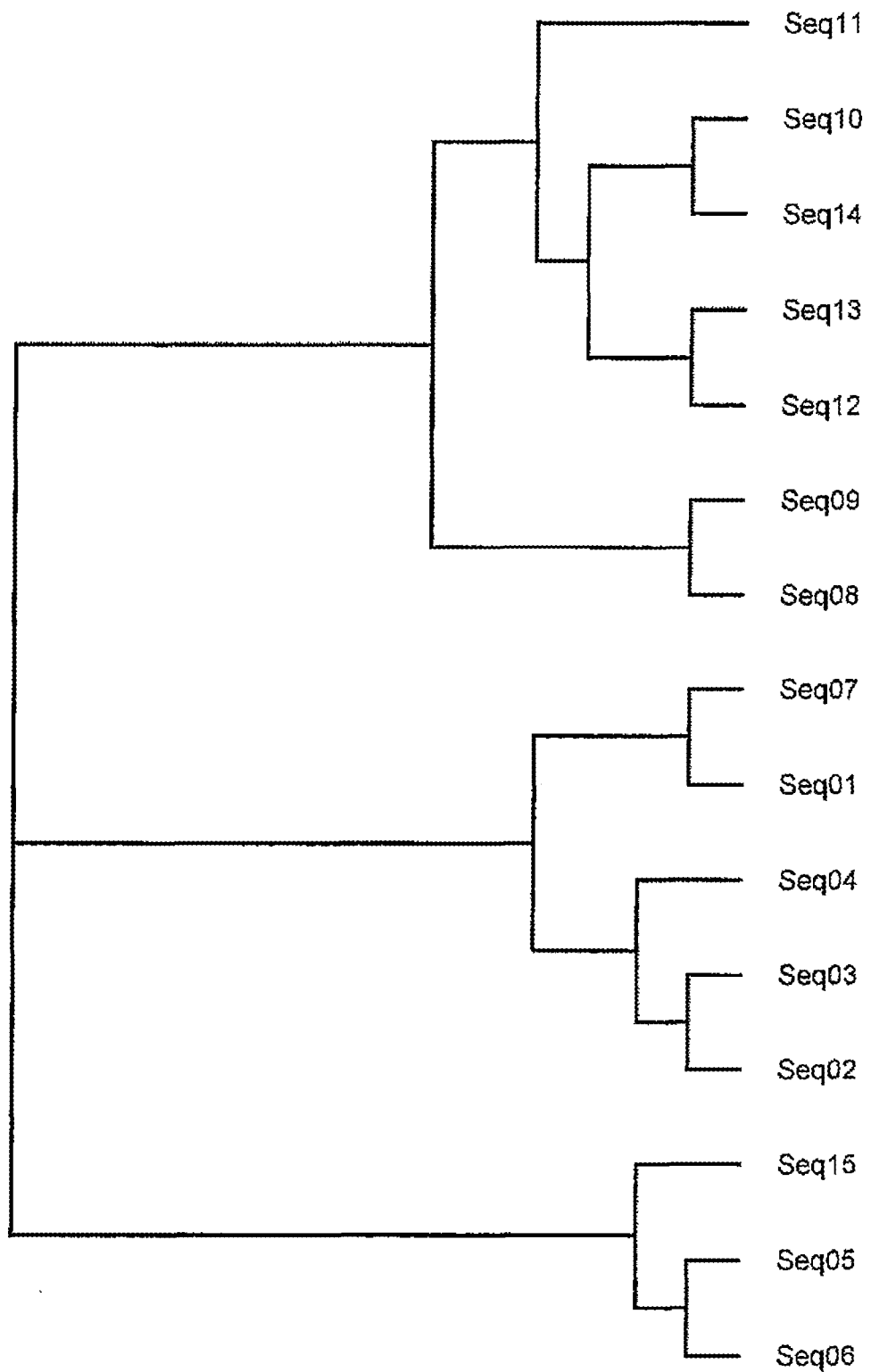
FIG. 4 is a figure of one of the four molecular phylogenetic trees created.

The present invention will be described in detail below.
The 20 amino acid residues in the amino acid sequences in this specification, except for the sequence listing, are described with one-letter abbreviations. That is, glycine (Gly) is G, alanine (Ala) is A, valine (Val) is V, leucine (Leu) is L, isoleucine (Ile) is I, phenylalanine (Phe) is F, tyrosine (Tyr) is Y, tryptophan (Trp) is W, serine (Ser) is S, threonine (Thr) is T, cysteine (Cys) is C, methionine (Met) is M, aspartic acid (Asp) is D, glutamic acid (Glu) is E, asparagine (Asn) is N, glutamine (Gln) is Q, lysine (Lys) is K, arginine (Arg) is R, histidine (His) is H, and proline (Pro) is P.
The expressions such as "A159C" in this specification relate to the notation of amino acid replacements. For example, "A159C" means that the amino acid A at residue position 159 from the N-terminal in a specific amino acid sequence is replaced with the amino acid C.
Further, the expressions such as "Y217R+I218L" in this specification mean that the amino acid replacements of Y217R and I218L are simultaneously introduced to an amino acid sequence.
The modified NAD(P)⁺GDH of the present invention is a protein having the NAD(P)⁺GDH activity, which includes the amino acid sequence of (a) below. The protein is thermally stable at 70° C. or higher in the absence of an inorganic salt.
(a) An amino acid sequence, in which glutamic acid at residue position 170 and glutamine at residue position 252 in the amino acid sequence shown in the SEQ ID NO: 1 of the sequence listing are replaced with other amino acids, and at least one amino acid selected from the group consisting of glutamine at residue position 31, glycine at residue position 64, lysine at residue position 111, alanine at residue position 159, lysine at residue position 179, tyrosine at residue position 217, isoleucine at residue position 218 and alanine at residue position 246 is replaced with another amino acid.

Regarding the other amino acids and the another amino acid above, for example, each amino acid is preferably replaced with the following amino acids.

(i) Glutamic acid at residue position 170: preferably replaced with lysine, arginine or isoleucine, and more preferably replaced with lysine.

(ii) Glutamine at residue position 252: preferably replaced with leucine.

(iii) Glutamine at residue position 31: preferably replaced with glycine or alanine, and more preferably replaced with glycine. Glycine is the ancestor-type amino acid for glutamine at residue position 31, as described below.

(iv) Glycine at residue position 64: preferably replaced with alanine, methionine, leucine or cysteine, and more preferably replaced with alanine. Alanine is the ancestor-type amino acid for glycine at residue position 64, as described below.

(v) Lysine at residue position 111: preferably replaced with arginine, leucine, glycine or glutamic acid, and more preferably replaced with arginine. Arginine is the ancestor-type amino acid for lysine at residue position 111, as described below.

(vi) Alanine at residue position 159: preferably replaced with cysteine, glycine, threonine or serine, and more preferably replaced with cysteine. Cysteine is the ancestor-type amino acid for alanine at residue position 159, as described below.

(vii) Lysine at residue position 179: preferably replaced with tyrosine, arginine, histidine, leucine, glutamine, as aspartic acid or alanine, and more preferably replaced with tyrosine. Tyrosine is the ancestor-type amino acid for lysine at residue position 179, as described below.

(viii) Tyrosine at residue position 217: preferably replaced with arginine, lysine or histidine, and more preferably replaced with arginine. Arginine is the ancestor-type amino acid for tyrosine at residue position 217, as described below.

(ix) Isoleucine at residue position 218: preferably replaced with leucine, tryptophan, tyrosine, methionine, proline or methionine, and more preferably replaced with leucine. Leucine is the ancestor-type amino acid for isoleucine at residue position 218, as described below.

(x) Alanine at residue position 246: preferably replaced with valine or isoleucine, and more preferably replaced with valine. Valine is the ancestor-type amino acid for alanine at residue position 246, as described below.

The modified NAD(P)$^+$GDH including an amino acid sequence, which includes at least one amino acid replacement selected from the group consisting of the following (2) to (9) in addition to the amino acid replacements (1) of glutamic acid at residue position 170 and glutamine at residue position 252 with other amino acids, functions stably in a wide temperature range and shows remarkably high thermal stability and/or resistance to an organic solvent in comparison with conventional NAD(P)$^+$GDH, while the high specific activity of NAD(P)$^+$GDH is maintained in the absence of an inorganic salt.

The amino acid sequence (a) above is preferably an amino acid sequence, in which the amino acid replacements of the following (1) and at least one amino acid replacement selected from the group consisting of (2) to (9) are made in the amino acid sequence shown in the SEQ ID NO: 1 of the sequence Listing.

(1) E170K+Q252L
(2) Q31G
(3) G64A
(4) K111R
(5) A159C
(6) K179Y
(7) Y217R
(8) I218L
(9) A246V

When only the amino acid replacements of (1) E170K+Q252L are made in the amino acid sequence shown in the SEQ ID NO: 1, the mutant obtained has a very low remaining activity after the heat treatment at 70° C. or higher in the absence of an inorganic salt, and the activity is lost after the heat treatment at 80° C. or higher. Thus, the mutant cannot function stably in a wide temperature range.

However, when at least one amino acid replacement selected from the group consisting of (2) to (9) above is made in the amino acid sequence shown in the SEQ ID NO: 1. In addition to the amino acid replacements of (1) E170K+Q252L, the modified NAD(P)$^+$GDH obtained can function stably after the heat treatment at 70° C. or higher and/or have the resistance to an organic solvent such as acetone, while the high specific activity of NAD(P)$^+$GDH is maintained in the absence of an inorganic salt.

In this regard, in order to improve the resistance to an organic solvent in the absence of an inorganic slat, it is particularly preferable that at least, one amino acid replacement selected from the group consisting of (5), (7) and (8) above is made in the amino acid sequence shown in the SEQ ID NO: 1 in addition to the amino acid replacements of (1) E170K+Q252L.

It is more preferable that the amino acid sequence of (a) above is an amino acid sequence, in which the following amino acid replacements are made in the amino acid sequence shown in the SEQ ID NO: 1 of the sequence listing; (1)E170K+Q252L+(5) A159C, the amino acid replacements of (1)E170K+Q252L+(5)A159C+(2)Q31G, the amino acid replacements of (1)E170K+Q252L+(5)A159C+(3)G64A, the amino acid replacements of (1)E170K+Q252L+(5)A159C+(4)K111R, the amino acid replacements of (1)E170K+Q252L+(5)A159C+(6)K179Y, the amino acid replacements of (1)E170K+Q252L+(5)A159C+(9)A246V or the amino acid replacements of (1)E170K+Q252L+(7)Y217R+(8)I218L, the amino acid replacements of (1)E170K+Q252L+(7)Y217R+(8)I218L+(2)Q31G, the amino acid replacements of (1)E170K+Q252L+(7)Y217R+(8)I218L+(3)G64A, the amino acid replacements of (1)E170K+Q252L+(7)Y217R+(8)I218L+(4)K111R, the amino acid replacements of (1)E170K+Q252L+(7)Y217R+(8)I218L+(6)K179Y or the amino acid replacements of (1)E170K+Q252L+(7)Y217R+(8)I218L+(9)A246V: and more preferably an amino acid sequence, in which the following amino acid replacements are made;
(1)E170K+Q252L+(5)A159C+(7)Y217R+(8)I218L, the amino acid replacements of (1)E170K+Q252L+(5)A159C+(7)Y217R+(8)I218L+(2 Q31G, the amino acid replacements of
(1)E170K+Q252L+(5)A159C+(7)Y217R+(8)I218L+(3) G64A, the amino acid replacements of
(1)E170K+Q252L+(5)A159C+(7)Y217R+(8)I218L+(4) K111R, the amino acid replacements of (1)E170+Q252L+(5)A159C+(7)Y217R+(8)I218L+(6)
K179Y, the amino acid replacements of
(1)E170K+Q252L+(5)A159C+(7)Y217R+(8)I218L+(9)
A246V or the amino acid replacements of
(1)E170K+Q252L+(5)A159C+(7)Y217R+(8)I218L+(3)
G64A+(4)K111R or amino acid replacements of
(1)E170K+Q252L+(5)A159C+(7)Y217R+(8)I218L+(2)
Q31G+(3)G64A.

Specific examples of the amino acid sequence of (a) above are the amino acid sequences, each of which is shown in any one of the SEQ ID NOs: 3, 5, 7, 9, 11, 13, 15, 17, 19, 21, 23, 25, 27, 29, 31, 33, 35, 37, 39 and 41 of the sequence listing.

The modified NAD(P)$^+$GDH of the present invention includes a protein having the NAD(P)$^+$GDH activity, which includes the amino acid sequence of following (b). The protein is thermally stable at 70° C. or higher in the absence of an inorganic salt.

(b) An amino acid sequence, in which one or several amino acid is deleted, replaced or added in the amino acid sequence of (a) above at residue positions other than the above residue position 170, position 252, position 31, position 64, position 111, position 159, position 179, position 217, position 218 and position 246.

In the amino acid sequence of (b) above, the number of the amino acid residues to be modified is preferably 1 to 20, more preferably 1 to 10, still more preferably 1 to 6, particularly preferably several (1 to 2 or 3), and most preferably 1.

In this regard, it is known that serine at residue position 145, tyrosine at residue position 158 and lysine at residue position 162 in the amino acid sequence of NAD(P)$^+$GDH, which has been already reported, are necessary for the NAD(P)$^+$GDH activity [Keizo Yamamoto et al. J. Biochem. 129 (2)303-312(2002)]. Accordingly, it is preferable that these amino acids are maintained in the amino acid sequence of (b).

Further, the modified NAD(P)$^+$GDH of the present invention includes a protein having the NAD(P)$^+$GDH activity and being thermally stable at 70° C. or higher in the absence of an inorganic salt, which includes an amino acid sequence showing homology to the amino acid sequence of (a) above. The homology is, for example, preferably 80% or higher, more preferably 90% or higher, still more preferably 95% or higher, and particularly preferably 99% or higher.

Here, the "homology" represents the value of similarity obtained by bl2seq program (Tatiana A. Tatsusova, Thomas L. Madden, FEMS Microbiol. Lett., Vol. 174, 247-250, 1999) of BLAST PACKAGE [sgi32bit edition, Version 2.0.12; available from the National Center for Biotechnology Information [NCBI]]. Examples of the parameter are Gap insertion Cost value: 11, and Gap extension Cost value: 1.

NAD(P)$^+$GDH is glucose dehydrogenase, which uses nicotinamide adenine dinucleotide or nicotinamide adenine dinucleotide phosphate as a coenzyme. NAD(P)$^+$GDH is an enzyme, which couples with the reaction to add hydrogen to the coenzymes and catalyzes the dehydrogenation reaction of β-D-glucose (glucose), and is an enzyme classified in to EC1.1.147.

[Measurement of the NAD(P)$^+$GDH Activity]

In the present invention, the NAD(P)$^+$GDH activity is measured using the following reagents under the following measurement condition.
(Reagents)
100 mM tris-hydrochloric acid buffer pH 8.0
100 mM aqueous NAD(P)$^+$ solution
1 M aqueous D-glucose solution
Reagent for measuring the enzyme activity: The reagent for measuring the enzyme activity is prepared by mixing 17.5 mL of the tris-hydrochloric acid buffer, 0.5 mL of the aqueous NAD(P)$^+$ solution and 2 mL of the aqueous glucose solution above.

Solution for measuring the enzyme activity: The solution for measuring the enzyme activity is prepared by diluting the undiluted solution of the enzyme (also called the "undiluted enzyme solution" below) so that the following activity value becomes 5 to 15 U/mL, using 20 mM potassium phosphate buffer (pH 8.0) as the solution for diluting the enzyme [NAD(P)$^+$GDH] to a desired concentration (also called "the enzyme dilution solution" below).
(Measurement Condition)

To a cell for a spectrophotometer, 0.9 mL of the reagent for measuring the enzyme activity is put, and preincubated at 37° C. for 5 minutes or longer. After adding 0.005 mL of the solution for measuring the enzyme activity and mixing well, the change in the absorbance at 340 nm is recorded for 40 seconds with a spectrophotometer, which has been previously incubated at 37° C., and the change in the absorbance per minute (ΔOD/minute) is calculated. As the blank, water is mixed to the reagent for measuring the enzyme activity instead of the solution for measuring the enzyme activity, and the change in the absorbance per minute (ΔODblank/minute) is calculated as described above. The activity value is calculated from these values by the following formula.

(Formula) Activity (U/mL)=(ΔoD/minute−ΔoDblank/minute)×905×Dilution ratio/(6.22×5×1.0)

In this regard, in the above formula, 905 represents the fluid volume of the reagent for measuring the enzyme activity and the solution for measuring the enzyme activity, 6.22 represents the molecular extinction coefficient (cm$^2$/micromole) of NAD$^+$ under this measurement condition, 5 represents the fluid volume of the solution for measuring the enzyme activity, and 1.0 represents the light path length (cm) of the cell used for measuring the enzyme activity.

[Measurement of the Specific Activity of NAD(P)$^+$GDH]

A specific activity value is a value in which the activity of an enzyme is expressed with the activity value per weight of the protein. In the present invention, the specific activity value of NAD(P)$^+$GDH is measured using the following reagents under the following measurement condition.
(Reagents)
Enzyme dilution solution: 20 mM potassium phosphate buffer (pH 8.0)
Reagent for measuring the enzyme activity: the above reagent for measuring the enzyme activity
(Measurement Condition)

The undiluted enzyme solution is diluted with the enzyme dilution solution if necessary, and the activity is measured by the above method for measuring the activity. The protein concentration of the undiluted enzyme solution is calculated from the absorbance at 280 nm with 1 oD=1 mg/ml.

The activity (U/mL) of the enzyme undiluted solution is calculated by the above formula, and the protein concentration (mg/ml) of the undiluted enzyme solution is calculated. The specific activity is calculated from these values by the following formula.

(Formula) Specific activity (U/mg)=(Activity)/(Protein concentration)

The specific activity (U/mg) of the modified NAD(P)$^+$GDH of the present invention is preferably 500 U/mg-protein or more, more preferably 600 U/mg-protein or more, and still more preferably 800 U/mg-protein or more.

[Thermal Stability in the Absence of an Inorganic Salt]

The modified NAD(P)$^+$GDH of the present invention shows the thermal stability at 70° C. or higher in the absence of an inorganic salt. Here, as the inorganic salt, sodium chloride, sodium hydrogen carbonate, sodium carbonate, sodium percarbonate, sodium phosphate, sodium sulfite, sodium sulfate, sodium thiosulfate, sodium bisulfite, sodium nitrite, sodium nitrate, sodium bromide, sodium iodide, sodium borate and the like are mentioned, and sodium chloride is preferable among them.

The thermal stability of the modified NAD(P)$^+$GDH in the absence of an inorganic salt is evaluated, for example based on the remaining activity ratio measured by the procedures (1) and (2) below.

(1) The solution for measuring the enzyme activity is obtained by diluting the undiluted enzyme solution to a specific concentration with the enzyme dilution solution. The protein concentration of the enzyme in the solution for measuring the enzyme activity is preferably from 1 to 1000 µg/mL. Here, all of the enzyme dilution solution, the undiluted enzyme solution and the solution for measuring the enzyme activity are under the condition that no inorganic salt is included.

(2) Under the condition that no inorganic salt is included, the solution for measuring the enzyme activity is heat treated at a certain temperature for a certain time, and the enzyme activities before and after the heat treatment are measured. The heat treatment time is preferably from 30 minutes to 1 hour. The remaining activity ratio (%) after the heat treatment is calculated with the activity before the heat treatment set as 100.

Specifically, the thermal stability in the absence of an inorganic salt is measured, for example by the method described in Examples below. As described in Examples below, it is preferable that the reagent for measuring the enzyme activity for the enzyme activity measurement does not include sodium chloride, either.

The expression "thermally stable at 70° C. or higher in the absence of an inorganic salt" means that the remaining activity ratio (%) after the heat treatment at 70° C. or higher is 20% or more. The remaining activity of the modified NAD(P)$^+$GDH of the present invention after the heat treatment at 70° C. for 30 minutes is 20% or more, preferably 75% or more, and more preferably 80% or more.

Further, the remaining activity of the modified NAD(P)$^+$GDH of the present, invention after the heat treatment at 80° C. for 30 minutes is preferably 1% or more, preferably 20% or more, and more preferably 60% or more.

Furthermore, the remaining activity of the modified NAD(P)$^+$GDH of the present invention after the heat treatment at 84° C. for 30 minutes is preferably 1% or more, preferably 10% or more, and more preferably 30% or more.

In addition, the remaining activity of the modified NAD(P)$^+$GDH of the present invention after the heat treatment at 70° C. for 30 minutes is preferably higher than that of the protein in which the amino acid replacements of I165M+E170K+P194T+A197K+K204E+K206R+E222D+S237C are made in the amino acid sequence shown in the SEQ ID NO:79 of the sequence listing.

Although three amino acids are different between the amino acid sequence shown in SEQ ID NO: 79 of the sequence listing and the amino acid sequence shown in SEQ ID NO: 1, both amino acid sequences are derived from *Bacillus subtilis* and are substantially identical.

Here, the protein in which the amino acid replacements of I165M+E170K+P194T+A197K+K204E+K206R+E222D+S237C are made in the amino acid sequence shown in the SEQ ID NO: 79 of the sequence listing is the mutant described in the SEQ ID NO: 164 of the specification of U.S. Pat. No. 7,816,111.

The modified NAD(P)$^+$GDH of the present invention preferably has improved thermal stability in the absence of an inorganic salt and at 70° C. or higher, in comparison with NAD(P)$^+$GDH comprising the amino acid sequence shown in the SEQ ID NO: 1 (also called the "wild-type NAD(P)$^+$GDH" below) before the amino acid replacements (also called "before the modification" below).

Further, the modified NAD(P)$^+$GDH of the present invention more preferably has improved thermal stability in the absence of an inorganic salt and at 70° C. or higher, in comparison with the mutant of NAD(P)$^+$GDH including an amino acid sequence in which glutamic acid at residue position 170 and glutamine at residue position 252 in the amino acid sequence shown in the SEQ ID NO: 1 of the sequence listing are replaced with other amino acids.

Furthermore, the modified NAD(P)$^+$GDH of the present invention further preferably has improved thermal stability in the absence of an inorganic salt and at 70° C. or higher, in comparison with the mutant of NAD(P)$^+$GDH including the amino acid sequence in which the amino acid replacements of E170K+Q252L are made in the amino acid sequence shown in the SEQ ID NO: 1 of the sequence listing.

[Resistance to an Organic Solvent, in the Absence of an Inorganic Salt]

The modified NAD(P)$^+$GDH of the present invention is preferably a polypeptide, which has improved resistance to an organic solvent in the absence of an inorganic salt, in comparison with NAD(P)$^+$GDH comprising the amino acid sequence shown in the SEQ ID NO: 1 (also called the "wild-type NAD(P)$^+$GDH" below) before the amino acid replacements (also called "before the modification" below).

Further, the modified NAD(P)$^+$GDH of the present invention preferably has a remaining activity after the organic solvent treatment in the absence of an inorganic salt higher than that of the protein in which the amino acid replacements of I165M+E170K+P194T+A197K+K204E+K206R+E222D+S237C are made in the amino acid sequence shown in the SEQ ID NO: 79 of the sequence listing.

As the inorganic salt above, sodium chloride, sodium hydrogen carbonate, sodium carbonate, sodium percarbonate, sodium phosphate, sodium sulfite, sodium sulfate, sodium thiosulfate, sodium bisulfite, sodium nitrite, sodium, nitrate, sodium bromide, sodium iodide, sodium borate and the like are mentioned, and sodium chloride is preferable among them.

Further, examples of the organic solvent are ethylene glycol, 1,2-propanediol, ethanol, methanol, acetonitrile, acetone and 1,4-dioxane, and acetone is preferable among them.

The resistance to an organic solvent in the absence of an inorganic salt in the present invention is evaluated, for example based on the remaining activity ratio measured in the following procedures (1) to (3).

(1) The solution for measuring the enzyme activity is obtained by diluting the undiluted enzyme solution to a specific concentration with the enzyme dilution solution. Here, all of the enzyme dilution solution, the undiluted enzyme solution and the solution for measuring the enzyme activity are under the condition that no inorganic salt is included. The protein concentration of the enzyme in the solution for measuring the enzyme activity is preferably from 1 to 1000 µg/mL.

(2) Under the condition that no inorganic salt is included, the solution for measuring the enzyme activity is added to the organic solvent and stirred, and then ail the solvent is removed by heat drying. Although the condition for the heat drying varies depending on the type of the organic solvent, in general, the temperature is preferably from 20 to 80° C. and the time is preferably from 5 minutes to 1 hour.

(3) The enzyme after the completion of the drying is suspended to the enzyme dilution solution again, and then the enzyme activities before and after the organic solvent/heat drying are measured. The remaining activity ratio (%) after the organic solvent/heat drying is calculated with the activity value before the organic solvent/heat drying set as 100.

Specifically, the resistance to an organic solvent in the absence of an inorganic salt is measured, for example by the method described in Examples below. As described in Examples below, it is preferable that the reagent for measuring the enzyme activity for the enzyme activity measurement does not include an inorganic salt, either.

The modified NAD(P)$^+$GDH of the present invention more preferably has improved resistance to an organic solvent in the absence of an inorganic salt, in comparison with the mutant of NAD(P)$^+$GDH including an amino acid sequence in which glutamic acid at residue position 170 and glutamine at residue position 252 in the amino acid sequence shown in the SEQ ID NO: 1 of the sequence listing are replaced with other amino acids.

Further, the modified NAD(P)$^+$GDH of the present invention further preferably has improved resistance to an organic solvent in the absence of an inorganic salt, in comparison with the mutant of NAD(P)$^+$GDH including the amino acid sequence in which the amino acid replacements of E170K+Q252L are made in the amino acid sequence shown in the SEQ ID NO: 1 of the sequence listing.

The modified NAD(P)$^+$GDH of the present invention may be a fused protein, which is fused with a foreign protein or peptide. Here, the foreign protein or peptide means a protein or peptide that is exogenous to the modified NAD(P)$^+$GDH of the present invention.

Examples of the foreign protein or peptide above are proteins or peptides used for the protein purification (for example, glutathione S-transferase, maltose binding protein, thioredoxin, cellulose binding domain, streptavidin binding peptide and histidine-tag).

The position in the modified NAD(P)$^+$GDH of the present invention; to which the foreign protein or peptide is bound can be appropriately selected, so that both the modified NAD(P)$^+$ GDH of the present invention and the foreign protein or peptide have their functions or activities.

[Method for Determining the Position for Mutation Introduction in the Wild-type NAD(P)$^+$GDH]

The modified NAD(P)$^+$GDH of the present invention is obtained by introducing amino acid replacements, which are determined using (1) the consensus method based on a multiple alignment figure and (2) the ancestor-type amino acid introduction method based on the phylogenetic method below in combination, but not the random mutagenesis using the generally used evolutionary engineering method, to the amino acid sequence of the wild-type NAD(P)$^+$GDH shown in the SEQ ID NO: 1 of the sequence listing.

(1) Consensus Method Based on a Multiple Alignment Figure

The consensus method based on a multiple alignment figure is a site-specific mutagenesis method for a DNA sequence or an amino acid sequence (a method for site-specifically determining the position in the sequence and the type of the mutation), which originally came into use for the purpose of the functional modification of antibodies and has been also used for the purpose of improving the thermal stability of enzymes. The details are described in B. Steipe, et al., J. Mol. Biol. 240, 188-192, 1994.

As the material for the consensus method based on a multiple alignment figure, a figure, in which amino acid sequences obtained by the homology search of a known amino acid sequence in a known database are multiply-aligned using a known alignment program and the like, is used. All the loci in the multiple alignment figure are aligned by a computer program, so that the number of the insertions, deletions, replacements or the like become minimal.

For example, when a candidate protein does not have an activity due to a deletion and the like in the amino acid sequence, the situation observed is that a specific locus is deleted from the amino acid sequence of the candidate protein and certain amino acids are placed in the amino acid sequences other than that of the candidate gene. Regarding the locus, when methionine (M) is mostly placed as the amino acid residues of the sequences other than the candidate protein, M is inserted to the deleted locus. Similarly, when serine (S) is mostly placed, S is inserted to the deleted locus. Such a mutagenesis method by the majority decision is called the consensus method.

The consensus method can be used for the modification or the improvement of various properties of an enzyme. On the other hand, however, the consensus method cannot be always considered to be a method to improve the thermal stability of NAD(P)$^+$GDH in the absence of an inorganic salt, when it is used alone. The present inventors found that it is possible to obtain a modified NAD(P)$^+$GDH having improved thermal stability in the absence of an inorganic salt, using the consensus method and the ancestor-type amino acid introduction method based on the phylogenetic method shown below in combination.

(2) Ancestor-type Amino Acid Introduction Method Based on Phylogenetic Method

The ancestor-type amino acid introduction method based on the phylogenetic method is a method, which was developed for the purpose of speculating the enzyme function of the common ancestor, by estimating the amino acid sequence of the common ancestor of some biological species regarding a specific enzyme, and introducing a part of all of the amino acid sequence of the common ancestor to the original enzyme as mutations.

In general, the enzyme of the common ancestor is shown to be more thermally stable than the original enzyme, which supports the hypothesis that the common ancestor of all organisms is a hyperthermophile, and it relates to the method used for the functional modification of an industrial enzyme as the application in the present invention. The details are described in Hisako, I., et al., FEMS Microbiology Letters 243, 393-398, 2005; Keiko, W., et al., FEBS Letters, 580, 3867-3871, 2006; JP-A-2002-247991 publication; and JP-A-2011-139677 publication.

When the amino acid sequence of the common ancestor is estimated in the ancestor-type amino acid introduction method: in addition to the homologous amino acid sequences obtained by the homology search of the amino acid sequence of a specific candidate gene in a known database, which are also used in the consensus method above, and their multiple alignment figure a molecular phylogenetic tree (also called a phylogenetic tree below) created based on the group of these homologous amino acid sequences, algorithm to create the phylogenetic tree and the multiple alignment figure are used as the materials.

As the algorithm to create a phylogenetic tree, the algorithm based on the maximum parsimony principle is known for example, and a computer program to achieve it can be also used or available. For example, various programs for estimating a phylogenetic tree, such as TREE PUZZLE, MOLPHY and PHYLIP can be used.

In addition, for example, algorithm based on the maximum likelihood principle and the like are known, and a computer program to achieve it can be also used or available. For example, various programs for estimating a phylogenetic tree, such as ModelTest, PHYML, PHYLIP and TreeFinder can be used. A phylogenetic tree can be created using them, but a phylogenetic tree that has been already published can be more easily used.

In such a phylogenetic tree, biological species that are molecular evolutionary close to each other are closely located in the phylogenetic tree. Further, a biological species that is located close to the root of a phylogenetic tree is thought to be closer to the ancestor.

After the multiple alignment result is obtained based on homologous amino acid sequences data, which is obtained by the homology search of the amino acid sequence of a specific enzyme in a database, using an appropriate program, the amino acid sequence of the ancestor-type enzyme in a specific phylogenetic tree can be estimated.

In the present invention, the maximum likelihood method (Masatoshi Nei, "Molecular Evolutionary Genetics", Baifukan Co., Ltd; and Masatoshi Nei and S. Kumar, "Molecular Evolution and Phylogenetics", Baifukan Co., Ltd) was specifically used for estimating the amino acid sequence of the ancestor-type enzyme.

The maximum likelihood method, which can be used in the present invention, is a method to estimate all ancestor-type amino acid sequences on a specific position of the tree (mainly the position corresponding to the root of the phylogenetic tree) based on the predetermined tree form of the phylogenetic tree and the amino acid replacement model, and select the sequence with the highest likelihood as the most likely ancestor-type amino acid sequence. Further, it is also possible to use the program PAML and the like, which are for estimating the ancestor-type from a phylogenetic tree and a multiple alignment of amino acid sequences based on the maximum likelihood method.

Using the phylogenetic tree obtained, the ancestor-type amino acid for each position of the multiply aligned amino acid residues can be determined. As such, the ancestor-type amino acid residue is estimated for each residue of the multiply aligned sequences, and as a result, the ancestor-type amino acid sequence of the corresponding region can be estimated.

In this case, when the biological species used for estimating the ancestor-type amino acid sequence are changed, the tree form of the phylogenetic tree changes and different ancestor-type amino acids are sometimes obtained correspondingly. The positions and kinds thereof depend on the amino acid sequences used for the comparison.

Accordingly, it can be considered to use the amino acid residues at loci, at which such change is less likely, for modification. Such amino acid residues can be determined: by estimating the degree of the tree form change when the amino acid sequence information used for creating the phylogenetic tree is changed, for example, the biological species used for creating the phylogenetic tree are changed or only a part of the amino acid sequence information used for the phylogenetic tree creation is changed without changing the biological species; and by selecting the residues, which have smaller effect on the tree form.

When the ancestor-type amino acid residues are determined as described above, the enzyme analyzed can be modified by replacing at least one non-ancestor-type amino acid residue with the ancestor-type amino acid residue.

By introducing amino acid replacements, which are decided using (2) the ancestor-type amino acid introduction method based on the phylogenetic method in combination with (1) the consensus method based on a multiple alignment figure, to the wild-type amino acid sequence as described above; it is possible to obtain a modified NAD(P)$^+$GDH, in which the thermal stability and/or the resistant to an organic solvent in the absence of an inorganic salt are improved remarkably in comparison with the conventional NAD(P)$^+$GDH.

It is considered, that, by using the method (2) above in combination with the method (1) above, it is possible to introduce specific mutations different from the known mutations, that is, the amino acid mutations of the common ancestor of all organisms, which is said to be a hyperthermophile, into the amino acid sequence of the wild-type NAD(P)$^+$GDH effectively, and thus, the thermal stability and/or the resistance to an organic solvent of the modified NAD(P)$^+$GDH obtained in the absence of an inorganic salt are improved.

The DNA encoding the modified NAD(P)$^+$GDH of the present invention, the recombinant vector including the DNA, the transformant in which the vector is introduced, and the method for producing the modified NAD(P)$^+$GDH using the transformant are explained below.

[DNA Encoding the Modified NAD(P)$^+$GDH]

The DNA encoding the modified NAD (P)$^+$GDH of the present invention can be obtained by introducing mutations to the DNA of the wild-type NAD(P)$^+$GDH before the modification, so that the above amino acid replacements are introduced.

The DNA of the wild-type NAD(P)$^+$GDH above or the DNA of the modified NAD(P)$^+$GDH can be artificially synthesized by the total synthesis method of a gene. In this regard, it is possible to artificially synthesize the DMA, in which the codon usage frequency of the nucleic acid sequence of the DNA is optimized to the codon usage frequency of *Escherichia coli* as described below.

Here, the DNA of the wild-type NAD(P)$^+$GDH can be isolated by the usual method using PGR from *Bacillus subtilis* NBRC3134 strain for example, when it is the known DNA of the nucleic acid sequence shown in the SEQ ID NO: 2 of the sequence listing.

As the method for introducing a specific mutation to a specific position, it is possible to use the DNA site-specific mutagenesis method and the like, for which a kit and the like are widely sold and which are easily available for one skilled in the art. Examples of the specific method for substituting a base in DNA include the use of a commercially available kit (QuickChange Lightning Site-Directed Mutagenesis kit: manufactured by Stratagene, KOD-Plus-Mutagenesis kit: manufactured by Toyobo Co., Ltd. and the like).

The nucleic acid sequence of the DNA thus obtained can be confirmed using a DNA sequencer. Regarding the nucleic acid sequence obtained, the encoding region of NAD(P)$^+$GDH gene in the DNA can be determined by the analysis with a soft for analyzing nucleic acid sequences, such as DNASIS (manufactured by Hitachi Software Engineering Co., Ltd.) and GENETYX (manufactured by Genetyx Corporation).

Once the nucleic acid sequence is determined, the gene encoding the modified NAD(P)$^+$GDH of the present invention can be then obtained by the chemical synthesis, PCR using a closed probe as a template, or hybridization using a DNA fragment including the nucleic acid sequence as a probe.

Further, a mutant-type of the gene encoding the modified NAD(P)$^+$GDH of the present invention, which has the same function as that before the mutation can be synthesized by a site-specific mutagenesis inducing method and the like. In this regard, in order to introduce a mutation to the gene encoding the modified NAD(P)⁺GDH of the present invention, it is possible to adopt known methods, such as Kunkel method, Gapped duplex method or megaprimer PGR method, or methods in accordance therewith.

The DNA of the present invention is DNA encoding the modified NAD(P)⁺GDH of the present invention or the fused protein described above. Examples of the nucleic acid sequence of the DNA encoding the modified NAD(P)⁺GDH of the present invention are the sequences shown in the SEQ ID NOs: 4, 6, 8, 10, 12, 14, 16, 18, 20, 22, 24, 26, 28, 30, 32, 34, 36, 38, 40 and 42 in the sequence listing.

When DNA encoding a fused protein, in which the DNA encoding the modified NAD(P)⁺GDH of the present invention and DNA encoding a foreign protein or peptide are ligated, is prepared; DNA, in which the DNA encoding the foreign protein or peptide is ligated to the DNA encoding the modified NAD(P)⁺GDH of the present invention, is prepared.

The above DNA may be the ligated DNA itself, or a vector including the DNA and the like. As the method for ligating DNA encoding the foreign protein or peptide to the DNA encoding the modified NAD(P)⁺GDH of the present invention, a method for cleaving the gene encoding the modified DNAD(P)⁺GDH of the present invention and the DNA encoding the foreign protein or peptide, both of which have been purified, with an appropriate restriction enzyme, and ligating them, is adopted.

Further, it may be a method for incorporating homologous regions in a part of the DNA encoding the modified NAD(P)⁺GDH of the present invention and a part of the DNA encoding the foreign protein or peptide, and then ligating them by an in vitro method using PCR and the like or an in vivo method using a yeast and the like.

The DNA encoding the modified NAD(P)⁺GDH of the present invention also includes DNA: which is obtained by conducting a mutagenesis treatment to the DNA or cells having the DNA, and selecting, from the DNA or the cells, DNA which hybridizes with the DNA comprising a nucleic acid sequence shown in at least one of the SEQ ID NOs: 4, 6, 8, 10, 12, 14, 16, 18, 20, 22, 24, 26, 28, 30, 32, 34, 36, 38, 40 and 42 of the sequence listing under a stringent condition; and which encodes a polypeptide having the GDH activity.

Although the "stringent condition" here means a condition in which a so-called specific hybrid is formed, a non-specific hybrid is not formed. Although it is difficult to clearly quantify this condition, a condition, in which nucleic acids having a high homology, for example DNA having at least 70 to 90% homology, hybridize with each other, and nucleic acids having a lower homology do not hybridize with each other, is exemplified.

Further, the "under a stringent condition" means the following condition. Namely, it means a condition of incubating at 50° C. to 65° C. for 4 hours to overnight, in 6×SSC (1×SSC is 0.15 M NaCl, 0.015 M sodium citrate, pH 7.0) including 0.5% SDS, 5× Denhartz solution (Denhartz's, 0.1% bovine serum albumin (BSA), 0.1% polyvinylpyrrolidone and 0.1% Ficoll 400) and 100 µg/ml salmon sperm DNA.

The hybridization can be conducted under the stringent condition described above. For example, a nylon membrane, on which a DNA library or a cDNA library encoding the modified NAD(P)⁺GDH of the present invention is fixed, is prepared, and the nylon membrane is blocked at 65° C. in a prehybridization solution including 6×SSC, 0.5% SDS, 5× Denhartz solution and 100 µg/ml salmon sperm DNA. Then, each probe labeled with 32P is added, and it is incubated at 65° C. overnight. After washing this nylon membrane at room temperature for 10 minutes in 6×SSC, at room temperature for 10 minutes in 2×SSC including 0.1% SDS, and at 45° C. for 30 minutes in 0.2×SSC including 0.1% SDS, autoradiography is conducted, and the DNA, which specifically hybridizes with the probe, can be detected. Further, by changing the condition such as washing, genes showing various homologies can be obtained.

In addition, the DNA encoding the modified NAD(P)⁺GDH of the present invention includes DNA, which has homology to the DNA and encodes a polypeptide having the NAD(P)⁺GDH activity. The homology is at least 80% or more, a gene having 90% homology or more is preferable, more preferably 95% or more, and still further preferably 98% or more.

Here, the "homology" of DNA is the value of similarity obtained by b12seq program (Tatiana A. Tatsusova, Thomas L. Madden, FEMS Microbiol. Lett., Vol. 174, 247-250, 1999) of BLAST PACKAGE [sgi32bit edition, Version 2.0.12; available from the National Center for Biotechnology Information (NCBI)]. Examples of the parameter are Gap insertion Cost value: 11and Gap extension Cost value: 1.

The DNA encoding the modified NAD(P)⁺GDH of the present, invention is preferably DMA, in which the codon usage frequency is optimized for the host, and more preferably DNA, in which the codon usage frequency is optimized for *Escherichia coli*.

As an index representing the codon usage frequency, the total value of the host-optimal codon usage frequency for each codon is used. The optimal codon is defined as the codon having the highest, frequency among the codons corresponding to the same amino acid. The codon usage is not particularly limited as long as it is optimized for the host, and an example for the codon usage of *Escherichia coli* is as follows.

F: phenylalanine (ttt), L: leucine (ctg), I: isoleucine (att), M: methionine (atg), V: valine (gtg), Y: tyrosine (tat), stop codon (taa), H: histidine (cat), Q: glutamine (cag), N: asparagine (aat), K: lysine (aaa), D: aspartic acid (gat), E: glutamic acid (gaa), S: serine (agc), P; proline (ccg), T: threonine (acc), A: alanine (gcg), C: cysteine (tgc), W: tryptophan (tgg), R: arginine (cgc), and G: glycine (ggc).

[Recombinant Vector]

The recombinant vector including the DNA encoding the modified NAD(P)⁺GDH of the present invention (called the recombinant vector of the present invention below) can be obtained by inserting the DNA encoding the modified NAD (P)⁺GDH of the present invention to an expression vector.

As the expression vector here, an expression vector, which is developed for the gene recombination from a phage or a plasmid being able to replicate autonomously in the host, is appropriate.

Examples of the phage are Lambda gt10 and Lambda gt11, when *Escherichia coli* is the host.

On the other hand, examples of the plasmid are pBR322, pUC18, pUC118, pUC19, pUC119, pTrc99A, pBluescript and Super Cos I which is a cosmid, when *Escherichia coli* is the host.

When *Pseudomonas* is used, for example, RSF1010, pBBR122, pCN51 and the like, which are broad-host-range vectors for Gram-negative bacteria, are mentioned. Further, for example, animal viruses such as retrovirus and vaccinia virus, insect virus vectors such as baculovirus, and the like are mentioned.

The host is not particularly limited, as long as the recombinant vector is stable and the host can replicate autonomously and express the characters of a foreign gene, and examples thereof are bacteria belonging to genus *Escherichia* such as *Escherichia coli*, genus *Bacillus* such as *Bacillus subtilis* and genus *Pseudomonas* such as *Pseudomonas putida*, yeast, animal cells such as COS cells, insect cells such as Sf9, whole plant bodies belonging to family Brassicaceae, plant organs (for example, leaves, petals, stems, roots and seeds), plant tissues (for example, epidermis, phloems, parenchyma, xylem and bundles) and plant culture cells. *Escherichia coli* is preferable among them, and *Escherichia coli* DH5α and *Escherichia coli* XL-1 Blue MR are more preferable.

The method for inserting the DNA of the present invention to the vector can be conducted in accordance with the method for ligating the gene encoding the foreign protein or peptide to the gene encoding the modified NAD(P)$^+$GDH of the present invention described above.

The method for transfecting a bacterium with the recombinant vector of the present invention and the like is not particularly limited, as long as it is a method for introducing DNA to a bacterium. Examples thereof are a method using competent cells by the calcium ion treatment and the electroporation method.

The method for transfecting yeast with the recombinant, vector of the present, invention and the like is not particularly limited, as long as it is a method for introducing DNA to yeast. Examples thereof are the electroporation method, the spheroplast method and the lithium acetate method.

The method for transfecting an animal cell with the recombinant vector of the present invention and the like is not particularly limited, as long as it is a method for introducing DNA to an animal cell. Examples thereof are the electroporation method, the calcium phosphate method and the lipofection method.

The method for transfecting an insect, cell with the recombinant vector of the present invention and the like is not particularly limited, as long as it is a method for introducing DNA to an insect cell. Examples thereof are the calcium phosphate method, the lipofection method and the electroporation method.

The method for transfecting a plant, with the recombinant vector of the present invention and the like is not particularly limited, as long as it is a method for introducing DNA to a plant. Examples thereof are the electroporation method, the *Agrobacterium* method, the particle gun method and the PEG method.

Examples of the method to check whether the recombinant vector of the present invention and the like is inserted in the host or not are PGR method, Southern hybridization method and Northern hybridization method.

In the case of PGR method, for example, the recombinant vector is isolated and purified from the transformant.

The isolation and purification of the recombinant vector are conducted based on the lysate obtained by the bacteriolysis, for example when the host is a bacterium. As the method for the bacteriolysis, for example the treatment by a bacteriolytic enzyme such as lysozyme is conducted, and if necessary, protease and other enzymes, and a surfactant, such as sodium lauryl sulfate (SLS) are used in combination.

Further, a physical homogenizing method such as freeze-thawing and the French press treatment can be combined. The isolation and purification of the DNA from the lysate can be conducted, for example by appropriately combining the deproteinization treatment by the phenol, treatment and the protease treatment, the ribonuclease treatment, the alcohol precipitation treatment and a commercially available kit.

The cleavage of the DNA can be conducted in accordance with a normal method, for example using the restriction enzyme treatment. Examples of the restriction enzyme are type II restriction enzymes, which act on a specific nucleotide sequence. The ligation of the DNA and the expression vector can be conducted, for example using DNA ligase.

Then, primers specific to the DNA of the present, invention are designed and PGR is conducted using the isolated and purified DNA as a template. It is confirmed that the host is transformed by: conducting agarose gel electrophoresis, polyacrylamide gel electrophoresis, capillary electrophoresis or the like regarding the amplified product obtained by PCR; dyeing with ethidium bromide, SYBR Green solution or the like; and detecting the amplified product as a band.

Further, the amplified product can be detected by conducting PCR using primers, which have been previously labeled with a fluorescent dye and the like. Furthermore, it is also possible to adopt a method to fix the amplified product to the solid phase of a microplate or the like, and confirm the amplified product by fluorescent, enzyme reactions and the like.

[Transformant]

The transformant of the present invention can be obtained by introducing a marker to the recombinant vector, and transfecting the host with the recombinant vector. By screening from the transformant with the expressions of the recombinant vector's marker and the enzyme activity as indexes, the gene donor bacterium having the recombinant vector, which includes the gene encoding the modified NAD(P)$^+$GDH, is obtained.

The nucleic acid sequence of the gene encoding the modified NAD(P)$^+$GDH can be determined by a conventionally known method, for example the dideoxy method. The amino acid sequence of the modified NAD(P)$^+$GDH can be supposed from the nucleic acid sequence determined by this method.

Regarding the culture form of the transformant, the culture condition can be selected considering the nutritional physiological property of the host, and a liquid culture is preferably conducted. It is industrially advantageous to conduct the aeration spinner culture.

As the nutritional source of the medium, those generally used for culturing bacteria can be used. The carbon source can be a carbon compound that can be used as a source, and examples thereof are glucose, sucrose, lactose, maltose, molasses and pyruvic acid.

The nitrogen, source can be a nitrogen compound that can be used as a source, and examples thereof include peptone, meat extract, yeast extract, casein hydrolysate and alkali extract of soybean cake.

In addition, for example, salts such as a phosphate, a carbonate, a sulfate, magnesium, calcium, potassium, iron, manganese and zinc, a specific amino acid, a specific vitamin and the like can be used, if necessary.

The culture temperature can be appropriately changed in the range in which the host grows and the host produces the modified NAD(P)$^+$GDH, and is preferably around 15 to 37° C. The cultivation can be completed at an appropriate moment, waiting for the time at which the yield of the modified NAD(P)$^+$GDH reaches the highest, and the cultivation time is generally about 12 to 48 hours.

The pH of the medium can be appropriately changed in the range in which the host grows and the host produces the modified NAD(P)$^+$GDH, and the pH is preferably within the range of about 5.0 to 9.0.

The water-soluble fraction of the modified NAD(P)$^+$GDH can be obtained by: culturing the transformant, recovering the culture supernatant or the bacteria from the culture medium by a method such as centrifugation, treating the bacteria with a mechanical method such as ultrasound or French press or with a bacteriolytic enzyme such as lysozyme, and solubilizing using protease and other enzymes, and a surfactant such as sodium lauryl sulfate (SDS) in combination, if necessary.

Further, by selecting appropriate expression vector and host, the modified NAD(P)⁺GDH expressed can be secreted into the culture medium.

The method for purifying the enzyme from the water-soluble fraction including the modified NAD(P)⁺GDH obtained as described above can be conducted directly with the water-soluble fraction, and can also be conducted after the modified NAD(P)⁺GDR in the water-soluble fraction is concentrated.

The concentration can be conducted, for example by the vacuum concentration, the membrane concentration, the salting-out treatment, and the fractional precipitation by a hydrophilic organic solvent (for example, methanol, ethanol and acetone). For concentrating the modified NAD(P)⁺GDH, the heat treatment and the isoelectric treatment are also effective purification means.

The purification of the concentrated solution can be conducted by appropriately combining methods such as gel filtration, adsorption chromatography, ion exchange chromatography and affinity chromatography.

The above methods are already known, and can be proceeded making reference to appropriate literatures, magazines, textbooks and the like. Thus obtained purified enzyme can be made into a powder, for example by freeze-drying, vacuum-drying or spray-drying and distributed commercially.

EXAMPLES

Example 1

Determination of Mutagenesis Position of NAD(P)⁺GDH (1-1) Obtaining NAD(P)⁺GDH Homologous Amino Acid Sequence Information Homology search was conducted by the Basic Local Alignment Search Tool (Blast) provided by National Center for Biotechnology Information (NCBI) using the amino acid sequence of NAD(P)⁺GDH derived from *Bacillus subtilis* shown in the SEQ ID NO: 1 of the sequence listing, and the amino acid sequence information derived from various biological species was obtained.

Specifically, the amino acid sequence information of NAD(P)-dependent glucose 1-dehydrogenase (Seq01, YP_192407, *Gluconobacter oxydans* 621H), glucose 1-dehydrogenase putavive (Seq02, YP_002426623, *Acidithiobacillus ferrooxidans* ATCC 23270), glucose 1-dehydrogenase (Seq03, NP_393669, *Thermoplasma acidophilum* DSM 1728), probable glucose 1-dehydrogenase (Seq04, ZP_01092744, *Blastopirellula marina* DSM 3645), glucose 1-dehydrogenase (Seq05, YP_001228184, *Synechococcus* sp. RCC307), 3-oxoacyl-reductase (Seq06, ZP_00995731, *Janibacter* sp. HTCC2649), short-chain dehydrogenase/reductase SDR (Seq07, YP_969459, *Acidovorax avenae* subsp. *citrulli* AAC00-1), short-chain dehydrogenase/reductase SDR (Seq08, YP_001046841, *Methanoculleus marisnigri* JR1), short-chain dehydrogenase/reductase SDR (Seq09, YP_002462956, *Chloroflexus aggregans* DSM 9485), 2-deoxy-D-gluconate 3-dehydrogenase (Seq10, NP_070035, *Archaeoglobus fulgidus* DSM 4304), predicted protein (Seq11, XP_001415472, *Ostreococcus lucimarinus* CCE9901), short-chain dehydrogenase/reductase SDR (Seq12, YP_001541201, *Caldivirga maguilingensis* IC-167), short chain dehydrogenase (Seq13, YP_001012508, *Hyperthermus butylicus* DSM 5456), and 2-deoxy-D-gluconate 3-dehydrogenase (Seq14, YP_001470653, *Thermotoga lettingae* TMO) was obtained.

Further, in addition to the sequence information, the amino acid sequence of NAD(P)⁺GDH derived from *Bacillus subtilis* of the SEQ ID NO: 1 (Seq15) was added.

Here, Seq—indicates the SEQ ID NO: of the amino acid sequence shown in FIG. 1, FIG. 2 or the like described below, and the letter string between them (for example, YP_192407 and the like) indicates the accession number of each amino acid sequence registered in the database. Further, after the letter string, the species name and the strain name are indicated.

(1-2) Drawing Multiple Alignment Figure Including NAD(P)⁺GDH

The amino acid sequence data registered in the database above was aligned with ClustalW and the alignment figure (FIG. 3 and FIG. 2) and the data file were obtained. The data obtained was used for creating molecular phylogenetic trees described below.

(1-3) Creating Molecular Phylogenetic Tree

Using the data of the multiple alignment figure including NAD(P)⁺GDH, four molecular phylogenetic trees were created by the maximum likelihood method using a known computer program. The WAG+G model was used as the molecular replacement model. The four molecular phylogenetic trees are shown in FIG. 3 to FIG. 6.

(1-4) Estimating Ancestor-type Amino Acid Sequence

Using a known computer program, the data of the multiple alignment figure including NAD(P)⁺GDH, and the four molecular phylogenetic trees described above, the ancestor-type amino acid sequences at the roots of the four molecular phylogenetic trees were calculated by the maximum likelihood method. The WAG model was used as the molecular replacement model.

Specifically, the amino acid sequence shown in the SEQ ID NO: 49 is the estimated ancestor-type amino acid sequence at the root of the phylogenetic tree of FIG. 3. The amino acid sequence shown in the SEQ ID NO: 50 is the estimated ancestor-type amino acid sequence at the root of the phylogenetic tree of FIG. 4. The amino acid sequence shown in the SEQ ID NO: 51 is the estimated ancestor-type amino acid sequence at the root of the phylogenetic tree of FIG. 5. The amino acid sequence shown in the SEQ ID NO: 52 is the estimated ancestor-type amino acid sequence at the root of the phylogenetic tree of FIG. 6.

(1-5) Drawing Multiple Alignment Figure Including Estimated Ancestor-type Amino Acid Sequences and NAD(P)⁺GDH, and Determining Introduction Position of Estimated Ancestor-type Amino Acids The ancestor-type amino acid sequences estimated from the four molecular phylogenetic trees were added to the multiple alignment figure shown in FIG. 1 and FIG. 2. The multiple alignment figure obtained including the estimated ancestor-type amino acid sequences and NAD(P)⁺GDH is divided and shown in FIG. 7 to FIG. 9.

In FIG. 7 to FIG. 9, the amino acid sequence indicated with Tre1Anc is the estimated ancestor-type amino acid sequence at the root of the phylogenetic tree of FIG. 3. The amino acid sequence indicated with Tre2Anc is the estimated ancestor-type amino acid sequence at the root of the phylogenetic tree of FIG. 4.

Figure 5:
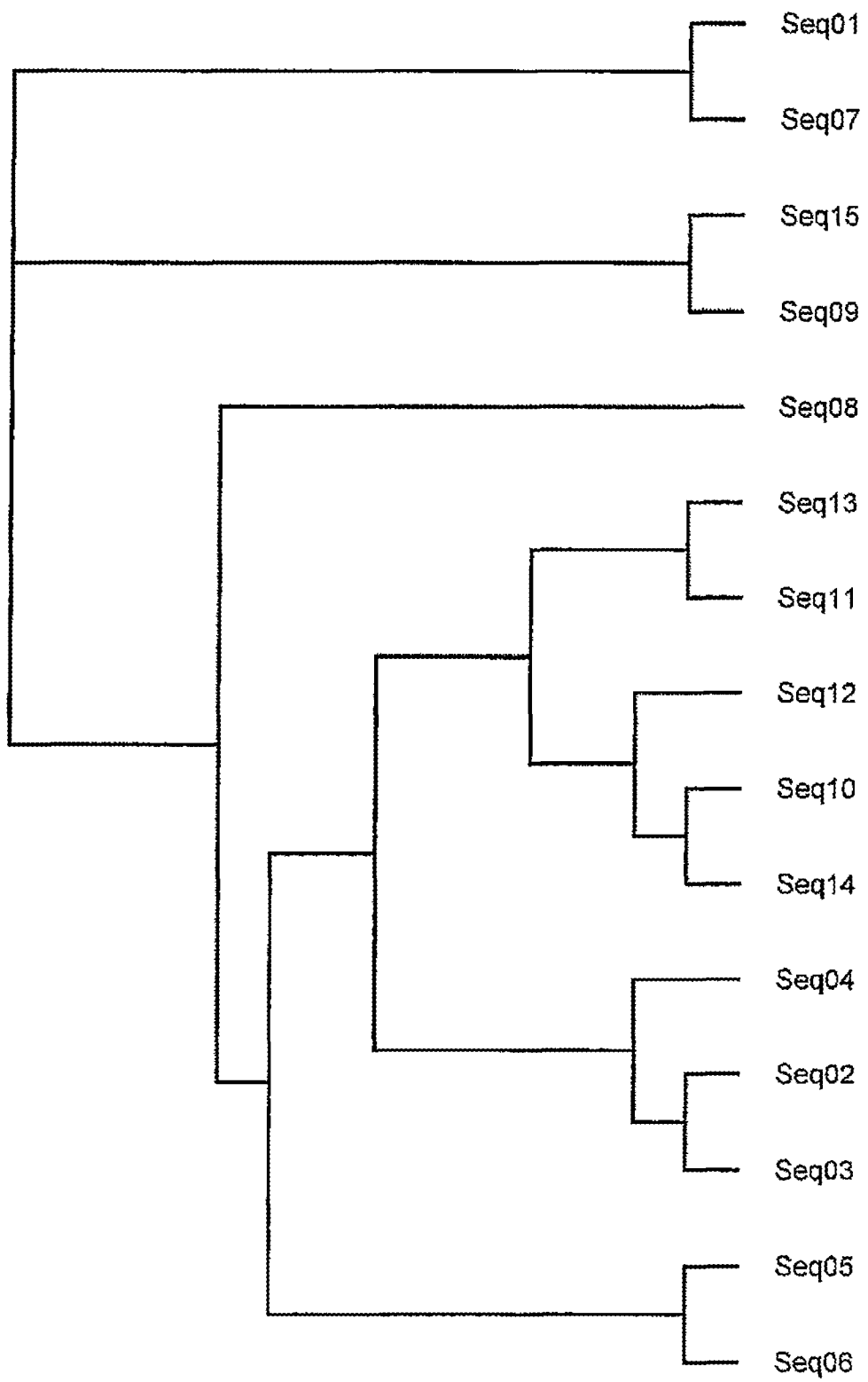
FIG. 5 is a figure of one of the four molecular phylogenetic trees created.
Figure 6:
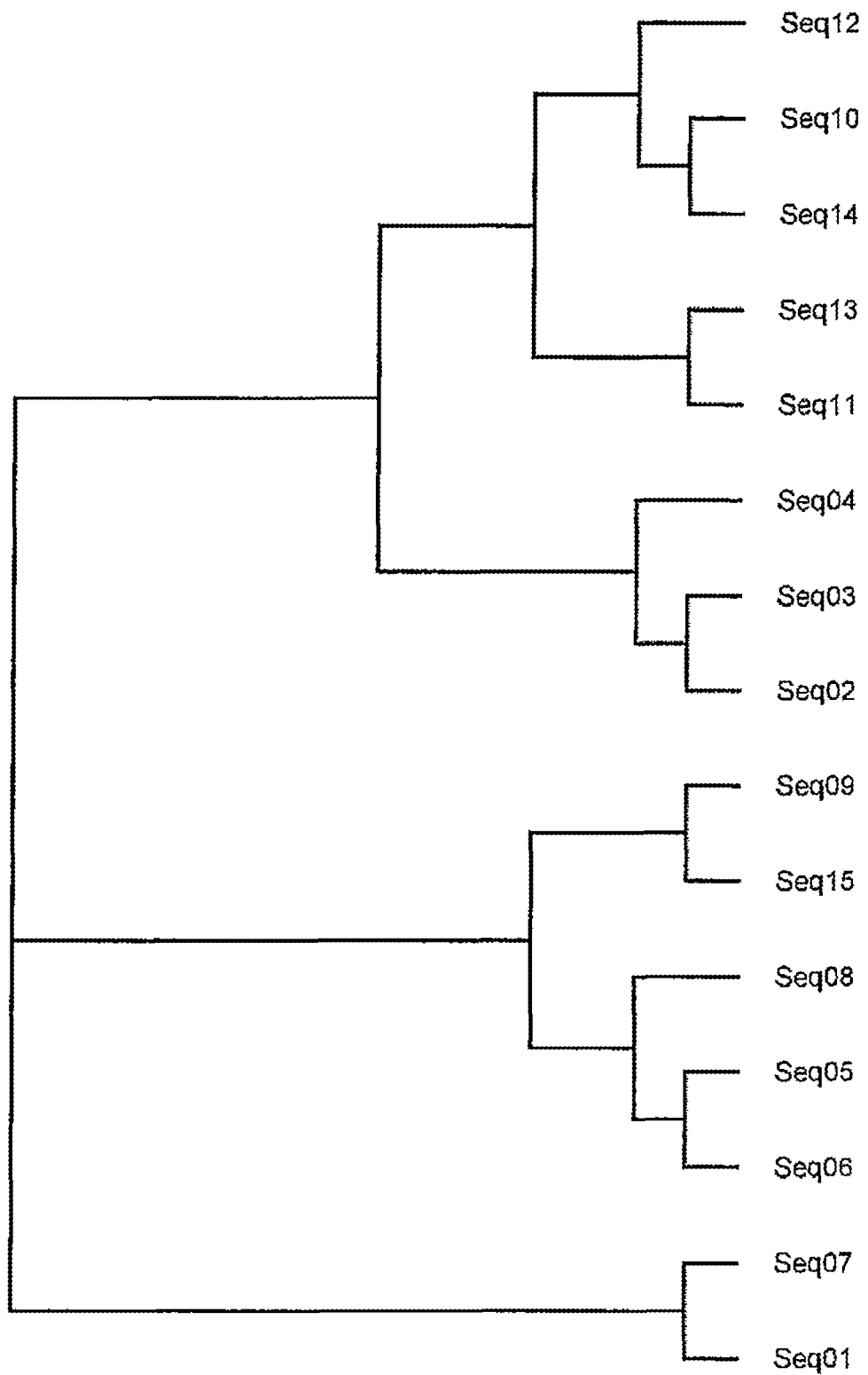
FIG. 6 is a figure of one of the four molecular phylogenetic trees created.

The amino acid sequence indicated with Tre3Anc is the estimated ancestor-type amino acid sequence at the root of the phylogenetic tree of FIG. 5. The amino acid sequence indicated with Tre4Anc is the estimated ancestor-type amino acid sequence at the root of the phylogenetic tree of FIG. 6.

When the multiple alignment figure including the estimated ancestor-type amino acid sequences and NAD(P)$^+$ GDH is observed, for example as shown in FIG. 9, the amino acid residue at position 217 of NAD(P)$^+$GDH derived from *Bacillus subtilis* (Seq 15) is tyrosine while all the ancestor-type amino acid residues aligned below are arginine. Accordingly, it was decided that arginine was introduced as a mutation. Similarly, other positions for introducing the estimated ancestor-type amino acids were decided, and it was decided to prepare and evaluate the mutant 1 to mutant 23 including the following amino acid replacements.

In this regard, as described in Patent Document 3, Non-Patent Document 6 and Non-Patent Document 7 of the prior art documents, the following replacements E170K and Q252L are known mutations, which were shown to improve the thermal stability of NAD(P)$^+$GDH derived from *Bacillus megaterium* and NAD(P)$^+$GDH derived from *Bacillus subtilis* in the presence and absence of sodium chloride. The replacements were used also in the present invention as well as the estimated ancestor-type amino acids.

The mutant 21 is a mutant in which the mutations described in Patent Document 1 and Patent Document 3 are combined, which was used as Comparative Example in Examples. The mutations of the mutant 22 are the mutations, which are described in Non-Patent Document 7 and were shown to have an effect on the thermal stability and the resistance to an organic solvent, and the mutant was used as Reference Example because the strain of genus *Bacillus* used was different.

The mutations of mutant 23 are the mutations, which are described in Non-Patent Document 7 and were shown to have an effect on the thermal stability and the resistance to an organic solvent, and the mutant was used as Example because the strain of genus *Bacillus* used was different.

Mutant 1: A159C+E170K+Q252L
Mutant 2: Q31G+A159C+E170K+Q252L
Mutant 3: G64A+A159C+E170K+Q252L
Mutant 4: K111R+A159C+E170K+Q252L
Mutant 5: A 159C+E170K+K179Y+Q252L
Mutant 6: A 159C+E170K+A246V+Q252L
Mutant 7: E170K+Y217R+I218L+Q252L
Mutant 8: Q31G+E170K+Y217R+I218L+Q252L
Mutant 9: G64A+E170K+Y217R+I218L+Q252L
Mutant 10: K111R+E170K+Y217R+I218L+Q252L
Mutant 11: E170K+K179Y+Y217R+I218L+Q252L
Mutant 12: E170K+Y217R+I218L+A246V+Q252L
Mutant 13: A159C+E170K+Y217R+I218L+Q252L
Mutant 14: Q31G+A159C+E170K+Y217R+I218L+Q252L
Mutant 15: G64A+A159C+E170K+Y217R+I218L+Q252L
Mutant 16: K111R+A159C+E170K+Y217R+I218L+Q252L
Mutant 17: A159C+E170K+K179Y+Y217R+I218L+Q252L
Mutant 18: A159C+E170K+Y217R+I218L+A246V+Q252L
Mutant 19: G64A+K111R+A159C+E170K+Y217R+I218L+Q252L
Mutant 20: Q31G+G64A+A159C+E170K+Y217R+I218L+Q252L
Mutant 21: E133K+E170K+Q252L
Mutant 22: E170K+Q252L
Mutant 23: P45A+N46E+F155Y+E170K+V227A+W230F+Q252L The expressions such as "A159C" in this specification relate to the notation of amino acid replacements. For example, "A159C" means that the amino acid A at position 159 from the N-terminal in a specific amino acid sequence is replaced with the amino acid C.

Further, the expressions such as "Y217R+I218L" in this specification mean that the amino acid replacements of Y217R and I218L are simultaneously introduced.

Example 2

Mutagenesis, Expression and Purification of NAD(P)$^+$GDH (2-1) Site-specific Mutagenesis of NAD(P)$^+$GDH Gene In order to synthesize each gene of the mutant 1 to mutant 23 described above, the site-specific mutagenesis by PGR was conducted regarding the DNA sequence of the wild-type NAD(P)$^+$GDH of the SEQ ID NO: 2. Before this, the oligonucleotides used for the site-specific mutagenesis by PGR were designed and synthesized as described below.

Regarding the mutation 1, the oligonucleotides having the nucleic acid sequences shown in the SEQ ID NO: 53 and the SEQ ID NO: 54, the SEQ ID NO: 55 and the SEQ ID NO: 56, and the SEQ ID NO: 57 and the SEQ ID NO: 58 of the sequence listing were used.

Regarding the mutation 2, the oligonucleotides having the nucleic acid sequences shown in the SEQ ID NO: 53 and the SEQ ID NO: 54, the SEQ ID NO: 55 and the SEQ ID NO: 56, the SEQ ID NO: 57 and the SEQ ID NO: 58. and the SEQ ID NO: 59 and the SEQ ID NO: 60 of the sequence listing were used.

Regarding the mutation 3, the oligonucleotides having the nucleic acid sequences shown in the SEQ ID NO: 53 and the SEQ ID NO: 54, the SEQ ID NO: 55 and the SEQ ID NO: 56, the SEQ ID NO: 57 and the SEQ ID NO: 58. and the SEQ ID NO: 61 and the SEQ ID NO: 62 of the sequence listing were used.

Regarding the mutation 4, the oligonucleotides having the nucleic acid sequences shown in the SEQ ID NO: 53 and the SEQ ID NO: 54, the SEQ ID NO: 55 and the SEQ ID NO: 56, the SEQ ID NO: 57 and the SEQ ID NO: 58, and the SEQ ID NO: 63 and the SEQ ID NO: 64 of the sequence listing were used.

Regarding the mutation 5, the oligonucleotides having the nucleic acid sequences shown in the SEQ ID NO: 53 and the SEQ ID NO: 54, the SEQ ID NO: 55 and the SEQ ID NO: 56, the SEQ ID NO: 57 and the SEQ ID NO: 58, and the SEQ ID NO: 65 and the SEQ ID NO: 66 of the sequence listing were used.

Regarding the mutation 6, the oligonucleotides having the nucleic acid sequences shown in the SEQ ID NO: 53 and the SEQ ID NO: 54, the SEQ ID NO: 55 and the SEQ ID NO: 56, the SEQ ID NO: 57 and the SEQ ID NO: 58, and the SEQ ID NO: 67 and the SEQ ID NO: 68 of the sequence listing were used.

Regarding the mutation 7, the oligonucleotides having the nucleic acid sequences shown in the SEQ ID NO: 55 and the SEQ ID NO: 56, the SEQ ID NO: 57 and the SEQ ID NO: 58, and the SEQ ID NO: 69 and the SEQ ID NO: 70 of the sequence listing were used.

Regarding the mutation 8, the oligonucleotides having the nucleic acid sequences shown in the SEQ ID NO: 55 and the SEQ ID NO: 56, the SEQ ID NO: 57 and the SEQ ID NO: 58, the SEQ ID NO: 59 and the SEQ ID NO: 60, and the SEQ ID NO: 69 and the SEQ ID NO; 70 of the sequence listing were used.

Regarding the mutation 9, the oligonucleotides having the nucleic acid sequences shown in the SEQ ID NO: 55 and the SEQ ID NO: 56, the SEQ ID NO: 57 and the SEQ ID NO: 58, the SEQ ID NO: 61, and the SEQ ID NO: 62, and the SEQ ID NO; 69 and the SEQ ID NO: 70 of the sequence listing were used.

Regarding the mutation 10, the oligonucleotides having the nucleic acid sequences shown in the SEQ ID NO: 55 and the SEQ ID NO: 56, the SEQ ID NO: 57 and the SEQ ID NO: 58, the SEQ ID NO: 63 and the SEQ ID NO: 64, and the SEQ ID NO: 69 and the SEQ ID NO: 70 of the sequence listing were used.

Regarding the mutation 11, the oligonucleotides having the nucleic acid sequences shown in the SEQ ID NO: 55 and the SEQ ID NO: 56, the SEQ ID NO: 57 and the SEQ ID NO: 58, the SEQ ID NO: 65 and the SEQ ID NO: 66, and the SEQ ID NO: 69 and the SEQ ID NO: 70 of the sequence listing were used.

Regarding the mutation 12, the oligonucleotides having the nucleic acid sequences shown in the SEQ ID NO: 55 and the SEQ ID NO: 56, the SEQ ID NO: 57 and the SEQ ID NO: 58, the SEQ ID NO: 67 and the SEQ ID NO: 68, and the SEQ ID NO: 69 and the SEQ ID NO: 70 of the sequence listing were used.

Regarding the mutation 13, the oligonucleotides having the nucleic acid sequences shown in the SEQ ID NO: 53 and the SEQ ID NO: 54, the SEQ ID NO: 55 and the SEQ ID NO: 56, the SEQ ID NO: 57 and the SEQ ID NO: 58, and the SEQ ID NO: 69 and the SEQ ID NO: 70 of the sequence listing were used.

Regarding the mutation 14, the oligonucleotides having the nucleic acid sequences shown in the SEQ ID NO: 53 and the SEQ ID NO: 54, the SEQ ID NO: 55 and the SEQ ID NO: 56, the SEQ ID NO: 57 and the SEQ ID NO: 58, the SEQ ID NO: 59 and the SEQ ID NO: 60, and the SEQ ID NO: 69 and the SEQ ID NO: 70 of the sequence listing were used.

Regarding the mutation 15, the oligonucleotides having the nucleic acid sequences shown in the SEQ ID NO: 53 and the SEQ ID NO: 54. the SEQ ID NO: 55 and the SEQ ID NO: 56, the SEQ ID NO: 57 and the SEQ ID NO: 58, the SEQ ID NO: 61 and the SEQ ID NO: 62, and the SEQ ID NO: 69 and the SEQ ID NO: 70 of the sequence listing were used.

Regarding the mutation 16, the oligonucleotides having the nucleic acid sequences shown in the SEQ ID NO: 53 and the SEQ ID NO: 54, the SEQ ID NO: 55 and the SEQ ID NO: 56, the SEQ ID NO: 57 and the SEQ ID NO: 58, the SEQ ID NO: 63 and the SEQ ID NO: 64, and the SEQ ID NO: 69 and the SEQ ID NO: 70 of the sequence listing were used.

Regarding the mutation 17, the oligonucleotides having the nucleic acid sequences shown in the SEQ ID NO: 53 and the SEQ ID NO: 54, the SEQ ID NO: 55 and the SEQ ID NO: 56, the SEQ ID NO: 57 and the SEQ ID NO: 58, the SEQ ID NO: 65 and the SEQ ID NO: 66, and the SEQ ID NO: 69 and the SEQ ID NO: 70 of the sequence listing were used.

Regarding the mutation 18, the oligonucleotides having the nucleic acid sequences shown in the SEQ ID NO: 53 and the SEQ ID NO: 54, the SEQ ID NO: 55 and the SEQ ID NO: 56, the SEQ ID NO: 57 and the SEQ ID NO: 58, the SEQ ID NO: 67 and the SEQ ID NO: 68, and the SEQ ID NO: 69 and the SEQ ID NO: 70 of the sequence listing were used.

Regarding the mutation 19, the oligonucleotides having the nucleic acid sequences shown in the SEQ ID NO: 53 and the SEQ ID NO: 54, the SEQ ID NO: 55 and the SEQ ID NO: 56, the SEQ ID NO: 57 and the SEQ ID NO: 58, the SEQ ID NO: 61 and the SEQ ID NO: 62, the SEQ ID NO: 63 and the SEQ ID NO: 64, and the SEQ ID NO: 69 and the SEQ ID NO: 70 of the sequence listing were used.

Regarding the mutation 20, the oligonucleotides having the nucleic acid sequences shown in the SEQ ID NO: 53 and the SEQ ID NO: 54, the SEQ ID NO: 55 and the SEQ ID NO: 56, the SEQ ID NO: 57 and the SEQ ID NO: 58, the SEQ ID NO: 59 and the SEQ ID NO: 60, the SEQ ID NO: 61 and the SEQ ID NO: 62, and the SEQ ID NO: 69 and the SEQ ID NO: 70 of the sequence listing were used.

Regarding the mutation 21, the oligonucleotides having the nucleic acid sequences shown in the SEQ ID NO: 55 and the SEQ ID NO: 56, the SEQ ID NO: 57 and the SEQ ID NO: 58, and the SEQ ID NO: 71and the SEQ ID NO: 72 of the sequence listing were used.

Regarding the mutation 22, the oligonucleotides having the nucleic acid sequences shown in the SEQ ID NO: 55 and the SEQ ID NO: 56, and the SEQ ID NO: 57 and the SEQ ID NO: 58 of the sequence listing were used.

Regarding the mutation 23, the oligonucleotides having the nucleic acid sequences shown in the SEQ ID NO: 55 and the SEQ ID NO: 56, the SEQ ID NO: 57 and the SEQ ID NO: 58, the SEQ ID NO: 73 and the SEQ ID NO: 74, the SEQ ID NO: 75 and the SEQ ID NO: 76, and the SEQ ID NO: 77 and the SEQ ID NO: 78 of the sequence listing were used.

As the template for the site-specific mutagenesis by PGR, the vector, in which the DNA of the wild-type NAD(P)$^+$GDH in the SEQ ID NO: 2 isolated by the usual method using PGR from *Bacillus subtilis* NBRC3134 strain was cloned to pET-21c, was used. This vector is also called pETGDH below.

Using the complementary oligonucleotides above and using QuickChange Lightning Site-Directed Mutagenesis kit (manufactured by Stratagene), the site-specific mutagenesis by PGR was conducted using pETGDH as a template. The method was in accordance with the protocol attached to the kit.

*Escherichia coli* DM5α was transfected with the vector after conducting the experiment of the site-specific mutagenesis and cloned, and it was confirmed by sequencing whether the desired mutations were inserted in the DNA of NAD(P)$^+$ GDH.

The obtained mutant vectors of the mutant 1 to mutant 23 were named pETGDH1, pETGDH2, pETGDH3, pETGDH4, pETGDH5, pETGDH6, pETGDH7, pETGDH8, pETGDH9, pETGDH10, pETGDH11, pETGDH12, pETGDH13, pETGDH14, pETGDH15, pETGDH16, pETGDH17, pETGDH18, pETGDH19, pETGDH20, pETGDH21, pETGDH22 and pETGDH23, respectively.

The DMA sequences of NAD(P)$^+$GDH that were cloned to pETGDH1 to pETGDH23 were as shown in the SEQ ID NO: 4, the SEQ ID NO: 6, the SEQ ID NO: 8, the SEQ ID NO: 10, the SEQ ID NO: 12, the SEQ ID NO: 14, the SEQ ID NO: 16, the SEQ ID NO: 18, the SEQ ID NO: 20, the SEQ ID NO: 22, the SEQ ID NO: 24, the SEQ ID NO: 26, the SEQ ID NO: 28, the SEQ ID NO: 30, the SEQ ID NO: 32, the SEQ ID NO: 34, the SEQ ID NO: 36, the SEQ ID NO: 38, the SEQ ID NO: 40, the SEQ ID NO: 42, the SEQ ID NO: 44, the SEQ ID NO: 46, and the SEQ ID NO: 48 of the sequence listing, respectively. The DNA sequence of wild-type NAD(P)$^+$GDH which was cloned to pETGDH was as shown by SEQ ID NO:2 of the sequence listing.

Thus, the amino acid sequences encoded by the DNA of NAD(P)$^+$GDH cloned to pETGDH1 to pETGDH23 were as shown in the SEQ ID NO: 3, the SEQ ID NO: 5, the SEQ ID NO: 7, the SEQ ID NO: 9, the SEQ ID NO: 11, the SEQ ID NO: 13, the SEQ ID NO: 15, the SEQ ID NO: 17, the SEQ ID NO: 19, the SEQ ID NO: 21, the SEQ ID NO: 23, the SEQ ID NO: 25, the SEQ ID NO: 27, the SEQ ID NO: 29, the SEQ ID NO: 31, the SEQ ID NO: 33, the SEQ ID NO: 35, the SEQ ID NO: 37, the SEQ ID NO: 39, the SEQ ID NO: 41, the SEQ ID NO: 43, the SEQ ID NO: 45 and the SEQ ID NO: 47 of the sequence listing, respectively. The amino acid sequence encoded by the DNA sequence of the wild-type NAD(P)+ GDH, which was cloned to pETGDH, was as shown in the SEQ ID NO: 1 of the sequence listing.

In this regard, the mutant, which includes the amino acid replacements of I165M+E170K+F194T+A197K+K204E+ K206R+E222D+S237C in the amino acid sequence shown in the SEQ ID NO: 79 of the sequence listing, [the mutant described in the SEQ ID NO: 164 of U.S. Pat. No. 7,816,111 specification (Patent Document 4)] was prepared as Comparative Example 1.

The homologies (%) of the nucleic acid sequences and amino acid sequences between the mutants 1 to 23 and Comparative Example 1, and the homologies (%) of the nucleic acid sequences between the mutants 1 to 23 and the wild-type are shown in Table 1.

expressed were collected. *Escherichia coli* collected were stored at −80° C. until they were used for the following purification step.

(2-3) Purification

*Escherichia coli* stored at −80° C. were each suspended in 20 mL of 20 mM phosphate buffer (pH 8) and grinded by ultrasonic wave. The grinded liquids were centrifuged (10000×g, 10 minutes) and the supernatants were collected. The supernatants collected were heat treated at 60° C. for 60 minutes and centrifuged (10000×g, 20 minutes), and the supernatants were collected.

Ammonium sulfate was added to the centrifugation supernatants obtained under ice-cooling to achieve 35% saturated ammonium sulfate, the ammonium sulfate precipitation was conducted, and the supernatants were collected by centrifu-

TABLE 1

| | | Sequence No. in sequence listing | | | Homology (%) | |
| --- | --- | --- | --- | --- | --- | --- |
| Mutant | Introduced Mutations | Amino acid sequence | Nucleic acid sequence | The SEQ ID NO:s of oligonucleotides necessary for gene synthesis | Comparative Example 1 Nucleic acid sequence | Wildtype Nucleic acid sequence |
| Mutant 1 | A159C + E170K + Q252L | 3 | 4 | 53 54 55 56 57 58 | 96.2 | 98.9 |
| Mutant 2 | Q31G + A159C + E170K + Q252L | 5 | 6 | 53 54 55 56 57 58 59 60 | 95.8 | 98.5 |
| Mutant 3 | G64A + A159C + E170K + Q252L | 7 | 8 | 53 54 55 56 57 58 61 62 | 95.8 | 98.5 |
| Mutant 4 | K111R + A159C + E170K + Q252L | 9 | 10 | 53 54 55 56 57 58 63 64 | 95.8 | 98.5 |
| Mutant 5 | A159C + E170K + K179Y + Q252L | 11 | 12 | 53 54 55 56 57 58 65 66 | 95.8 | 98.5 |
| Mutant 6 | A159C + E170K + A246V + Q252L | 13 | 14 | 53 54 55 56 57 58 67 68 | 95.8 | 98.5 |
| Mutant 7 | E170K + Y217R + I218L + Q252L | 15 | 16 | 55 56 57 58 69 70 | 95.8 | 98.5 |
| Mutant 8 | Q31G + E170K + Y217R + I218L + Q252L | 17 | 18 | 55 56 57 58 59 60 69 70 | 95.4 | 98.1 |
| Mutant 9 | G64A + E170K + Y217R + I218L + Q252L | 19 | 20 | 55 56 57 58 61 62 69 70 | 95.4 | 98.1 |
| Mutant 10 | K111R + E170K + Y217R + I218L + Q252L | 21 | 22 | 55 56 57 58 63 64 69 70 | 95.4 | 98.1 |
| Mutant 11 | E170K + K179Y + Y217R + I218L + Q252L | 23 | 24 | 55 56 57 58 65 66 69 70 | 95.4 | 98.1 |
| Mutant 12 | E170K + Y217R + I218L + A246V + Q252L | 25 | 26 | 55 56 57 58 67 68 69 70 | 95.4 | 98.1 |
| Mutant 13 | A159C + E170K + Y217R + I218L + Q252L | 27 | 28 | 53 54 55 56 57 58 69 70 | 95.4 | 98.1 |
| Mutant 14 | Q31G + A159C + E170K + Y217R + I218L + Q252L | 29 | 30 | 53 54 55 56 57 58 59 60 69 70 | 95.0 | 97.7 |
| Mutant 15 | G64A + A159C + E170K + Y217R + I218L + Q252L | 31 | 32 | 53 54 55 56 57 58 61 62 69 70 | 95.0 | 97.7 |
| Mutant 16 | K111R + A159C + E170K + Y217R + I218L + Q252L | 33 | 34 | 53 54 55 56 57 58 63 64 69 70 | 95.0 | 97.7 |
| Mutant 17 | A159C + E170K + K179Y + Y217R + I218L + Q252L | 35 | 36 | 53 54 55 56 57 58 65 66 69 70 | 95.0 | 97.7 |
| Mutant 18 | A159C + E170K + Y217R + I218L + A246V + Q252L | 37 | 38 | 53 54 55 56 57 58 67 68 69 70 | 95.0 | 97.7 |
| Mutant 19 | G64A + K111R + A159C + E170K + Y217R + I218L + Q252L | 39 | 40 | 53 54 55 56 57 58 61 62 63 64 69 70 | 94.6 | 97.3 |
| Mutant 20 | Q31G + G64A + A159C + E170K + Y217R + I218L + Q252L | 41 | 42 | 53 54 55 56 57 58 59 60 61 62 69 70 | 94.6 | 97.3 |
| Mutant 21 | E133K + E170K + Q252L | 43 | 44 | 55 56 57 58 71 72 | | |
| Mutant 22 | E170K + Q252L | 45 | 46 | 55 56 57 58 | | |
| Mutant 23 | P45A + N46E + F155Y + E170K + V227A + W230F + Q252L | 47 | 48 | 55 56 57 58 73 74 75 76 77 78 | | |

Using the transformants, which were prepared by transforming *Escherichia coli* DR5α with pETGDH1 to pETGDH23 and pETGDH, the following expression analysis experiment was conducted.

(2-2) Expression of NAD(P)+GDH Mutant Gene

The 25 kinds of transformants described above were cultured on LB agar plate medium including 100 μg/mL ampicillin and colonies were formed. A single colony was taken from each transformant, inoculated to 1 mL of LB medium including 100 μg/mL ampicillin and shake-cultured at 37° C.

1 mL of the precultured culture mediums were inoculated to Terrific culture mediums including 100 μg/mL ampicillin and 0.5 mM IPTG (isopropyl-β-thiogalactopyranoside) and shake-cultured at 30° C. After the completion of the culturing, the culture mediums were centrifuged (8000 rpm, 10 minutes) and *Escherichia coli* in which each mutant enzyme was gation (10000×g, 20 minutes). The centrifugation supernatants after the ammonium sulfate precipitation were adsorbed on 6 mL RESOURCE PHE columns (produced by GE Healthcare), which were equilibrated in advance with 20 mM phosphate buffer including 35% saturated ammonium sulfate, and eluted with the concentration gradient of 35% to 0% saturated ammonium sulfate.

The collected fractions having the NAD(P)+GDH activity were dialyzed with 20 mM phosphate buffer (pH 8.0), and concentrated on ultrafilter. It was confirmed with SDS-PAGE that the concentrated NAD(P)+GDH activity fractions were purified to single proteins. The NAD(P)+GDH mutant enzyme solutions, which were diaiyzed with 20 mM phosphate buffer (pH 8) and concentrated are also called the purified enzymes below.

Example 3

Evaluation of Properties of NAD(P)⁺GDH Mutant Enzyme

The evaluation of the properties of the mutant enzymes were conducted regarding the "specific activity", "thermal stability" and "acetone/heat-drying resistance" shown below. All items were conducted under the condition that the undiluted enzyme solution, enzyme dilution solution and solution for measuring the enzyme activity included no sodium chloride which has the effect to stabilize NAD(P)⁺GDH. The experimental results are shown in Table 2.

(3-1) Measurement of Specific Activity

The specific activities of the 25 kinds of NAD(P)⁺GDH mutant enzymes were calculated by the method above. The results are shown in Table 2.

(3-2) Measurement of Thermal Stability

The purified enzymes were diluted with the enzyme dilution solution: 20 mM phosphate buffer (pH 8), so that the protein concentrations became 30 μg/mL. 0.5 mL of the diluted enzyme solutions were dispensed to 1.5 mL plastic tubes. The plastic tubes were put into a water bath, in which the temperature was controlled to a predetermined temperature, and heat treated for 30 minutes. After the completion of the heat treatment, the plastic tubes were put into ice water for rapid cooling. The activities before and after the heat treatment were calculated from the method described above.

The remaining activity ratios (%) after the heat treatment were calculated with the activities before the heat treatment set as 100, and the ratios were used as the index for the thermal stability. The results are shown in Table 2.

(3-3) Measurement of Acetone/Heat-drying Resistance

The purified enzymes were diluted with the enzyme dilution solution: 20 mM phosphate buffer (pH 8), so that the protein concentrations became 500 μg/mL. 10 μL of the diluted enzyme solutions were each dispensed in 1.5 mL plastic tubes and 90 μL acetone was added thereto, and the tubes were stirred well at room temperature for 1 minute.

The above plastic tubes were set in centrifuge evaporator CVE-3100 (manufactured by EYELA), which was set at 50° C., and all the solvent was removed by heat-drying for 30 minutes. The enzyme powders after the completion of drying were each suspended in 20 mM phosphate buffer (pH 8) again, and the activities before and after the acetone/heat-drying treatment were calculated by the method described above.

The remaining activities (%) after the heat treatment were calculated with the activities before the heat treatment set as 100. The relative values were calculated with the remaining activity of the mutant 22 set as 1.0, and used as the index of the resistance to acetone. The results are shown in Table 2.

TABLE 2

| Mutant | Specific activity (U/mg) | Thermal stability test/remaining activity (%) | | | Acetone resistance test |
|---|---|---|---|---|---|
| | | 70° C. treatment | 80° C. treatment | 84° C. treatment | |
| Mutant 1 | 832 | 96 | 5 | 0 | 4.2 |
| Mutant 2 | 843 | 88 | 1 | 0 | 4.1 |
| Mutant 3 | 839 | 89 | 0 | 0 | 4.3 |
| Mutant 4 | 821 | 87 | 0 | 0 | 4.2 |
| Mutant 5 | 820 | 93 | 0 | 0 | 4.4 |
| Mutant 6 | 802 | 96 | 3 | 0 | 4.5 |
| Mutant 7 | 731 | 96 | 4 | 0 | 4.2 |
| Mutant 8 | 733 | 100 | 2 | 0 | 4.1 |
| Mutant 9 | 701 | 100 | 3 | 0 | 4.3 |
| Mutant 10 | 777 | 99 | 1 | 0 | 4.0 |
| Mutant 11 | 753 | 100 | 0 | 0 | 4.4 |
| Mutant 12 | 721 | 98 | 0 | 0 | 4.3 |
| Mutant 13 | 691 | 100 | 84 | 34 | 7.9 |
| Mutant 14 | 700 | 100 | 81 | 35 | 8.0 |
| Mutant 15 | 700 | 100 | 60 | 30 | 7.0 |
| Mutant 16 | 702 | 100 | 90 | 41 | 8.1 |
| Mutant 17 | 711 | 100 | 85 | 39 | 8.0 |
| Mutant 18 | 699 | 100 | 88 | 34 | 8.0 |
| Mutant 19 | 720 | 100 | 87 | 49 | 8.6 |
| Mutant 20 | 712 | 100 | 61 | 30 | 7.2 |
| Mutant 21 | 662 | 45 | 0 | 0 | 3.3 |
| Mutant 22 | 907 | 19 | 0 | 0 | 1.0 |
| Mutant 23 | 771 | 74 | 0 | 0 | 3.9 |
| Wild-type | 900 | 0 | 0 | 0 | 0.0 |
| Comparative Example 1 | 450 | 0 | 0 | 0 | 0.5 |

As shown in Table 2, regarding the specific activity, the specific activities of the mutants 1 to 21 and the mutant 23, in which the ancestor-type replacements were introduced, decreased slightly in comparison with the mutant 22 (E170K+Q252L), but the specific activities were not such values which cause a problem in practice.

Further, as shown in Table 2, regarding the thermal stability, it was shown that the mutant 1 (A159C+E170K+Q252L), the mutant 2 (Q31G+A159C+E170K+Q252L), the mutant 3 (G64A+A159C+E170K+Q252L), the mutant 4 (K111R+A159C+E170K+Q252L), the mutant 5 (A159C+E170K+K179Y+Q252L), the mutant 6 (A159C+E170K+A246V+Q252L), the mutant 7 (E170K+Y217R+I218L+Q252L), the mutant 8 (Q31G+E170K+Y217R+I218L+Q252L), the mutant 9 (G64+AE170K+Y217R+I218L+Q252L), the mutant 10 (K111R+E170K+Y217R+I218L+Q252L), the mutant 11 (E170K+K179Y+Y217R+I218L+Q252L), the mutant 12 (E170K+Y217R+I218L+A246V+Q252L), the mutant 13 (A159C+E170K+Y217R+I218L+Q252L), the mutant 14 (Q31G+A159C+E170K+Y217R+I218L+Q252L), the mutant 15 (G64A+A159C+E170K+Y217R+I218L+Q252L), the mutant 16 (K111R+A159C+E170K+Y217R+I218L+Q252L), the mutant 17 (A159C+E170K+K179Y+Y217R+I218L+Q252L), the mutant 18 (A159C+E170K+Y217R+I218L+A246V+Q252L), the mutant 19 (G64A+K111R+A159C+E170K+Y217R+I218L+Q252L), the mutant 20 (Q31G+G64A+A159C+E170K+Y217R+I218L+Q252L had extremely high thermal stability.

In addition, regarding the remaining activity after treating at 70° C. for 30 minutes, although the mutant 22 (E170K+Q252L) had the activity under 20%, the mutant 21 (E133K+E170K+Q252L) of Comparative Example had the activity of 45%, and the mutant 23 (P45A+N46E+F155Y+E170K+V227A+W230F+Q252L) had the activity of 74%. On the other hand, all the ancestor-type mutants of the mutant 1 to mutant 20 had the remaining activities of 80% or more, and the loss of the activity was not observed at all for most of them.

Similarly, regarding the remaining activity after treating at 80° C. for 30 minutes, the activities of the mutant 21, the mutant 22 and the mutant 23 of Comparative Examples were completely lost. On the other hand, the mutant 1, the mutant 2, the mutant 6, the mutant 7, the mutant 8, the mutant 9 and the mutant 10 showed the remaining activities of several %.

The mutant 13, the mutant 14, the mutant 15, the mutant 16, the mutant 17, the mutant 18, the mutant 19 and the mutant 20 showed the remaining activities of 60% or more.

Similarly, regarding the remaining activity after treating at 84° C. for 30 minutes, the activities of the mutant 21, the mutant 22 and the mutant 23 of Comparative Examples were completely lost. On the other hand, the mutant 13, the mutant 14, the mutant 15, the mutant 16, the mutant 17, the mutant 18, the mutant 19 and the mutant 20 showed the remaining activities of 30% or more.

As shown in Table 2, regarding the acetone resistance, it was shown that the resistance of the mutant 21 and the mutant 23 of Comparative Examples were less than four times higher in comparison, with the mutant 22, while the mutant 1 to mutant 20, in which the ancestor-type mutations were introduced, had the resistance at least four times higher. The mutant 13 to mutant 20 had the resistance at least seven times higher.

From these results, it was shown that, when only the amino acid replacements of E170K+Q252L were introduced, the mutant obtained has a very low remaining activity after the heat treatment at 70° C. or higher in the absence of an inorganic salt, and the activity is lost with the heat treatment at 80° C. or higher, and thus the mutant cannot function stably in a wide temperature range.

On the other hand, it was shown that, by including at least one amino acid replacement selected from the group consisting of Q31G, G64A, K111R, A159C, K179Y, Y217R, I218L and A246V in addition to the amino acid replacements of E170K+Q252L in the amino acid sequence shown in the SEQ ID NO: 1, the modified NAD(P)+GDH obtained functions stably after the heat treatment at 70° C. or higher and has the resistance to an organic solvent such as acetone, while it maintains a high specific activity of NAD(P)+GDR in the absence of an inorganic salt.

Furthermore, as shown in Table 2, in comparison with Comparative Example 1 (I165M+E170K+P194T+A197K+K204E+K206R+E222D+S237C), the mutants 1 to 20 had remarkably excellent thermal stability, resistance to acetone, and specific activity, and their resistance to acetone were also excellent. From these results, it was found that, although the homologies of the nucleic acid sequences of the mutants 1 to 20 of the present invention with Comparative Example 1 and the wild-type were as high as 95% or more as shown in Table 1, the heat resistant and the resistance to an organic solvent were remarkably superior.

Although the present invention was explained in detail and in reference to specific embodiments, it is obvious to one skilled in the art that various changes and modifications can be added without going beyond the spirit and the range of the present invention.

Although the present invention, was explained in detail using specific embodiments, it is obvious to one skilled in the art that various changes and modifications can be added without leaving the intention and the range of the present invention. In this regard, this application is based on the Japanese patent application applied on Mar. 30, 2011 (Japanese Patent Application No. 2011-75449) and the whole content thereof is incorporated by reference.

Industrial Applicability

By the present invention, it became possible to provide NAD(P)+GDH, which can be used stably in a wide temperature range, without being limited by the presence of an inorganic salt such as sodium chloride. More specifically, a mutant enzyme, which functions stably after the heat treatment at 70° C. or higher and has the resistance to an organic solvent such as acetone, while the high specific activity of NAD(P)+GDH derived from *Bacillus subtilis* is maintained in the absence of an inorganic salt, is provided by a genetic engineering method, so that it can be widely used in industrial applications; and a gene necessary for the mass production, a recombinant vector including the gene, a transformant obtained from the vector, and a method for producing the modified NAD(P)+GDH using the transformant are provided.

The invention claimed is:

1. A protein having a glucose dehydrogenase activity using nicotinamide adenine dinucleotide or nicotinamide adenine dinucleotide phosphate as a coenzyme, which comprises the following amino acid sequence of (a) or (b):

(a) an amino acid sequence, wherein glutamic acid at residue 170, alanine at residue 159 and glutamine at residue 252 of SEQ ID NO:1 are replaced with other amino acids, and at least one amino acid selected from the group consisting of glutamine at residue 31, glycine at residue 64, lysine at residue 111, lysine at residue 179, tyrosine at residue 217, isoleucine at 218 and alanine at residue 246 is replaced with another amino acid, or (b) an amino acid sequence, wherein one or several amino acids are deleted, replaced or added in the amino acid sequence of (a) at residue other than above residues 170, 252, 31, 64, 111, 159, 179, 217, 218 and 246 and has a sequence identity of 80% or higher to the amino acid sequence (a).

2. The protein of claim 1, wherein the amino acid sequence of (a) is an amino acid sequence in which the following amino acid replacements of (1) are made and at least one amino acid replacement selected from the group consisting of (2) to (8) is made in the amino acid sequence of SEQ ID NO: 1:
   (1) E170K+Q252L+A159C
   (2) Q31G
   (3) G64A
   (4) K111R
   (5) K179Y
   (6) Y217R
   (7) I218L
   (8) A246V.

3. The protein of claim 1, wherein the amino acid sequence of (a) is the amino acid of SEQ ID NOs: 5, 7, 9, 11, 13, 27, 29, 31, 33, 35, 37, 39, or 41.

4. The protein of claim 1, which further comprises a deletion, replacement, or addition at residues other than above residues 170, 252, 31, 64, 111, 159, 179, 217, 218 and 246, wherein the protein has a glucose dehydrogenase activity and has a sequence identity of 90% or higher to the amino acid sequence (a).

5. The protein of claim 1, wherein a remaining glucose dehydrogenase activity of the protein after a heat treatment at 70° C. for 30 minutes in the absence of an inorganic salt is higher than a remaining glucose dehydrogenase activity of the control protein of SEQ ID NO: 79.

6. The protein of claim 1, wherein a remaining glucose dehydrogenase activity of the protein after a heat treatment at 70° C. for 30 minutes in the absence of an inorganic salt is 20% or more of the glucose dehydrogenase activity of the protein before the heat treatment.

7. The protein of claim 1, wherein a remaining glucose dehydrogenase activity of the protein after a heat treatment at 80° C. for 30 minutes in the absence of an inorganic salt is 1% or more of the glucose dehydrogenase activity of the protein before the heat treatment.

8. The protein of claim 1, wherein a remaining glucose dehydrogenase activity of the protein after a heat treatment at 84° C. for 30 minutes in the absence of an inorganic salt is 1% or more of the glucose dehydrogenase activity of the protein before the heat treatment.

9. The protein according to claim 1, wherein a glucose dehydrogenase activity of the protein after treating the protein with acetone and removing the acetone in the absence of an inorganic salt is higher than a glucose dehydrogenase activity of the control protein of SEQ ID NO: 79.

10. The protein according to claim 1, wherein a glucose dehydrogenase activity of the protein after treating the protein with acetone and removing the acetone in the absence of an inorganic salt is higher than a glucose dehydrogenase activity of the control protein of SEQ ID NO: 1.

11. A DNA which encodes the protein of claim 1.

12. The DNA of claim 11, wherein the codon usage frequency of the nucleic acid sequence of the DNA is optimized to the codon usage frequency of *Escherichia coli*.

13. A recombinant vector which comprises the DNA of claim 11.

14. A transformant which comprises the recombinant vector of claim 13.

15. The transformant of according to claim 14, which is *Escherichia coil*.

16. A method for producing a modified glucose dehydrogenase which comprises producing glucose dehydrogenase by culturing the transformant of claim 14 and collecting the glucose dehydrogenase.

17. A test agent for glucose measurement which comprises the protein of claim 1.

18. A glucose sensor which comprises the protein of claim 1.

19. A method for measuring a glucose concentration, said method comprising:
   (a) providing a test sample;
   (b) contacting said test sample with the protein of claim 1 in the presence of the coenzyme; and
   (c) determine the glucose concentration in the test sample.

20. A protein comprising the amino acid sequence of SEQ ID NO: 3.

* * * * *

SEQUENCE LISTING

```
<160> NUMBER OF SEQ ID NOS: 79

<210> SEQ ID NO 1
<211> LENGTH: 261
<212> TYPE: PRT
<213> ORGANISM: Bacillus subtilis

<400> SEQUENCE: 1

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Asn Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Ser Thr Asn Leu Thr Gly Ala Phe Leu Gly Ser Arg Glu Ala Ile
        115                 120                 125
```

```
Lys Tyr Phe Val Glu Asn Asp Ile Lys Gly Asn Val Ile Asn Met Ser
        130                 135                 140

Ser Val His Glu Val Ile Pro Trp Pro Leu Phe Val His Tyr Ala Ala
145                 150                 155                 160

Ser Lys Gly Gly Ile Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Arg Ala Asp
        195                 200                 205

Val Glu Ser Met Ile Pro Met Gly Tyr Ile Gly Glu Pro Glu Glu Ile
210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 2
<211> LENGTH: 786
<212> TYPE: DNA
<213> ORGANISM: Bacillus subtilis

<400> SEQUENCE: 2
atgtatccgg atttaaaagg aaaagtcgtc gctattacag agctgcttc aggattaggg      60 aaggcaatgg ccattcgctt cggcaaggag caggcaaaag tggttatcaa ctactacagc     120
aataagcagg atccgaacga ggtaaaggaa gaggtcatca aggcgggcgg tgaagctgtt     180
gtcgtccaag gagacgtaac aaaagaggaa gatgtaaaaa catcgtcca aacagcgatt     240 aacgagttcg gtacactcga tattatgatt aataatgccg gtcttgaaaa tcccgttcct     300
tctcatgaaa tgccgctgaa ggattgggat aaagtaatca gcacgaactt aacgggcgcc     360 ttttaggaa gccgtgaagc gattaaatat tttgttgaaa acgatataaa aggaaatgtc     420
attaatatgt cgagcgtaca tgaagtgatt ccgtggccat atttgttca ctatgcggca     480 agtaaaggcg gaatcaagct gatgacggaa acattggcgc tggaatatgc gccgaaaggc     540
attcgtgtca acaatatcgg gccaggcgcg atcaacacgc caatcaatgc tgaaaaattt     600
gctgatccta agcagagagc agatgtagaa agcatgattc cgatgggata tatcggtgaa     660
ccggaggaaa ttgcggcagt agcagcctgg cttgcttcga aggaagccag ctacgtcaca     720
ggcatcacgt tattcgcgga cggcggtatg acccaatatc cttcattcca ggcaggccgc     780
ggttaa                                                                 786

<210> SEQ ID NO 3
<211> LENGTH: 261
<212> TYPE: PRT
<213> ORGANISM: Bacillus subtilis

<400> SEQUENCE: 3

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45
```

```
Lys Glu Glu Val Ile Lys Ala Gly Gly Glu Ala Val Val Gln Gly
         50                  55                  60
Asp Val Thr Lys Glu Glu Asp Val Lys Asn Ile Val Gln Thr Ala Ile
 65                  70                  75                  80
Asn Glu Phe Gly Thr Leu Asp Ile Met Ile Asn Asn Ala Gly Leu Glu
                 85                  90                  95
Asn Pro Val Pro Ser His Glu Met Pro Leu Lys Asp Trp Asp Lys Val
                100                 105                 110
Ile Ser Thr Asn Leu Thr Gly Ala Phe Leu Gly Ser Arg Glu Ala Ile
                115                 120                 125
Lys Tyr Phe Val Glu Asn Asp Ile Lys Gly Asn Val Ile Asn Met Ser
        130                 135                 140
Ser Val His Glu Val Ile Pro Trp Pro Leu Phe Val His Tyr Cys Ala
145                 150                 155                 160
Ser Lys Gly Gly Ile Lys Leu Met Thr Lys Thr Leu Ala Leu Glu Tyr
                165                 170                 175
Ala Pro Lys Gly Ile Arg Val Asn Asn Ile Gly Pro Gly Ala Ile Asn
        180                 185                 190
Thr Pro Ile Asn Ala Glu Lys Phe Ala Asp Pro Lys Gln Arg Ala Asp
        195                 200                 205
Val Glu Ser Met Ile Pro Met Gly Tyr Ile Gly Glu Pro Glu Glu Ile
210                 215                 220
Ala Ala Val Ala Ala Trp Leu Ala Ser Lys Glu Ala Ser Tyr Val Thr
225                 230                 235                 240
Gly Ile Thr Leu Phe Ala Asp Gly Gly Met Thr Leu Tyr Pro Ser Phe
                245                 250                 255
Gln Ala Gly Arg Gly
        260

<210> SEQ ID NO 4
<211> LENGTH: 786
<212> TYPE: DNA
<213> ORGANISM: Bacillus subtilis

<400> SEQUENCE: 4
atgtatccgg atttaaaagg aaaagtcgtc gctattacag gagctgcttc aggattaggg      60
aaggcaatgg ccattcgctt cggcaaggag caggcaaaag tggttatcaa ctactacagc     120
aataagcagg atccgaacga ggtaaaggaa gaggtcatca aggcgggcgg tgaagctgtt     180
gtcgtccaag gagacgtaac aaaagaggaa gatgtaaaaa acatcgtcca acagcgatt      240
aacgagttcg gtacactcga tattatgatt aataatgccg gtcttgaaaa tcccgttcct     300
tctcatgaaa tgccgctgaa ggattgggat aaagtaatca gcacgaactt aacgggcgcc     360
ttttaggaa gccgtgaagc gattaaatat tttgttgaaa acgatataaa ggaaatgtc       420
attaatatgt cgagcgtaca tgaagtgatt ccgtggccat atttgttca ctattgcgca      480
agtaaaggcg gaatcaagct gatgacgaaa acattggcgc tggaatatgc gccgaaaggc    540
attcgtgtca acaatatcgg gccaggcgcg atcaacacgc caatcaatgc tgaaaaattt    600
gctgatccta agcagagagc agatgtagaa agcatgattc cgatgggata tatcggtgaa    660
ccggaggaaa ttgcggcagt agcagcctgg cttgcttcga aggaagccag ctacgtcaca    720
ggcatcacgt tattcgcgga cggcggtatg accctgtatc cttcattcca ggcaggccgc    780
ggttaa                                                               786
```

```
<210> SEQ ID NO 5
<211> LENGTH: 261
<212> TYPE: PRT
<213> ORGANISM: Bacillus subtilis

<400> SEQUENCE: 5

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gly Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Asn Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Ser Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Cys Ala
145                 150                 155                 160

Ser Lys Gly Gly Ile Lys Leu Met Thr Lys Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Arg Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Leu Tyr Pro Ser Phe
                245                 250                 255

Gln Ala Gly Arg Gly
            260

<210> SEQ ID NO 6
<211> LENGTH: 786
<212> TYPE: DNA
<213> ORGANISM: Bacillus subtilis

<400> SEQUENCE: 6
atgtatccgg atttaaaagg aaaagtcgtc gctattacag agctgcttc aggattaggg      60 aaggcaatgg ccattcgctt cggcaaggag ggtgcaaaag tggttatcaa ctactacagc    120
aataagcagg atccgaacga ggtaaaggaa gaggtcatca aggcgggcgg tgaagctgtt    180
gtcgtccaag agacgtaac aaaagaggaa gatgtaaaaa acatcgtcca acagcgatt     240 aacgagttcg gtacactcga tattatgatt aataatgccg gtcttgaaaa tcccgttcct    300
tctcatgaaa tgccgctgaa ggattgggat aaagtaatca gcacgaactt aacgggcgcc    360 ttttaggaa gccgtgaagc gattaaatat tttgttgaaa acgatataaa aggaaatgtc    420
```

```
attaatatgt cgagcgtaca tgaagtgatt ccgtggccat tatttgttca ctattgcgca    480
agtaaaggcg gaatcaagct gatgacgaaa acattggcgc tggaatatgc gccgaaaggc    540
attcgtgtca acaatatcgg gccaggcgcg atcaacacgc caatcaatgc tgaaaaattt    600
gctgatccta agcagagagc agatgtagaa agcatgattc cgatgggata tatcggtgaa    660
ccggaggaaa ttgcggcagt agcagcctgg cttgcttcga aggaagccag ctacgtcaca    720
ggcatcacgt tattcgcgga cggcggtatg accctgtatc cttcattcca ggcaggccgc    780
ggttaa    786
```

<210> SEQ ID NO 7
<211> LENGTH: 261
<212> TYPE: PRT
<213> ORGANISM: Bacillus subtilis

<400> SEQUENCE: 7

```
Met Tyr Pro Asp Leu Lys Gly Lys Val Ala Ile Thr Gly Ala Ala
1               5                   10                  15

Ser Gly Leu Gly Lys Ala Met Ala Ile Arg Phe Gly Lys Glu Gln Ala
                20                  25                  30

Lys Val Val Ile Asn Tyr Tyr Ser Asn Lys Gln Asp Pro Asn Glu Val
                35                  40                  45

Lys Glu Glu Val Ile Lys Ala Gly Gly Glu Ala Val Val Val Gln Ala
            50                  55                  60

Asp Val Thr Lys Glu Glu Asp Val Lys Asn Ile Val Gln Thr Ala Ile
65                  70                  75                  80

Asn Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
                100                 105                 110

Ile Ser Thr Asn Leu Thr Gly Ala Phe Leu Gly Ser Arg Glu Ala Ile
            115                 120                 125

Lys Tyr Phe Val Glu Asn Asp Ile Lys Gly Asn Val Ile Asn Met Ser
130                 135                 140

Ser Val His Glu Val Ile Pro Trp Pro Leu Phe Val His Tyr Cys Ala
145                 150                 155                 160

Ser Lys Gly Gly Ile Lys Leu Met Thr Lys Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Arg Ala Asp
            195                 200                 205

Val Glu Ser Met Ile Pro Met Gly Tyr Ile Gly Glu Pro Glu Glu Ile
        210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Leu Tyr Pro Ser Phe
                245                 250                 255

Gln Ala Gly Arg Gly
            260
```

<210> SEQ ID NO 8
<211> LENGTH: 786
<212> TYPE: DNA
<213> ORGANISM: Bacillus subtilis

<400> SEQUENCE: 8

```
atgtatccgg atttaaaagg aaaagtcgtc gctattacag gagctgcttc aggattaggg      60
aaggcaatgg ccattcgctt cggcaaggag caggcaaaag tggttatcaa ctactacagc     120
aataagcagg atccgaacga ggtaaaggaa gaggtcatca aggcgggcgg tgaagctgtt     180
gtcgtccaag cggacgtaac aaaagaggaa gatgtaaaaa acatcgtcca acagcgatt     240
aacgagttcg gtacactcga tattatgatt aataatgccg gtcttgaaaa tcccgttcct     300
tctcatgaaa tgccgctgaa ggattgggat aaagtaatca gcacgaactt aacgggcgcc     360
ttttaggaa gccgtgaagc gattaaatat tttgttgaaa acgatataaa aggaaatgtc      420
attaatatgt cgagcgtaca tgaagtgatt ccgtggccat atttgttca ctattgcgca     480
agtaaaggcg gaatcaagct gatgacgaaa acattggcgc tggaatatgc gccgaaaggc     540
attcgtgtca acaatatcgg gccaggcgcg atcaacacgc caatcaatgc tgaaaaattt     600
gctgatccta agcagagagc agatgtgaaa agcatgattc cgatgggata tatcggtgaa     660
ccggaggaaa ttgcggcagt agcagcctgg cttgcttcga aggaagccag ctacgtcaca     720
ggcatcacgt tattcgcgga cggcggtatg accctgtatc cttcattcca ggcaggccgc     780
ggttaa                                                                 786
```

<210> SEQ ID NO 9
<211> LENGTH: 261
<212> TYPE: PRT
<213> ORGANISM: Bacillus subtilis

<400> SEQUENCE: 9

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
                20                  25                  30

Lys Val Val Ile Asn Tyr Tyr Ser Asn Lys Gln Asp Pro Asn Glu Val
            35                  40                  45

Lys Glu Glu Val Ile Lys Ala Gly Gly Glu Ala Val Val Val Gln Gly
        50                  55                  60

Asp Val Thr Lys Glu Glu Asp Val Lys Asn Ile Val Gln Thr Ala Ile
65                  70                  75                  80

Asn Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Arg Val
            100                 105                 110

Ile Ser Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Cys Ala
145                 150                 155                 160

Ser Lys Gly Gly Ile Lys Leu Met Thr Lys Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Arg Ala Asp
        195                 200                 205

Val Glu Ser Met Ile Pro Met Gly Tyr Ile Gly Glu Pro Glu Glu Ile
```

```
        210                 215                 220
Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Leu Tyr Pro Ser Phe
                245                 250                 255

Gln Ala Gly Arg Gly
            260
```

<210> SEQ ID NO 10
<211> LENGTH: 786
<212> TYPE: DNA
<213> ORGANISM: Bacillus subtilis

<400> SEQUENCE: 10

```
atgtatccgg atttaaaagg aaaagtcgtc gctattacag agctgcttc aggattaggg      60
aaggcaatgg ccattcgctt cggcaaggag caggcaaaag tggttatcaa ctactacagc    120
aataagcagg atccgaacga ggtaaaggaa gaggtcatca aggcgggcgg tgaagctgtt    180
gtcgtccaag agacgtaac aaaagaggaa gatgtaaaaa acatcgtcca acagcgatt     240
aacgagttcg gtacactcga tattatgatt aataatgccg gtcttgaaaa tcccgttcct    300
tctcatgaaa tgccgctgaa ggattgggat cgcgtaatca gcacgaactt aacgggcgcc    360
tttttaggaa gccgtgaagc gattaaatat tttgttgaaa acgatataaa aggaaatgtc    420
attaatatgt cgagcgtaca tgaagtgatt ccgtggccat atttgttca ctattgcgca    480
agtaaaggcg gaatcaagct gatgacgaaa acattggcgc tggaatatgc gccgaaaggc    540
attcgtgtca caatatcgg gccaggcgcg atcaacacgc aatcaatgc tgaaaaattt     600
gctgatccta gcagagagc agatgtgaaa agcatgattc cgatgggata tatcggtgaa    660
ccggaggaaa ttgcggcagt agcagcctgg cttgcttcga aggaagccag ctacgtcaca    720
ggcatcacgt tattcgcgga cggcggtatg accctgtatc cttcattcca ggcaggccgc    780
ggttaa                                                                786
```

<210> SEQ ID NO 11
<211> LENGTH: 261
<212> TYPE: PRT
<213> ORGANISM: Bacillus subtilis

<400> SEQUENCE: 11

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Gln Gly
    50                  55                  60

Asp Val Thr Lys Glu Glu Asp Val Lys Asn Ile Val Gln Thr Ala Ile
65                  70                  75                  80

Asn Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Ser Thr Asn Leu Thr Gly Ala Phe Leu Gly Ser Arg Glu Ala Ile
        115                 120                 125
```

```
Lys Tyr Phe Val Glu Asn Asp Ile Lys Gly Asn Val Ile Asn Met Ser
            130                 135                 140
Ser Val His Glu Val Ile Pro Trp Pro Leu Phe Val His Tyr Cys Ala
145                 150                 155                 160
Ser Lys Gly Gly Ile Lys Leu Met Thr Lys Thr Leu Ala Leu Glu Tyr
                165                 170                 175
Ala Pro Tyr Gly Ile Arg Val Asn Asn Ile Gly Pro Gly Ala Ile Asn
            180                 185                 190
Thr Pro Ile Asn Ala Glu Lys Phe Ala Asp Pro Lys Gln Arg Ala Asp
        195                 200                 205
Val Glu Ser Met Ile Pro Met Gly Tyr Ile Glu Pro Glu Glu Ile
210                 215                 220
Ala Ala Val Ala Ala Trp Leu Ala Ser Lys Glu Ala Ser Tyr Val Thr
225                 230                 235                 240
Gly Ile Thr Leu Phe Ala Asp Gly Gly Met Thr Leu Tyr Pro Ser Phe
                245                 250                 255
Gln Ala Gly Arg Gly
            260

<210> SEQ ID NO 12
<211> LENGTH: 786
<212> TYPE: DNA
<213> ORGANISM: Bacillus subtilis

<400> SEQUENCE: 12
atgtatccgg atttaaaagg aaaagtcgtc gctattacag gagctgcttc aggattaggg      60
aaggcaatgg ccattcgctt cggcaaggag caggcaaaag tggttatcaa ctactacagc     120
aataagcagg atccgaacga ggtaaaggaa gaggtcatca aggcgggcgg tgaagctgtt     180
gtcgtccaag gagacgtaac aaaagaggaa gatgtaaaaa acatcgtcca aacagcgatt     240
aacgagttcg gtacactcga tattatgatt aataatgccg gtcttgaaaa tcccgttcct     300
tctcatgaaa tgccgctgaa ggattgggat aaagtaatca gcacgaactt aacgggcgcc     360 ttttaggaa gccgtgaagc gattaaatat tttgttgaaa acgatataaa aggaaatgtc      420
attaatatgt cgagcgtaca tgaagtgatt ccgtggccat atttgttca ctattgcgca     480 agtaaaggcg gaatcaagct gatgacgaaa acattggcgc tggaatatgc gccgtatggc     540
attcgtgtca acaatatcgg gccaggcgcg atcaacacgc caatcaatgc tgaaaaattt     600
gctgatccta gcagagagc agatgtagaa agcatgattc cgatgggata tatcggtgaa      660
ccggaggaaa ttgcggcagt agcagcctgg cttgcttcga aggaagccag ctacgtcaca     720
ggcatcacgt tattcgcgga cggcggtatg accctgtatc cttcattcca ggcaggccgc     780
ggttaa                                                                786

<210> SEQ ID NO 13
<211> LENGTH: 261
<212> TYPE: PRT
<213> ORGANISM: Bacillus subtilis

<400> SEQUENCE: 13

Met Tyr Pro Asp Leu Lys Gly Lys Val Val Ala Ile Thr Gly Ala Ala
1               5                   10                  15
Ser Gly Leu Gly Lys Ala Met Ala Ile Arg Phe Gly Lys Glu Gln Ala
            20                  25                  30
Lys Val Val Ile Asn Tyr Tyr Ser Asn Lys Gln Asp Pro Asn Glu Val
        35                  40                  45
```

```
Lys Glu Glu Val Ile Lys Ala Gly Gly Glu Ala Val Val Gln Gly
         50                  55                  60
Asp Val Thr Lys Glu Glu Asp Val Lys Asn Ile Val Gln Thr Ala Ile
 65                  70                  75                  80
Asn Glu Phe Gly Thr Leu Asp Ile Met Ile Asn Asn Ala Gly Leu Glu
                 85                  90                  95
Asn Pro Val Pro Ser His Glu Met Pro Leu Lys Asp Trp Asp Lys Val
            100                 105                 110
Ile Ser Thr Asn Leu Thr Gly Ala Phe Leu Gly Ser Arg Glu Ala Ile
            115                 120                 125
Lys Tyr Phe Val Glu Asn Asp Ile Lys Gly Asn Val Ile Asn Met Ser
        130                 135                 140
Ser Val His Glu Val Ile Pro Trp Pro Leu Phe Val His Tyr Cys Ala
145                 150                 155                 160
Ser Lys Gly Gly Ile Lys Leu Met Thr Lys Thr Leu Ala Leu Glu Tyr
                165                 170                 175
Ala Pro Lys Gly Ile Arg Val Asn Asn Ile Gly Pro Gly Ala Ile Asn
            180                 185                 190
Thr Pro Ile Asn Ala Glu Lys Phe Ala Asp Pro Lys Gln Arg Ala Asp
            195                 200                 205
Val Glu Ser Met Ile Pro Met Gly Tyr Ile Gly Glu Pro Glu Glu Ile
        210                 215                 220
Ala Ala Val Ala Ala Trp Leu Ala Ser Lys Glu Ala Ser Tyr Val Thr
225                 230                 235                 240
Gly Ile Thr Leu Phe Val Asp Gly Gly Met Thr Leu Tyr Pro Ser Phe
                245                 250                 255
Gln Ala Gly Arg Gly
            260

<210> SEQ ID NO 14
<211> LENGTH: 786
<212> TYPE: DNA
<213> ORGANISM: Bacillus subtilis

<400> SEQUENCE: 14
atgtatccgg atttaaaagg aaaagtcgtc gctattacag gagctgcttc aggattaggg      60
aaggcaatgg ccattcgctt cggcaaggag caggcaaaag tggttatcaa ctactacagc     120
aataagcagg atccgaacga ggtaaaggaa gaggtcatca aggcgggcgg tgaagctgtt     180
gtcgtccaag gagacgtaac aaaagaggaa gatgtaaaaa acatcgtcca acagcgatt      240 aacgagttcg gtacactcga tattatgatt aataatgccg gtcttgaaaa tcccgttcct     300
tctcatgaaa tgccgctgaa ggattgggat aaagtaatca gcacgaactt aacgggcgcc     360 ttttagga gccgtgaagc gattaaatat tttgttgaaa acgatataaa aggaaatgtc      420
attaatatgt cgagcgtaca tgaagtgatt ccgtggccat tatttgttca ctattgcgca     480
agtaaaggcg gaatcaagct gatgacgaaa acattggcgc tggaatatgc gccgaaaggc     540
attcgtgtca acaatatcgg gccaggcgcg atcaacacgc caatcaatgc tgaaaaattt     600
gctgatccta agcagagagc agatgtagaa agcatgattc cgatgggata tatcggtgaa     660
ccggaggaaa ttgcggcagt agcagcctgg cttgcttcga aggaagccag ctacgtcaca     720
ggcatcacgt tattcgtgga cggcggtatg accctgtatc cttcattcca ggcaggccgc     780
ggttaa                                                                786
```

<210> SEQ ID NO 15
<211> LENGTH: 261
<212> TYPE: PRT
<213> ORGANISM: Bacillus subtilis

<400> SEQUENCE: 15

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Gln Gly
    50                  55                  60

Asp Val Thr Lys Glu Glu Asp Val Lys Asn Ile Val Gln Thr Ala Ile
65                  70                  75                  80

Asn Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Ser Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Ile Lys Leu Met Thr Lys Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Arg Ala Asp
        195                 200                 205

Val Glu Ser Met Ile Pro Met Gly Arg Leu Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Leu Tyr Pro Ser Phe
                245                 250                 255

Gln Ala Gly Arg Gly
            260

<210> SEQ ID NO 16
<211> LENGTH: 786
<212> TYPE: DNA
<213> ORGANISM: Bacillus subtilis

<400> SEQUENCE: 16
atgtatccgg atttaaaagg aaaagtcgtc gctattacag gagctgcttc aggattaggg      60
aaggcaatgg ccattcgctt cggcaaggag caggcaaaag tggttatcaa ctactacagc     120
aataagcagg atccgaacga ggtaaaggaa gaggtcatca aggcgggcgg tgaagctgtt     180
gtcgtccaag gagacgtaac aaaagaggaa gatgtaaaaa acatcgtcca acagcgatt     240 aacgagttcg gtacactcga tattatgatt aataatgccg gtcttgaaaa tcccgttcct     300
tctcatgaaa tgccgctgaa ggattgggat aaagtaatca gcacgaactt aacgggcgcc     360

```
ttttaggaa gccgtgaagc gattaaatat tttgttgaaa acgatataaa aggaaatgtc    420
attaatatgt cgagcgtaca tgaagtgatt ccgtggccat tatttgttca ctatgcggca    480
agtaaaggcg gaatcaagct gatgacgaaa acattggcgc tggaatatgc gccgaaaggc    540
attcgtgtca acaatatcgg gccaggcgcg atcaacacgc caatcaatgc tgaaaaattt    600
gctgatccta agcagagagc agatgtagaa agcatgattc cgatgggacg cctgggtgaa    660
ccggaggaaa ttgcggcagt agcagcctgg cttgcttcga aggaagccag ctacgtcaca    720
ggcatcacgt tattcgcgga cggcggtatg accctgtatc cttcattcca ggcaggccgc    780
ggttaa                                                              786
```

<210> SEQ ID NO 17
<211> LENGTH: 261
<212> TYPE: PRT
<213> ORGANISM: Bacillus subtilis

<400> SEQUENCE: 17

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gly Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Gln Gly
    50                  55                  60

Asp Val Thr Lys Glu Glu Asp Val Lys Asn Ile Val Gln Thr Ala Ile
65                  70                  75                  80

Asn Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Ser Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Ile Lys Leu Met Thr Lys Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Arg Ala Asp
        195                 200                 205

Val Glu Ser Met Ile Pro Met Gly Arg Leu Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Leu Tyr Pro Ser Phe
                245                 250                 255

Gln Ala Gly Arg Gly
            260
```

<210> SEQ ID NO 18
<211> LENGTH: 786
<212> TYPE: DNA

<213> ORGANISM: Bacillus subtilis

<400> SEQUENCE: 18

```
atgtatccgg atttaaaagg aaaagtcgtc gctattacag gagctgcttc aggattaggg      60
aaggcaatgg ccattcgctt cggcaaggag ggtgcaaaag tggttatcaa ctactacagc     120
aataagcagg atccgaacga ggtaaaggaa gaggtcatca aggcgggcgg tgaagctgtt     180
gtcgtccaag gagacgtaac aaaagaggaa gatgtaaaaa acatcgtcca aacagcgatt     240
aacgagttcg gtacactcga tattatgatt aataatgccg gtcttgaaaa tcccgttcct     300
tctcatgaaa tgccgctgaa ggattgggat aaagtaatca gcacgaactt aacgggcgcc     360
tttttaggaa gccgtgaagc gattaaatat tttgttgaaa acgatataaa aggaaatgtc     420
attaatatgt cgagcgtaca tgaagtgatt ccgtggccat tatttgttca ctatgcggca     480
agtaaaggcg gaatcaagct gatgacgaaa acattggcgc tggaatatgc gccgaaaggc     540
attcgtgtca acaatatcgg gccaggcgcg atcaacacgc caatcaatgc tgaaaaattt     600
gctgatccta gcagagagc agatgtagaa agcatgattc cgatgggacg cctgggtgaa     660
ccggaggaaa ttgcggcagt agcagcctgg cttgcttcga aggaagccag ctacgtcaca     720
ggcatcacgt tattcgcgga cggcggtatg accctgtatc cttcattcca ggcaggccgc     780
ggttaa                                                                 786
```

<210> SEQ ID NO 19
<211> LENGTH: 261
<212> TYPE: PRT
<213> ORGANISM: Bacillus subtilis

<400> SEQUENCE: 19

```
Met Tyr Pro Asp Leu Lys Gly Lys Val Val Ala Ile Thr Gly Ala Ala
1               5                   10                  15
Ser Gly Leu Gly Lys Ala Met Ala Ile Arg Phe Gly Lys Glu Gln Ala
            20                  25                  30
Lys Val Val Ile Asn Tyr Tyr Ser Asn Lys Gln Asp Pro Asn Glu Val
        35                  40                  45
Lys Glu Glu Val Ile Lys Ala Gly Gly Glu Ala Val Val Val Gln Ala
    50                  55                  60
Asp Val Thr Lys Glu Glu Asp Val Lys Asn Ile Val Gln Thr Ala Ile
65                  70                  75                  80
Asn Glu Phe Gly Thr Leu Asp Ile Met Ile Asn Asn Ala Gly Leu Glu
                85                  90                  95
Asn Pro Val Pro Ser His Glu Met Pro Leu Lys Asp Trp Asp Lys Val
            100                 105                 110
Ile Ser Thr Asn Leu Thr Gly Ala Phe Leu Gly Ser Arg Glu Ala Ile
        115                 120                 125
Lys Tyr Phe Val Glu Asn Asp Ile Lys Gly Asn Val Ile Asn Met Ser
    130                 135                 140
Ser Val His Glu Val Ile Pro Trp Pro Leu Phe Val His Tyr Ala Ala
145                 150                 155                 160
Ser Lys Gly Gly Ile Lys Leu Met Thr Lys Thr Leu Ala Leu Glu Tyr
                165                 170                 175
Ala Pro Lys Gly Ile Arg Val Asn Asn Ile Gly Pro Gly Ala Ile Asn
            180                 185                 190
Thr Pro Ile Asn Ala Glu Lys Phe Ala Asp Pro Lys Gln Arg Ala Asp
        195                 200                 205
```

Val Glu Ser Met Ile Pro Met Gly Arg Leu Gly Glu Pro Glu Ile
210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Leu Tyr Pro Ser Phe
                245                 250                 255

Gln Ala Gly Arg Gly
            260

<210> SEQ ID NO 20
<211> LENGTH: 786
<212> TYPE: DNA
<213> ORGANISM: Bacillus subtilis

<400> SEQUENCE: 20

```
atgtatccgg atttaaaagg aaaagtcgtc gctattacag gagctgcttc aggattaggg      60
aaggcaatgg ccattcgctt cggcaaggag caggcaaaag tggttatcaa ctactacagc     120
aataagcagg atccgaacga ggtaaaggaa gaggtcatca aggcgggcgg tgaagctgtt     180
gtcgtccaag cggacgtaac aaaagaggaa gatgtaaaaa acatcgtcca aacagcgatt     240
aacgagttcg gtacactcga tattatgatt aataatgccg gtcttgaaaa tcccgttcct     300
tctcatgaaa tgccgctgaa ggattgggat aaagtaatca gcacgaactt aacgggcgcc     360
ttttaggaa gccgtgaagc gattaaatat tttgttgaaa acgatataaa aggaaatgtc     420
attaatatgt cgagcgtaca tgaagtgatt ccgtggccat atttgttca ctatgcggca     480
agtaaaggcg aatcaagct gatgacgaaa acattggcgc tggaatatgc gccgaaaggc     540
attcgtgtca acaatatcgg gccaggcgcg atcaacacgc caatcaatgc tgaaaaattt     600
gctgatccta gcagagagc agatgtgaaa gcatgattc cgatgggacg cctgggtgaa     660
ccggaggaaa ttgcggcagt agcagcctgg cttgcttcga aggaagccag ctacgtcaca     720
ggcatcacgt tattcgcgga cggcggtatg accctgtatc cttcattcca ggcaggccgc     780
ggttaa                                                                786
```

<210> SEQ ID NO 21
<211> LENGTH: 261
<212> TYPE: PRT
<213> ORGANISM: Bacillus subtilis

<400> SEQUENCE: 21

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
                20                  25                  30

Lys Val Val Ile Asn Tyr Tyr Ser Asn Lys Gln Asp Pro Asn Glu Val
            35                  40                  45

Lys Glu Glu Val Ile Lys Ala Gly Gly Glu Ala Val Val Gln Gly
        50                  55                  60

Asp Val Thr Lys Glu Glu Asp Val Lys Asn Ile Val Gln Thr Ala Ile
65                  70                  75                  80

Asn Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Arg Val
            100                 105                 110

Ile Ser Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
            130                 135                 140

Ser Val His Glu Val Ile Pro Trp Pro Leu Phe Val His Tyr Ala Ala
145                 150                 155                 160

Ser Lys Gly Gly Ile Lys Leu Met Thr Lys Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Arg Ala Asp
        195                 200                 205

Val Glu Ser Met Ile Pro Met Gly Arg Leu Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Leu Tyr Pro Ser Phe
                245                 250                 255

Gln Ala Gly Arg Gly
            260

<210> SEQ ID NO 22
<211> LENGTH: 786
<212> TYPE: DNA
<213> ORGANISM: Bacillus subtilis

<400> SEQUENCE: 22
atgtatccgg atttaaaagg aaaagtcgtc gctattacag agctgcttc aggattaggg      60 aaggcaatgg ccattcgctt cggcaaggag caggcaaaag tggttatcaa ctactacagc    120
aataagcagg atccgaacga ggtaaaggaa gaggtcatca aggcgggcgg tgaagctgtt    180
gtcgtccaag gagacgtaac aaaagaggaa gatgtaaaaa acatcgtcca aacagcgatt    240
aacgagttcg gtacactcga tattatgatt aataatgccg gtcttgaaaa tcccgttcct    300
tctcatgaaa tgccgctgaa ggattgggat cgcgtaatca gcacgaactt aacgggcgcc    360
tttttaggaa gccgtgaagc gattaaatat tttgttgaaa acgatataaa aggaaatgtc    420
attaatatgt cgagcgtaca tgaagtgatt ccgtggccat atttgttca ctatgcggca    480 agtaaaggcg gaatcaagct gatgacgaaa acattggcgc tggaatatgc ccgaaaggc    540 attcgtgtca acaatatcgg gccaggcgcg atcaacacgc caatcaatgc tgaaaaattt    600
gctgatccta gcagagagc agatgtgaaa agcatgattc cgatgggacg cctgggtgaa    660
ccggaggaaa ttgcggcagt agcagcctgg cttgcttcga aggaagccag ctacgtcaca    720
ggcatcacgt tattcgcgga cggcggtatg accctgtatc cttcattcca ggcaggccgc    780
ggttaa                                                              786

<210> SEQ ID NO 23
<211> LENGTH: 261
<212> TYPE: PRT
<213> ORGANISM: Bacillus subtilis

<400> SEQUENCE: 23

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val

```
                35                  40                  45
Lys Glu Glu Val Ile Lys Ala Gly Gly Glu Ala Val Val Gln Gly
     50                  55                  60

Asp Val Thr Lys Glu Glu Asp Val Lys Asn Ile Val Gln Thr Ala Ile
 65                  70                  75                  80

Asn Glu Phe Gly Thr Leu Asp Ile Met Ile Asn Asn Ala Gly Leu Glu
                 85                  90                  95

Asn Pro Val Pro Ser His Glu Met Pro Leu Lys Asp Trp Asp Lys Val
             100                 105                 110

Ile Ser Thr Asn Leu Thr Gly Ala Phe Leu Gly Ser Arg Glu Ala Ile
         115                 120                 125

Lys Tyr Phe Val Glu Asn Asp Ile Lys Gly Asn Val Ile Asn Met Ser
     130                 135                 140

Ser Val His Glu Val Ile Pro Trp Pro Leu Phe Val His Tyr Ala Ala
 145                 150                 155                 160

Ser Lys Gly Gly Ile Lys Leu Met Thr Lys Thr Leu Ala Leu Glu Tyr
                 165                 170                 175

Ala Pro Tyr Gly Ile Arg Val Asn Asn Ile Gly Pro Gly Ala Ile Asn
             180                 185                 190

Thr Pro Ile Asn Ala Glu Lys Phe Ala Asp Pro Lys Gln Arg Ala Asp
         195                 200                 205

Val Glu Ser Met Ile Pro Met Gly Arg Leu Gly Glu Pro Glu Glu Ile
     210                 215                 220

Ala Ala Val Ala Ala Trp Leu Ala Ser Lys Glu Ala Ser Tyr Val Thr
 225                 230                 235                 240

Gly Ile Thr Leu Phe Ala Asp Gly Gly Met Thr Leu Tyr Pro Ser Phe
                 245                 250                 255

Gln Ala Gly Arg Gly
             260

<210> SEQ ID NO 24
<211> LENGTH: 786
<212> TYPE: DNA
<213> ORGANISM: Bacillus subtilis

<400> SEQUENCE: 24
atgtatccgg atttaaaagg aaaagtcgtc gctattacag gagctgcttc aggattaggg      60
aaggcaatgg ccattcgctt cggcaaggag caggcaaaag tggttatcaa ctactacagc     120
aataagcagg atccgaacga ggtaaaggaa gaggtcatca aggcgggcgg tgaagctgtt     180
gtcgtccaag gagacgtaac aaaagaggaa gatgtaaaaa acatcgtcca acagcgatt     240 aacgagttcg gtacactcga tattatgatt aataatgccg gtcttgaaaa tcccgttcct     300
tctcatgaaa tgccgctgaa ggattgggat aaagtaatca gcacgaactt aacgggcgcc     360 ttttaggaa gccgtgaagc gattaaatat tttgttgaaa acgatataaa aggaaatgtc     420
attaatatgt cgagcgtaca tgaagtgatt ccgtggccat tatttgttca ctatgcggca     480
agtaaaggcg gaatcaagct gatgacgaaa acattggcgc tggaatatgc gccgtatggc     540
attcgtgtca acaatatcgg gccaggcgcg atcaacacgc caatcaatgc tgaaaaattt     600
gctgatccta agcagagagc agatgtagaa agcatgattc cgatgggacg cctgggtgaa     660
ccggaggaaa ttgcggcagt agcagcctgg cttgcttcga aggaagccag ctacgtcaca     720
ggcatcacgt tattcgcgga cggcggtatg accctgtatc cttcattcca ggcaggccgc     780
ggttaa                                                                786
```

<210> SEQ ID NO 25
<211> LENGTH: 261
<212> TYPE: PRT
<213> ORGANISM: Bacillus subtilis

<400> SEQUENCE: 25

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Gln Gly
    50                  55                  60

Asp Val Thr Lys Glu Glu Asp Val Lys Asn Ile Val Gln Thr Ala Ile
65                  70                  75                  80

Asn Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Ser Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Ile Lys Leu Met Thr Lys Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Arg Ala Asp
        195                 200                 205

Val Glu Ser Met Ile Pro Met Gly Arg Leu Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Val Asp Gly Gly Met Thr Leu Tyr Pro Ser Phe
                245                 250                 255

Gln Ala Gly Arg Gly
            260

<210> SEQ ID NO 26
<211> LENGTH: 786
<212> TYPE: DNA
<213> ORGANISM: Bacillus subtilis

<400> SEQUENCE: 26
atgtatccgg atttaaaagg aaaagtcgtc gctattacag gagctgcttc aggattaggg      60
aaggcaatgg ccattcgctt cggcaaggag caggcaaaag tggttatcaa ctactacagc     120
aataagcagg atccgaacga ggtaaaggaa gaggtcatca aggcgggcgg tgaagctgtt     180
gtcgtccaag gagacgtaac aaaagaggaa gatgtaaaaa acatcgtcca acagcgatt      240 aacgagttcg gtacactcga tattatgatt aataatgccg gtcttgaaaa tcccgttcct     300
tctcatgaaa tgccgctgaa ggattgggat aaagtaatca gcacgaactt aacgggcgcc     360

```
tttttaggaa gccgtgaagc gattaaatat tttgttgaaa acgatataaa aggaaatgtc      420
attaatatgt cgagcgtaca tgaagtgatt ccgtggccat tatttgttca ctatgcggca      480
agtaaaggcg gaatcaagct gatgacgaaa acattggcgc tggaatatgc gccgaaaggc      540
attcgtgtca acaatatcgg gccaggcgcg atcaacacgc caatcaatgc tgaaaaattt      600
gctgatccta agcagagagc agatgtagaa agcatgattc cgatgggacg cctgggtgaa      660
ccggaggaaa ttgcggcagt agcagcctgg cttgcttcga aggaagccag ctacgtcaca      720
ggcatcacgt tattcgtgga cggcggtatg accctgtatc cttcattcca ggcaggccgc      780
ggttaa                                                                 786
```

<210> SEQ ID NO 27
<211> LENGTH: 261
<212> TYPE: PRT
<213> ORGANISM: Bacillus subtilis

<400> SEQUENCE: 27

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Gln Gly
    50                  55                  60

Asp Val Thr Lys Glu Glu Asp Val Lys Asn Ile Val Gln Thr Ala Ile
65                  70                  75                  80

Asn Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Ser Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Cys Ala
145                 150                 155                 160

Ser Lys Gly Gly Ile Lys Leu Met Thr Lys Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Arg Ala Asp
        195                 200                 205

Val Glu Ser Met Ile Pro Met Gly Arg Leu Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Leu Tyr Pro Ser Phe
                245                 250                 255

Gln Ala Gly Arg Gly
            260
```

<210> SEQ ID NO 28
<211> LENGTH: 786

<212> TYPE: DNA
<213> ORGANISM: Bacillus subtilis

<400> SEQUENCE: 28

```
atgtatccgg atttaaaagg aaaagtcgtc gctattacag gagctgcttc aggattaggg      60
aaggcaatgg ccattcgctt cggcaaggag caggcaaaag tggttatcaa ctactacagc     120
aataagcagg atccgaacga ggtaaaggaa gaggtcatca aggcgggcgg tgaagctgtt     180
gtcgtccaag gagacgtaac aaaagaggaa gatgtaaaaa acatcgtcca aacagcgatt     240
aacgagttcg gtacactcga tattatgatt aataatgccg gtcttgaaaa tcccgttcct     300
tctcatgaaa tgccgctgaa ggattgggat aaagtaatca gcacgaactt aacgggcgcc     360
tttttaggaa gccgtgaagc gattaaatat tttgttgaaa acgatataaa aggaaatgtc     420
attaatatgt cgagcgtaca tgaagtgatt ccgtggccat tatttgttca ctattgcgca     480
agtaaaggcg gaatcaagct gatgacgaaa acattggcgc tggaatatgc gccgaaaggc     540
attcgtgtca acaatatcgg gccaggcgcg atcaacacgc caatcaatgc tgaaaaattt     600
gctgatccta gcagagagc agatgtagaa agcatgattc cgatgggacg cctgggtgaa     660
ccggaggaaa ttgcggcagt agcagcctgg cttgcttcga aggaagccag ctacgtcaca     720
ggcatcacgt tattcgcgga cggcggtatg accctgtatc cttcattcca ggcaggccgc     780
ggttaa                                                                786
```

<210> SEQ ID NO 29
<211> LENGTH: 261
<212> TYPE: PRT
<213> ORGANISM: Bacillus subtilis

<400> SEQUENCE: 29

```
Met Tyr Pro Asp Leu Lys Gly Lys Val Val Ala Ile Thr Gly Ala Ala
 1               5                  10                  15
Ser Gly Leu Gly Lys Ala Met Ala Ile Arg Phe Gly Lys Glu Gly Ala
            20                  25                  30
Lys Val Val Ile Asn Tyr Tyr Ser Asn Lys Gln Asp Pro Asn Glu Val
        35                  40                  45
Lys Glu Glu Val Ile Lys Ala Gly Gly Glu Ala Val Val Val Gln Gly
    50                  55                  60
Asp Val Thr Lys Glu Glu Asp Val Lys Asn Ile Val Gln Thr Ala Ile
65                  70                  75                  80
Asn Glu Phe Gly Thr Leu Asp Ile Met Ile Asn Asn Ala Gly Leu Glu
                85                  90                  95
Asn Pro Val Pro Ser His Glu Met Pro Leu Lys Asp Trp Asp Lys Val
            100                 105                 110
Ile Ser Thr Asn Leu Thr Gly Ala Phe Leu Gly Ser Arg Glu Ala Ile
        115                 120                 125
Lys Tyr Phe Val Glu Asn Asp Ile Lys Gly Asn Val Ile Asn Met Ser
    130                 135                 140
Ser Val His Glu Val Ile Pro Trp Pro Leu Phe Val His Tyr Cys Ala
145                 150                 155                 160
Ser Lys Gly Gly Ile Lys Leu Met Thr Lys Thr Leu Ala Leu Glu Tyr
                165                 170                 175
Ala Pro Lys Gly Ile Arg Val Asn Asn Ile Gly Pro Gly Ala Ile Asn
            180                 185                 190
Thr Pro Ile Asn Ala Glu Lys Phe Ala Asp Pro Lys Gln Arg Ala Asp
        195                 200                 205
```

Val Glu Ser Met Ile Pro Met Gly Arg Leu Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Leu Tyr Pro Ser Phe
                245                 250                 255

Gln Ala Gly Arg Gly
            260

<210> SEQ ID NO 30
<211> LENGTH: 786
<212> TYPE: DNA
<213> ORGANISM: Bacillus subtilis

<400> SEQUENCE: 30
atgtatccgg atttaaaagg aaaagtcgtc gctattacag gagctgcttc aggattaggg      60
aaggcaatgg ccattcgctt cggcaaggag ggtgcaaaag tggttatcaa ctactacagc     120
aataagcagg atccgaacga ggtaaaggaa gaggtcatca aggcgggcgg tgaagctgtt     180
gtcgtccaag gagacgtaac aaaagaggaa gatgtaaaaa acatcgtcca aacagcgatt     240
aacgagttcg gtacactcga tattatgatt aataatgccg gtcttgaaaa tcccgttcct     300
tctcatgaaa tgccgctgaa ggattgggat aaagtaatca gcacgaactt aacgggcgcc     360
tttttaggaa gccgtgaagc gattaaatat tttgttgaaa cgatataaa ggaaatgtc      420 attaatatgt cgagcgtaca tgaagtgatt ccgtggccat tatttgttca ctattgcgca     480
agtaaaggcg gaatcaagct gatgacgaaa acattggcgc tggaatatgc gccgaaaggc     540
attcgtgtca acaatatcgg gccaggcgcg atcaacacgc caatcaatgc tgaaaaattt     600
gctgatccta agcagagagc agatgtagaa agcatgattc cgatgggacg cctgggtgaa     660
ccggaggaaa ttgcggcagt agcagcctgg cttgcttcga aggaagccag ctacgtcaca     720
ggcatcacgt tattcgcgga cggcggtatg accctgtatc cttcattcca ggcaggccgc     780
ggttaa                                                                 786

<210> SEQ ID NO 31
<211> LENGTH: 261
<212> TYPE: PRT
<213> ORGANISM: Bacillus subtilis

<400> SEQUENCE: 31

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Ala
    50                  55                  60

Asp Val Thr Lys Glu Glu Asp Val Lys Asn Ile Val Gln Thr Ala Ile
65                  70                  75                  80

Asn Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Ser Thr Asn Leu Thr Gly Ala Phe Leu Gly Ser Arg Glu Ala Ile

```
            115                 120                 125
Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Cys Ala
145                 150                 155                 160

Ser Lys Gly Gly Ile Lys Leu Met Thr Lys Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Arg Ala Asp
        195                 200                 205

Val Glu Ser Met Ile Pro Met Gly Arg Leu Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Leu Tyr Pro Ser Phe
                245                 250                 255

Gln Ala Gly Arg Gly
            260

<210> SEQ ID NO 32
<211> LENGTH: 786
<212> TYPE: DNA
<213> ORGANISM: Bacillus subtilis

<400> SEQUENCE: 32
atgtatccgg atttaaaagg aaaagtcgtc gctattacag gagctgcttc aggattaggg    60
aaggcaatgg ccattcgctt cggcaaggag caggcaaaag tggttatcaa ctactacagc   120
aataagcagg atccgaacga ggtaaaggaa gaggtcatca aggcgggcgg tgaagctgtt   180
gtcgtccaag cggacgtaac aaaagaggaa gatgtaaaaa acatcgtcca aacagcgatt   240
aacgagttcg gtacactcga tattatgatt aataatgccg gtcttgaaaa tcccgttcct   300
tctcatgaaa tgccgctgaa ggattgggat aaagtaatca gcacgaactt aacgggcgcc   360
tttttaggaa gccgtgaagc gattaaatat tttgttgaaa cgatataaa ggaaatgtc    420
attaatatgt cgagcgtaca tgaagtgatt ccgtggccat atttgttca ctattgcgca    480
agtaaaggcg gaatcaagct gatgacgaaa acattggcgc tggaatatgc gccgaaaggc   540
attcgtgtca acaatatcgg gccaggcgcg atcaacacgc caatcaatgc tgaaaaattt   600
gctgatccta gcagagagc agatgtgaa agcatgatc cgatgggacg cctgggtgaa    660
ccggaggaaa ttgcggcagt agcagcctgg cttgcttcga aggaagccag ctacgtcaca   720
ggcatcacgt tattcgcgga cggcggtatg accctgtatc cttcattcca ggcaggccgc   780
ggttaa                                                              786

<210> SEQ ID NO 33
<211> LENGTH: 261
<212> TYPE: PRT
<213> ORGANISM: Bacillus subtilis

<400> SEQUENCE: 33

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30
```

Lys Val Val Ile Asn Tyr Tyr Ser Asn Lys Gln Asp Pro Asn Glu Val
            35                  40                  45

Lys Glu Glu Val Ile Lys Ala Gly Gly Glu Ala Val Val Gln Gly
 50                  55                  60

Asp Val Thr Lys Glu Glu Asp Val Lys Asn Ile Val Gln Thr Ala Ile
 65                  70                  75                  80

Asn Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Arg Val
            100                 105                 110

Ile Ser Thr Asn Leu Thr Gly Ala Phe Leu Gly Ser Arg Glu Ala Ile
            115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Cys Ala
145                 150                 155                 160

Ser Lys Gly Gly Ile Lys Leu Met Thr Lys Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Arg Ala Asp
            195                 200                 205

Val Glu Ser Met Ile Pro Met Gly Arg Leu Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Leu Tyr Pro Ser Phe
                245                 250                 255

Gln Ala Gly Arg Gly
            260

<210> SEQ ID NO 34
<211> LENGTH: 786
<212> TYPE: DNA
<213> ORGANISM: Bacillus subtilis

<400> SEQUENCE: 34
atgtatccgg atttaaaagg aaaagtcgtc gctattacag agctgcttc aggattaggg      60 aaggcaatgg ccattcgctt cggcaaggag caggcaaaag tggttatcaa ctactacagc    120
aataagcagg atccgaacga ggtaaaggaa gaggtcatca aggcgggcgg tgaagctgtt    180
gtcgtccaag agacgtaac aaaagaggaa gatgtaaaaa acatcgtcca acagcgatt     240 aacgagttcg gtacactcga tattatgatt aataatgccg gtcttgaaaa tcccgttcct    300
tctcatgaaa tgccgctgaa ggattgggat cgcgtaatca gcacgaactt aacgggcgcc    360 ttttaggaa gccgtgaagc gattaaatat tttgttgaaa acgatataaa aggaaatgtc    420
attaatatgt cgagcgtaca tgaagtgatt ccgtggccat atttgttca ctattgcgca    480 agtaaaggcg gaatcaagct gatgacgaaa acattggcgc tggaatatgc gccgaaaggc    540
attcgtgtca acaatatcgg gccaggcgcg atcaacacgc caatcaatgc tgaaaaattt    600
gctgatccta agcagagagc agatgtagaa agcatgattc cgatgggacg cctgggtgaa    660
ccggaggaaa ttgcggcagt agcagcctgg cttgcttcga aggaagccag ctacgtcaca    720
ggcatcacgt tattcgcgga cggcggtatg accctgtatc cttcattcca ggcaggccgc    780
ggttaa                                                                  786

<210> SEQ ID NO 35
<211> LENGTH: 261
<212> TYPE: PRT
<213> ORGANISM: Bacillus subtilis

<400> SEQUENCE: 35

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Gln Gly
    50                  55                  60

Asp Val Thr Lys Glu Glu Asp Val Lys Asn Ile Val Gln Thr Ala Ile
65                  70                  75                  80

Asn Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Ser Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Cys Ala
145                 150                 155                 160

Ser Lys Gly Gly Ile Lys Leu Met Thr Lys Thr Leu Ala Leu Glu Tyr
                165                 170                 175

Ala Pro Tyr Gly Ile Arg Val Asn Asn Ile Gly Pro Gly Ala Ile Asn
            180                 185                 190

Thr Pro Ile Asn Ala Glu Lys Phe Ala Asp Pro Lys Gln Arg Ala Asp
        195                 200                 205

Val Glu Ser Met Ile Pro Met Gly Arg Leu Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Leu Tyr Pro Ser Phe
                245                 250                 255

Gln Ala Gly Arg Gly
            260

<210> SEQ ID NO 36
<211> LENGTH: 786
<212> TYPE: DNA
<213> ORGANISM: Bacillus subtilis

<400> SEQUENCE: 36
atgtatccgg atttaaaagg aaaagtcgtc gctattacag gagctgcttc aggattaggg      60
aaggcaatgg ccattcgctt cggcaaggag caggcaaaag tggttatcaa ctactacagc     120
aataagcagg atccgaacga ggtaaaggaa gaggtcatca aggcgggcgg tgaagctgtt     180
gtcgtccaag gagacgtaac aaaagaggaa gatgtaaaaa acatcgtcca acacagcgatt    240 aacgagttcg gtacactcga tattatgatt aataatgccg gtcttgaaaa tcccgttcct     300

```
tctcatgaaa tgccgctgaa ggattgggat aaagtaatca gcacgaactt aacgggcgcc    360
tttttaggaa gccgtgaagc gattaaatat tttgttgaaa acgatataaa aggaaatgtc    420
attaatatgt cgagcgtaca tgaagtgatt ccgtggccat tatttgttca ctattgcgca    480
agtaaaggcg gaatcaagct gatgacgaaa acattggcgc tggaatatgc gccgtatggc    540
attcgtgtca caatatcgg ccaggcgcg atcaacacgc caatcaatgc tgaaaaattt    600
gctgatccta agcagagagc agatgtagaa agcatgattc cgatgggacg cctgggtgaa    660
ccggaggaaa ttgcggcagt agcagcctgg cttgcttcga aggaagccag ctacgtcaca    720
ggcatcacgt tattcgcgga cggcggtatg accctgtatc cttcattcca ggcaggccgc    780
ggttaa                                                                786
```

<210> SEQ ID NO 37
<211> LENGTH: 261
<212> TYPE: PRT
<213> ORGANISM: Bacillus subtilis

<400> SEQUENCE: 37

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
                20                  25                  30

Lys Val Val Ile Asn Tyr Tyr Ser Asn Lys Gln Asp Pro Asn Glu Val
            35                  40                  45

Lys Glu Glu Val Ile Lys Ala Gly Gly Glu Ala Val Val Gln Gly
        50                  55                  60

Asp Val Thr Lys Glu Glu Asp Val Lys Asn Ile Val Gln Thr Ala Ile
65                  70                  75                  80

Asn Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Ser Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Cys Ala
145                 150                 155                 160

Ser Lys Gly Gly Ile Lys Leu Met Thr Lys Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Arg Ala Asp
        195                 200                 205

Val Glu Ser Met Ile Pro Met Gly Arg Leu Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Val Asp Gly Gly Met Thr Leu Tyr Pro Ser Phe
                245                 250                 255

Gln Ala Gly Arg Gly
            260
```

<210> SEQ ID NO 38

<211> LENGTH: 786
<212> TYPE: DNA
<213> ORGANISM: Bacillus subtilis

<400> SEQUENCE: 38

```
atgtatccgg atttaaaagg aaaagtcgtc gctattacag gagctgcttc aggattaggg      60
aaggcaatgg ccattcgctt cggcaaggag caggcaaaag tggttatcaa ctactacagc     120
aataagcagg atccgaacga ggtaaaggaa gaggtcatca aggcgggcgg tgaagctgtt     180
gtcgtccaag gagacgtaac aaaagaggaa gatgtaaaaa acatcgtcca acagcgattt     240
aacgagttcg gtacactcga tattatgatt aataatgccg gtcttgaaaa tcccgttcct     300
tctcatgaaa tgccgctgaa ggattgggat aaagtaatca gcacgaactt aacgggcgcc     360
ttttaggaa gccgtgaagc gattaaatat tttgttgaaa acgatataaa aggaaatgtc     420
attaatatgt cgagcgtaca tgaagtgatt ccgtggccat atttgttca ctattgcgca     480
agtaaaggcg gaatcaagct gatgacgaaa acattggcgc tggaatatgc gccgaaaggc     540
attcgtgtca acaatatcgg gccaggcgcg atcaacacgc caatcaatgc tgaaaaattt     600
gctgatccta gcagagagc agatgtagaa agcatgattc cgatgggacg cctgggtgaa     660
ccggaggaaa ttgcggcagt agcagcctgg cttgcttcga aggaagccag ctacgtcaca     720
ggcatcacgt tattcgtgga cggcggtatg accctgtatc cttcattcca ggcaggccgc     780
ggttaa                                                                 786
```

<210> SEQ ID NO 39
<211> LENGTH: 261
<212> TYPE: PRT
<213> ORGANISM: Bacillus subtilis

<400> SEQUENCE: 39

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Gln Ala
    50                  55                  60

Asp Val Thr Lys Glu Glu Asp Val Lys Asn Ile Val Gln Thr Ala Ile
65                  70                  75                  80

Asn Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Arg Val
            100                 105                 110

Ile Ser Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Cys Ala
145                 150                 155                 160

Ser Lys Gly Gly Ile Lys Leu Met Thr Lys Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Arg Ala Asp
```

```
              195                 200                 205
Val Glu Ser Met Ile Pro Met Gly Arg Leu Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Leu Tyr Pro Ser Phe
                245                 250                 255

Gln Ala Gly Arg Gly
            260

<210> SEQ ID NO 40
<211> LENGTH: 786
<212> TYPE: DNA
<213> ORGANISM: Bacillus subtilis

<400> SEQUENCE: 40
atgtatccgg atttaaaagg aaaagtcgtc gctattacag gagctgcttc aggattaggg      60
aaggcaatgg ccattcgctt cggcaaggag caggcaaaag tggttatcaa ctactacagc     120
aataagcagg atccgaacga ggtaaaggaa gaggtcatca aggcgggcgg tgaagctgtt     180
gtcgtccaag cggacgtaac aaaagaggaa gatgtaaaaa acatcgtcca aacagcgatt     240
aacgagttcg gtacactcga tattatgatt aataatgccg gtcttgaaaa tcccgttcct     300
tctcatgaaa tgccgctgaa ggattgggat cgcgtaatca gcacgaactt aacgggcgcc     360 ttttaggaa gccgtgaagc gattaaatat tttgttgaaa acgatataaa aggaaatgtc     420
attaatatgt cgagcgtaca tgaagtgatt ccgtggccat tatttgttca ctattgcgca     480
agtaaaggcg aatcaagct gatgacgaaa acattggcgc tggaatatgc gccgaaaggc     540
attcgtgtca acaatatcgg gccaggcgcg atcaacacgc caatcaatgc tgaaaaattt     600
gctgatccta agcagagagc agatgtagaa agcatgattc cgatgggacg cctgggtgaa     660
ccggaggaaa ttgcggcagt agcagcctgg cttgcttcga aggaagccag ctacgtcaca     720
ggcatcacgt tattcgcgga cggcggtatg accctgtatc cttcattcca ggcaggccgc     780
ggttaa                                                                786

<210> SEQ ID NO 41
<211> LENGTH: 261
<212> TYPE: PRT
<213> ORGANISM: Bacillus subtilis

<400> SEQUENCE: 41

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gly Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Gln Ala
    50                  55                  60

Asp Val Thr Lys Glu Glu Asp Val Lys Asn Ile Val Gln Thr Ala Ile
65                  70                  75                  80

Asn Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110
```

```
Ile Ser Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Cys Ala
145                 150                 155                 160

Ser Lys Gly Gly Ile Lys Leu Met Thr Lys Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Arg Ala Asp
        195                 200                 205

Val Glu Ser Met Ile Pro Met Gly Arg Leu Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Leu Tyr Pro Ser Phe
                245                 250                 255

Gln Ala Gly Arg Gly
            260
```

<210> SEQ ID NO 42
<211> LENGTH: 786
<212> TYPE: DNA
<213> ORGANISM: Bacillus subtilis

<400> SEQUENCE: 42

```
atgtatccgg atttaaaagg aaaagtcgtc gctattacag gagctgcttc aggattaggg      60
aaggcaatgg ccattcgctt cggcaaggag ggtgcaaaag tggttatcaa ctactacagc     120
aataagcagg atccgaacga ggtaaaggaa gaggtcatca aggcgggcgg tgaagctgtt     180
gtcgtccaag cggacgtaac aaaagaggaa gatgtaaaaa acatcgtcca acagcgatt      240
aacgagttcg gtacactcga tattatgatt aataatgccg gtcttgaaaa tcccgttcct     300
tctcatgaaa tgccgctgaa ggattgggat aaagtaatca gcacgaactt aacgggcgcc     360
ttttaggaa gccgtgaagc gattaaatat tttgttgaaa acgatataaa aggaaatgtc      420
attaatatgt cgagcgtaca tgaagtgatt ccgtggccat atttgttca ctattgcgca      480
agtaaaggcg gaatcaagct gatgacgaaa acattggcgc tggaatatgc ccgaaaggc     540
attcgtgtca acaatatcgg gccaggcgcg atcaacacgc caatcaatgc tgaaaaattt     600
gctgatccta gcagagagc agatgtagaa agcatgattc cgatgggacg cctgggtgaa     660
ccggaggaaa ttgcggcagt agcagcctgg cttgcttcga aggaagccag ctacgtcaca     720
ggcatcacgt tattcgcgga cggcggtatg accctgtatc cttcattcca ggcaggccgc     780
ggttaa                                                                786
```

<210> SEQ ID NO 43
<211> LENGTH: 261
<212> TYPE: PRT
<213> ORGANISM: Bacillus subtilis

<400> SEQUENCE: 43

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30
```

Lys Val Ile Asn Tyr Tyr Ser Asn Lys Gln Asp Pro Asn Glu Val
    35                  40                  45

Lys Glu Glu Val Ile Lys Ala Gly Gly Glu Ala Val Val Gln Gly
    50                  55                  60

Asp Val Thr Lys Glu Glu Asp Val Lys Asn Ile Val Gln Thr Ala Ile
65                  70                  75                  80

Asn Glu Phe Gly Thr Leu Asp Ile Met Ile Asn Asn Ala Gly Leu Glu
                    85                  90                  95

Asn Pro Val Pro Ser His Glu Met Pro Leu Lys Asp Trp Asp Lys Val
                100                 105                 110

Ile Ser Thr Asn Leu Thr Gly Ala Phe Leu Gly Ser Arg Glu Ala Ile
                115                 120                 125

Lys Tyr Phe Val Lys Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Ile Lys Leu Met Thr Lys Thr Leu Ala Leu Glu Tyr
                    165                 170                 175

Ala Pro Lys Gly Ile Arg Val Asn Asn Ile Gly Pro Gly Ala Ile Asn
                180                 185                 190

Thr Pro Ile Asn Ala Glu Lys Phe Ala Asp Pro Lys Gln Arg Ala Asp
                195                 200                 205

Val Glu Ser Met Ile Pro Met Gly Tyr Ile Gly Glu Pro Glu Glu Ile
                210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Leu Tyr Pro Ser Phe
                    245                 250                 255

Gln Ala Gly Arg Gly
                260

<210> SEQ ID NO 44
<211> LENGTH: 786
<212> TYPE: DNA
<213> ORGANISM: Bacillus subtilis

<400> SEQUENCE: 44
atgtatccgg atttaaaagg aaaagtcgtc gctattacag gagctgcttc aggattaggg    60
aaggcaatgg ccattcgctt cggcaaggag caggcaaaag tggttatcaa ctactacagc   120
aataagcagg atccgaacga ggtaaaggaa gaggtcatca aggcgggcgg tgaagctgtt   180
gtcgtccaag gagacgtaac aaaagaggaa gatgtaaaaa acatcgtcca acagcgatt    240 aacgagttcg gtacactcga tattatgatt aataatgccg gtcttgaaaa tcccgttcct   300
tctcatgaaa tgccgctgaa ggattgggat aaagtaatca gcacgaactt aacgggcgcc   360 ttttaggaa gccgtgaagc gattaaatat tttgttaaga acgatataaa aggaaatgtc    420
attaatatgt cgagcgtaca tgaagtgatt ccgtggccat atttgttca ctatgcggca    480 agtaaaggcg gaatcaagct gatgacgaaa acattggcgc tggaatatgc ccgaaaggc    540 attcgtgtca acaatatcgg gccaggcgcg atcaacacgc caatcaatgc tgaaaaattt   600
gctgatccta gcagagagc agatgtgaaa agcatgattc cgatgggata tatcggtgaa    660
ccggaggaaa ttgcggcagt agcagcctgg cttgcttcga aggaagccag ctacgtcaca   720
ggcatcacgt tattcgcgga cggcggtatg accctgtatc cttcattcca ggcaggccgc   780
ggttaa                                                                786

<210> SEQ ID NO 45
<211> LENGTH: 261
<212> TYPE: PRT
<213> ORGANISM: Bacillus subtilis

<400> SEQUENCE: 45

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Asn Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Ser Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Ile Lys Leu Met Thr Lys Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Arg Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Leu Tyr Pro Ser Phe
                245                 250                 255

Gln Ala Gly Arg Gly
            260

<210> SEQ ID NO 46
<211> LENGTH: 786
<212> TYPE: DNA
<213> ORGANISM: Bacillus subtilis

<400> SEQUENCE: 46
atgtatccgg atttaaaagg aaaagtcgtc gctattacag agctgcttc aggattaggg      60 aaggcaatgg ccattcgctt cggcaaggag caggcaaaag tggttatcaa ctactacagc    120
aataagcagg atccgaacga ggtaaaggaa gaggtcatca aggcgggcgg tgaagctgtt    180
gtcgtccaag gagacgtaac aaaagaggaa gatgtaaaaa acatcgtcca acagcgatt     240 aacgagttcg gtacactcga tattatgatt aataatgccg gtcttgaaaa tcccgttcct    300

```
tctcatgaaa tgccgctgaa ggattgggat aaagtaatca gcacgaactt aacgggcgcc      360
tttttaggaa gccgtgaagc gattaaatat tttgttgaaa acgatataaa aggaaatgtc      420
attaatatgt cgagcgtaca tgaagtgatt ccgtggccat tatttgttca ctatgcggca      480
agtaaaggcg gaatcaagct gatgacgaaa acattggcgc tggaatatgc gccgaaaggc      540
attcgtgtca acaatatcgg gccaggcgcg atcaacacgc caatcaatgc tgaaaaattt      600
gctgatccta agcagagagc agatgtgaaa agcatgattc cgatgggata tatcggtgaa      660
ccggaggaaa ttgcggcagt agcagcctgg cttgcttcga aggaagccag ctacgtcaca      720
ggcatcacgt tattcgcgga cggcggtatg accctgtatc cttcattcca ggcaggccgc      780
ggttaa                                                                 786

<210> SEQ ID NO 47
<211> LENGTH: 261
<212> TYPE: PRT
<213> ORGANISM: Bacillus subtilis

<400> SEQUENCE: 47

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Ala Glu Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Asn Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Ser Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Tyr Val His Tyr Ala Ala
145                 150                 155                 160

Ser Lys Gly Gly Ile Lys Leu Met Thr Lys Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Arg Ala Asp
        195                 200                 205

Val Glu Ser Met Ile Pro Met Gly Tyr Ile Gly Glu Pro Glu Glu Ile
    210                 215                 220

Ala Ala Ala Ala Ala Phe Leu Ala Ser Lys Glu Ala Ser Tyr Val Thr
225                 230                 235                 240

Gly Ile Thr Leu Phe Ala Asp Gly Gly Met Thr Leu Tyr Pro Ser Phe
                245                 250                 255

Gln Ala Gly Arg Gly
            260
```

<210> SEQ ID NO 48
<211> LENGTH: 786
<212> TYPE: DNA
<213> ORGANISM: Bacillus subtilis

<400> SEQUENCE: 48

```
atgtatccgg atttaaaagg aaaagtcgtc gctattacag gagctgcttc aggattaggg      60
aaggcaatgg ccattcgctt cggcaaggag caggcaaaag tggttatcaa ctactacagc     120
aataagcagg atgctgaaga ggtaaaggaa gaggtcatca aggcgggcgg tgaagctgtt     180
gtcgtccaag agacgtaac aaaagaggaa gatgtaaaaa acatcgtcca acagcgatt      240
aacgagttcg gtacactcga tattatgatt aataatgccg gtcttgaaaa tcccgttcct     300
tctcatgaaa tgccgctgaa ggattgggat aaagtaatca gcacgaactt aacgggcgcc     360
tttttaggaa gccgtgaagc gattaaatat tttgttgaaa acgatataaa aggaaatgtc     420
attaatatgt cgagcgtaca tgaagtgatt ccgtggccat atacgttca ctatgcggca      480
agtaaaggcg aatcaagct gatgacgaaa acattggcgc tggaatatgc gccgaaaggc     540
attcgtgtca acaatatcgg gccaggcgcg atcaacacgc caatcaatgc tgaaaaattt     600
gctgatccta gcagagagc agatgtgaaa agcatgattc cgatgggata tatcggtgaa     660
ccggaggaaa ttgcggcagc tgcagccttc cttgcttcga aggaagccag ctacgtcaca     720
ggcatcacgt tattcgcgga cggcggtatg accctgtatc cttcattcca ggcaggccgc     780
ggttaa                                                                786
```

<210> SEQ ID NO 49
<211> LENGTH: 296
<212> TYPE: PRT
<213> ORGANISM: Artificial Sequence
<220> FEATURE:
<223> OTHER INFORMATION: Calculated ancestral sequence

<400> SEQUENCE: 49

```
Met Val Lys Glu Val Phe Glu Met Ile Thr Val Tyr Ala Arg Ala Leu
1               5                   10                  15

Ala Glu Arg Ile Met Ser Ala Asn Met Gly Ser Met Met Glu Ala Arg
            20                  25                  30

Leu Ser Gly Lys Val Ala Leu Val Thr Gly Ala Ser Ser Gly Ile Gly
        35                  40                  45

Lys Ala Ile Ala Leu Arg Leu Ala Gln Glu Gly Ala Lys Gly Val Val
    50                  55                  60

Val Asn Tyr Arg Ser His Lys Glu Ala Asp Glu Ile Val Glu Glu
65                  70                  75                  80

Ile Lys Lys Ala Gly Gly Glu Ala Met Ala Val Gln Ala Asp Val Ser
                85                  90                  95

Lys Glu Ala Glu Asp Val Gln Lys Leu Val Glu Gln Thr Val Asp Ala
            100                 105                 110

Phe Gly Arg Leu Asp Ile Leu Val Asn Asn Ala Gly Ile Glu Ser Pro
        115                 120                 125

Lys Ala Pro Val His Glu Met Thr Pro Glu Asp Trp Asp Arg Val Ile
    130                 135                 140

Asp Val Asn Leu Lys Gly Val Phe Leu Cys Thr Arg Glu Ala Val Lys
145                 150                 155                 160

His Met Ile Lys Gln Lys Gly Lys Gly Gly Arg Ile Ile Asn Ile Ser
                165                 170                 175

Ser Val His Glu Phe Ile Pro Trp Pro Met Gly Tyr Thr Ala Tyr Cys
```

```
                    180                 185                 190
Ala Ser Lys Ala Gly Val Ala Met Leu Thr Arg Thr Leu Ala Leu Glu
            195                 200                 205

Tyr Ala Pro Tyr Gly Ile Arg Val Asn Ala Ile Ala Pro Gly Ala Ile
        210                 215                 220

Asn Thr Pro Ile Asn Ala Ser Leu Met Ser Asp Pro Glu Gln Leu Lys
225                 230                 235                 240

Asp Leu Leu Ser Lys Ile Pro Met Gly Arg Leu Gly Glu Pro Glu Glu
            245                 250                 255

Ile Ala Gly Val Val Ala Phe Leu Ala Ser Asp Glu Ala Ser Ala Tyr
        260                 265                 270

Ile Thr Gly Thr Thr Leu Phe Val Asp Gly Gly Met Thr Gln Tyr Pro
        275                 280                 285

Ser Phe Gln His Gly Gly Gly Ser
        290                 295

<210> SEQ ID NO 50
<211> LENGTH: 296
<212> TYPE: PRT
<213> ORGANISM: Artificial Sequence
<220> FEATURE:
<223> OTHER INFORMATION: Calculated ancestral sequence

<400> SEQUENCE: 50

Met Val Lys Glu Val Phe Glu Met Ile Thr Val Tyr Ala Arg Ala Leu
1               5                  10                  15

Ala Glu Arg Ile Met Ser Ala Asn Met Gly Ser Met Met Met Lys Arg
            20                  25                  30

Leu Ser Gly Lys Val Ala Leu Val Thr Gly Ala Ser Ser Gly Ile Gly
        35                  40                  45

Lys Ala Ile Ala Leu Arg Leu Ala Gln Glu Gly Ala Lys Gly Val Val
    50                  55                  60

Val Asn Tyr Arg Ser His Lys Glu Ala Ala Asp Glu Ile Val Glu Glu
65                  70                  75                  80

Ile Lys Lys Ala Gly Gly Glu Ala Ile Ala Val Arg Ala Asp Val Ser
                85                  90                  95

Lys Glu Ala Glu Asp Val Glu Lys Leu Val Glu Gln Thr Val Asp Ala
            100                 105                 110

Phe Gly Arg Leu Asp Ile Leu Val Asn Asn Ala Gly Ile Glu Ser Pro
        115                 120                 125

Lys Ala Pro Val His Glu Met Thr Pro Glu Asp Trp Asp Arg Val Ile
    130                 135                 140

Asp Val Asn Leu Lys Gly Val Phe Leu Cys Thr Arg Glu Ala Val Lys
145                 150                 155                 160

His Met Ile Lys Gln Lys Gly Lys Gly Arg Ile Ile Asn Ile Ser
                165                 170                 175

Ser Val His Gly Phe Ile Gly Gly Pro Met Gly Tyr Thr Ala Tyr Cys
            180                 185                 190

Ala Ser Lys Gly Gly Val Val Met Leu Thr Arg Thr Leu Ala Leu Glu
        195                 200                 205

Tyr Ala Pro Tyr Gly Ile Arg Val Asn Ala Ile Ala Pro Gly Ala Ile
        210                 215                 220

Asn Thr Pro Met Thr Ala Ser Leu Met Ser Asp Pro Glu Gln Leu Lys
225                 230                 235                 240

Glu Leu Leu Ser Gln Ile Pro Met Gly Arg Leu Gly Glu Pro Glu Glu
```

```
            245                 250                 255
Ile Ala Gly Ala Val Ala Phe Leu Ala Ser Asp Glu Ala Ser Ala Tyr
            260                 265                 270

Ile Thr Gly Thr Thr Leu Phe Val Asp Gly Gly Met Thr Ala Tyr Pro
            275                 280                 285

Ser Phe Gln His Gly Gly Gly Ser
            290                 295
```

<210> SEQ ID NO 51
<211> LENGTH: 296
<212> TYPE: PRT
<213> ORGANISM: Artificial Sequence
<220> FEATURE:
<223> OTHER INFORMATION: Calculated ancestral sequence

<400> SEQUENCE: 51

```
Met Val Lys Glu Val Phe Glu Met Ile Thr Val Tyr Ala Arg Ala Leu
1               5                   10                  15

Ala Ser Arg Ile Met Ser Ala Asn Met Gly Ser Met Met Glu Ala Arg
            20                  25                  30

Leu Ser Gly Lys Val Ala Leu Val Thr Gly Ala Ser Ser Gly Ile Gly
            35                  40                  45

Lys Ala Ile Ala Leu Glu Leu Ala Gln Glu Gly Ala Lys Gly Val Val
        50                  55                  60

Val Asn Tyr Arg Ser His Lys Glu Ala Ala Asp Glu Ile Val Glu Glu
65                  70                  75                  80

Ile Lys Glu Ala Gly Gly Glu Ala Met Ala Val Gln Ala Asp Val Ser
            85                  90                  95

Lys Glu Ala Glu Asp Val Gln Lys Leu Val Glu Gln Thr Val Asp Ala
            100                 105                 110

Phe Gly Arg Leu Asp Ile Leu Val Asn Asn Ala Gly Ile Glu Ser Pro
            115                 120                 125

Lys Ala Pro Val His Glu Met Thr Pro Glu Asp Trp Asp Arg Val Ile
        130                 135                 140

Asp Val Asn Leu Lys Gly Val Phe Leu Cys Thr Arg Glu Ala Val Lys
145                 150                 155                 160

His Met Ile Lys Gln Lys Gly Lys Gly Arg Ile Ile Asn Ile Ser
            165                 170                 175

Ser Val His Glu Phe Ile Pro Trp Pro Met Gly Tyr Thr Ala Tyr Cys
            180                 185                 190

Ala Ser Lys Ala Gly Val Ala Met Leu Thr Arg Thr Leu Ala Leu Glu
            195                 200                 205

Leu Ala Pro Tyr Gly Ile Arg Val Asn Ala Ile Ala Pro Gly Ala Ile
        210                 215                 220

Asn Thr Pro Ile Asn Ala Ser Leu Met Ser Asp Pro Glu Gln Leu Lys
225                 230                 235                 240

Asp Leu Leu Ser Lys Ile Pro Met Gly Arg Leu Gly Glu Pro Glu Glu
            245                 250                 255

Ile Ala Gly Val Val Ala Phe Leu Ala Ser Asp Glu Ala Ser Ala Tyr
            260                 265                 270

Ile Thr Gly Thr Thr Leu Phe Val Asp Gly Gly Met Thr Gln Tyr Pro
            275                 280                 285

Ser Phe Gln His Gly Gly Gly Ser
            290                 295
```

```
<210> SEQ ID NO 52
<211> LENGTH: 296
<212> TYPE: PRT
<213> ORGANISM: Artificial Sequence
<220> FEATURE:
<223> OTHER INFORMATION: Calculated ancestral sequence

<400> SEQUENCE: 52

Met Val Lys Glu Val Phe Glu Met Ser Thr Val Tyr Ala Arg Ala Leu
1               5                   10                  15

Ala Ser Arg Ser Met Ser Ala Asn Met Gly Ser Met Met Glu Ala Arg
            20                  25                  30

Leu Glu Gly Lys Val Ala Leu Val Thr Gly Ala Ser Ser Gly Ile Gly
        35                  40                  45

Lys Ala Ile Ala Leu Arg Leu Ala Gln Glu Gly Ala Lys Gly Val Val
    50                  55                  60

Val Asn Tyr Arg Ser His Lys Glu Ala Ala Asp Glu Ile Val Glu Glu
65                  70                  75                  80

Ile Lys Lys Ala Gly Gly Glu Ala Met Ala Val Gln Ala Asp Val Ser
                85                  90                  95

Lys Glu Ala Glu Asp Val Gln Lys Leu Val Glu Gln Thr Val Asp Ala
            100                 105                 110

Phe Gly Arg Leu Asp Ile Leu Val Asn Asn Ala Gly Ile Glu Gly Pro
        115                 120                 125

Lys Ala Pro Phe His Glu Met Thr Pro Glu Asp Trp Asp Arg Val Ile
    130                 135                 140

Asp Val Asn Leu Lys Gly Val Phe Leu Cys Thr Arg Glu Ala Val Lys
145                 150                 155                 160

His Met Ile Lys Gln Lys Gly Lys Gly Gly Ala Ile Ile Asn Ile Ser
                165                 170                 175

Ser Val His Glu Phe Ile Pro Trp Pro Met Gly Tyr Thr Ala Tyr Cys
            180                 185                 190

Ala Ser Lys Ala Gly Val Ala Met Leu Thr Arg Thr Leu Ala Leu Glu
        195                 200                 205

Tyr Ala Pro Tyr Gly Ile Arg Val Asn Ala Ile Ala Pro Gly Ala Ile
    210                 215                 220

Asn Thr Pro Ile Asn Ala Ser Leu Met Ser Asp Pro Glu Gln Leu Lys
225                 230                 235                 240

Asp Leu Leu Ser Lys Ile Pro Met Gly Arg Leu Gly Glu Pro Glu Glu
                245                 250                 255

Ile Ala Gly Val Val Val Phe Leu Ala Ser Asp Glu Ala Ser Ala Tyr
            260                 265                 270

Ile Thr Gly Thr Thr Leu Phe Val Asp Gly Gly Met Thr Gln Tyr Pro
        275                 280                 285

Ser Phe Gln His Gly Gly Gly Ser
    290                 295

<210> SEQ ID NO 53
<211> LENGTH: 33
<212> TYPE: DNA
<213> ORGANISM: Artificial Sequence
<220> FEATURE:
<223> OTHER INFORMATION: Artificially synthesized oligonucleotide
      sequence

<400> SEQUENCE: 53
ttatttgttc actattgcgc aagtaaaggc gga                              33
```

<210> SEQ ID NO 54
<211> LENGTH: 33
<212> TYPE: DNA
<213> ORGANISM: Artificial Sequence
<220> FEATURE:
<223> OTHER INFORMATION: Artificially synthesized oligonucleotide
      sequence

<400> SEQUENCE: 54
tccgccttta cttgcgcaat agtgaacaaa taa                                33

<210> SEQ ID NO 55
<211> LENGTH: 33
<212> TYPE: DNA
<213> ORGANISM: Artificial Sequence
<220> FEATURE:
<223> OTHER INFORMATION: Artificially synthesized oligonucleotide
      sequence

<400> SEQUENCE: 55
atcaagctga tgacgaaaac attggcgctg gaa                                33

<210> SEQ ID NO 56
<211> LENGTH: 33
<212> TYPE: DNA
<213> ORGANISM: Artificial Sequence
<220> FEATURE:
<223> OTHER INFORMATION: Artificially synthesized oligonucleotide
      sequence

<400> SEQUENCE: 56
ttccagcgcc aatgttttcg tcatcagctt gat                                33

<210> SEQ ID NO 57
<211> LENGTH: 33
<212> TYPE: DNA
<213> ORGANISM: Artificial Sequence
<220> FEATURE:
<223> OTHER INFORMATION: Artificially synthesized oligonucleotide
      sequence

<400> SEQUENCE: 57
gacggcggta tgaccctgta tccttcattc cag                                33

<210> SEQ ID NO 58
<211> LENGTH: 33
<212> TYPE: DNA
<213> ORGANISM: Artificial Sequence
<220> FEATURE:
<223> OTHER INFORMATION: Artificially synthesized oligonucleotide
      sequence

<400> SEQUENCE: 58
ctggaatgaa ggatacaggg tcataccgcc gtc                                33

<210> SEQ ID NO 59
<211> LENGTH: 30
<212> TYPE: DNA
<213> ORGANISM: Artificial Sequence
<220> FEATURE:
<223> OTHER INFORMATION: Artificially synthesized oligonucleotide
      sequence

<400> SEQUENCE: 59
cttcggcaag gagggtgcaa aagtggttat                                    30

<210> SEQ ID NO 60
<211> LENGTH: 30
<212> TYPE: DNA
<213> ORGANISM: Artificial Sequence
<220> FEATURE:
<223> OTHER INFORMATION: Artificially synthesized oligonucleotide
      sequence

<400> SEQUENCE: 60
ataaccactt ttgcaccctc cttgccgaag                                      30

<210> SEQ ID NO 61
<211> LENGTH: 33
<212> TYPE: DNA
<213> ORGANISM: Artificial Sequence
<220> FEATURE:
<223> OTHER INFORMATION: Artificially synthesized oligonucleotide
      sequence

<400> SEQUENCE: 61
gctgttgtcg tccaagcgga cgtaacaaaa gag                                  33

<210> SEQ ID NO 62
<211> LENGTH: 33
<212> TYPE: DNA
<213> ORGANISM: Artificial Sequence
<220> FEATURE:
<223> OTHER INFORMATION: Artificially synthesized oligonucleotide
      sequence

<400> SEQUENCE: 62
ctcttttgtt acgtccgctt ggacgacaac agc                                  33

<210> SEQ ID NO 63
<211> LENGTH: 33
<212> TYPE: DNA
<213> ORGANISM: Artificial Sequence
<220> FEATURE:
<223> OTHER INFORMATION: Artificially synthesized oligonucleotide
      sequence

<400> SEQUENCE: 63
ctgaaggatt gggatcgcgt aatcagcacg aac                                  33

<210> SEQ ID NO 64
<211> LENGTH: 33
<212> TYPE: DNA
<213> ORGANISM: Artificial Sequence
<220> FEATURE:
<223> OTHER INFORMATION: Artificially synthesized oligonucleotide
      sequence

<400> SEQUENCE: 64
gttcgtgctg attacgcgat cccaatcctt cag                                  33

<210> SEQ ID NO 65
<211> LENGTH: 33
<212> TYPE: DNA
<213> ORGANISM: Artificial Sequence
<220> FEATURE:
<223> OTHER INFORMATION: Artificially synthesized oligonucleotide
      sequence

<400> SEQUENCE: 65
ctggaatatg cgccgtatgg cattcgtgtc aac                                  33

```
<210> SEQ ID NO 66
<211> LENGTH: 33
<212> TYPE: DNA
<213> ORGANISM: Artificial Sequence
<220> FEATURE:
<223> OTHER INFORMATION: Artificially synthesized oligonucleotide
      sequence

<400> SEQUENCE: 66
gttgacacga atgccatacg gcgcatattc cag                                    33

<210> SEQ ID NO 67
<211> LENGTH: 33
<212> TYPE: DNA
<213> ORGANISM: Artificial Sequence
<220> FEATURE:
<223> OTHER INFORMATION: Artificially synthesized oligonucleotide
      sequence

<400> SEQUENCE: 67
ggcatcacgt tattcgtgga cggcggtatg acc                                    33

<210> SEQ ID NO 68
<211> LENGTH: 33
<212> TYPE: DNA
<213> ORGANISM: Artificial Sequence
<220> FEATURE:
<223> OTHER INFORMATION: Artificially synthesized oligonucleotide
      sequence

<400> SEQUENCE: 68
ggtcataccg ccgtccacga ataacgtgat gcc                                    33

<210> SEQ ID NO 69
<211> LENGTH: 36
<212> TYPE: DNA
<213> ORGANISM: Artificial Sequence
<220> FEATURE:
<223> OTHER INFORMATION: Artificially synthesized oligonucleotide
      sequence

<400> SEQUENCE: 69
atgattccga tgggacgcct gggtgaaccg gaggaa                                 36

<210> SEQ ID NO 70
<211> LENGTH: 36
<212> TYPE: DNA
<213> ORGANISM: Artificial Sequence
<220> FEATURE:
<223> OTHER INFORMATION: Artificially synthesized oligonucleotide
      sequence

<400> SEQUENCE: 70
ttcctccggt tcacccaggc gtcccatcgg aatcat                                 36

<210> SEQ ID NO 71
<211> LENGTH: 30
<212> TYPE: DNA
<213> ORGANISM: Artificial Sequence
<220> FEATURE:
<223> OTHER INFORMATION: Artificially synthesized oligonucleotide
      sequence

<400> SEQUENCE: 71
ttaaatattt tgttaagaac gatataaaag                                        30
```

```
<210> SEQ ID NO 72
<211> LENGTH: 30
<212> TYPE: DNA
<213> ORGANISM: Artificial Sequence
<220> FEATURE:
<223> OTHER INFORMATION: Artificially synthesized oligonucleotide
      sequence

<400> SEQUENCE: 72
cttttatatc gttcttaaca aaatatttaa                                    30

<210> SEQ ID NO 73
<211> LENGTH: 42
<212> TYPE: DNA
<213> ORGANISM: Artificial Sequence
<220> FEATURE:
<223> OTHER INFORMATION: Artificially synthesized oligonucleotide
      sequence

<400> SEQUENCE: 73
tacagcaata agcaggatgc tgaagaggta aaggaagagg tc                      42

<210> SEQ ID NO 74
<211> LENGTH: 42
<212> TYPE: DNA
<213> ORGANISM: Artificial Sequence
<220> FEATURE:
<223> OTHER INFORMATION: Artificially synthesized oligonucleotide
      sequence

<400> SEQUENCE: 74
gacctcttcc tttacctctt cagcatcctg cttattgctg ta                      42

<210> SEQ ID NO 75
<211> LENGTH: 39
<212> TYPE: DNA
<213> ORGANISM: Artificial Sequence
<220> FEATURE:
<223> OTHER INFORMATION: Artificially synthesized oligonucleotide
      sequence

<400> SEQUENCE: 75
gtgattccgt ggccattata cgttcactat gcggcaagt                          39

<210> SEQ ID NO 76
<211> LENGTH: 39
<212> TYPE: DNA
<213> ORGANISM: Artificial Sequence
<220> FEATURE:
<223> OTHER INFORMATION: Artificially synthesized oligonucleotide
      sequence

<400> SEQUENCE: 76
acttgccgca tagtgaacgt ataatggcca cggaatcac                          39

<210> SEQ ID NO 77
<211> LENGTH: 48
<212> TYPE: DNA
<213> ORGANISM: Artificial Sequence
<220> FEATURE:
<223> OTHER INFORMATION: Artificially synthesized oligonucleotide
      sequence

<400> SEQUENCE: 77
ccggaggaaa ttgcggcagc tgcagccttc cttgcttcga aggaagcc                48
```

```
<210> SEQ ID NO 78
<211> LENGTH: 48
<212> TYPE: DNA
<213> ORGANISM: Artificial Sequence
<220> FEATURE:
<223> OTHER INFORMATION: Artificially synthesized oligonucleotide
      sequence

<400> SEQUENCE: 78
ggcttccttc gaagcaagga aggctgcagc tgccgcaatt tcctccgg              48

<210> SEQ ID NO 79
<211> LENGTH: 261
<212> TYPE: PRT
<213> ORGANISM: Bacillus subtilis

<400> SEQUENCE: 79

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Ile Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260
```